US009823235B2

(12) United States Patent
Heron et al.

(10) Patent No.: US 9,823,235 B2
(45) Date of Patent: Nov. 21, 2017

(54) DROPLET INTERFACES

(71) Applicant: Oxford Nanopore Technologies Ltd., Oxford (GB)

(72) Inventors: Andrew John Heron, Oxford (GB); Jason Robert Hyde, Oxford (GB); Clive Gavin Brown, Oxford (GB)

(73) Assignee: Oxford Nanopre Technologies Ltd., Ocford (GB)

( * ) Notice: Subject to any disclaimer, the term of this patent is extended or adjusted under 35 U.S.C. 154(b) by 86 days.

(21) Appl. No.: 14/438,670

(22) PCT Filed: Oct. 23, 2013

(86) PCT No.: PCT/GB2013/052767
§ 371 (c)(1),
(2) Date: Apr. 27, 2015

(87) PCT Pub. No.: WO2014/064444
PCT Pub. Date: May 1, 2014

(65) Prior Publication Data
US 2015/0285781 A1 Oct. 8, 2015

Related U.S. Application Data

(60) Provisional application No. 61/718,982, filed on Oct. 26, 2012.

(51) Int. Cl.
*G01N 33/487* (2006.01)
*G01N 33/50* (2006.01)
(Continued)

(52) U.S. Cl.
CPC ... *G01N 33/48721* (2013.01); *B01D 67/0023* (2013.01); *B01D 69/122* (2013.01);
(Continued)

(58) Field of Classification Search
CPC .. C12Q 1/68; C12Q 1/6869; C12Q 2565/631; B01D 2323/35; B01D 2325/36;
(Continued)

(56) References Cited

U.S. PATENT DOCUMENTS 6,723,814 B2 * 4/2004 Meier .................... A61K 9/009
522/148
6,916,488 B1 * 7/2005 Meier .................. A61K 9/5146
424/1.21

(Continued)

FOREIGN PATENT DOCUMENTS

| WO | WO 01/32146 | 5/2001 |
| WO | WO 01/88025 | 11/2001 |
| WO | WO 2009/024775 | 2/2009 |

OTHER PUBLICATIONS

Lin et al. Conference on Nano/Micro Engineered and Molecular Systems, Feb. 20-23, 2011, Kaohsiung, Taiwan, pp. 1-4.*
(Continued)

*Primary Examiner* — Maureen Wallenhorst
(74) *Attorney, Agent, or Firm* — Wolf, Greenfield & Sacks, P.C.

(57) ABSTRACT

The invention provides a method of forming a membrane between a first volume of polar medium and a second volume of polar medium. In some embodiments, the method involves providing a first volume including polar medium and a second volume including polar medium which are separated from one another by an apolar medium, in which at least one of the first and second volumes has a layer including amphipathic molecules.

105 Claims, 7 Drawing Sheets

(51) Int. Cl.
    B01D 67/00      (2006.01)
    B01D 69/00      (2006.01)
    B01D 71/70      (2006.01)
    B01D 69/12      (2006.01)
    B01D 71/26      (2006.01)
    B01D 71/32      (2006.01)
    B01D 71/58      (2006.01)
    B01D 71/80      (2006.01)
    C12Q 1/68       (2006.01)
    C12M 1/00       (2006.01)

(52) U.S. Cl.
    CPC ............ B01D 71/70 (2013.01); B01D 71/80 (2013.01); C12Q 1/6869 (2013.01); G01N 33/50 (2013.01); B01D 71/26 (2013.01); B01D 71/32 (2013.01); B01D 71/58 (2013.01); B01D 2323/35 (2013.01); B01D 2325/36 (2013.01); B01D 2325/38 (2013.01); Y10T 436/145555 (2015.01)

(58) Field of Classification Search
    CPC ............ B01D 2325/38; B01D 67/0023; B01D 69/122; B01D 71/26; B01D 71/32; B01D 71/58; B01D 71/70; B01D 71/80; G01N 33/48721; G01N 33/50; Y10T 436/145555
    USPC ............... 436/71, 86, 89, 94, 96, 149, 150; 422/82.01; 435/6.1; 525/186, 474
    See application file for complete search history.

(56)         References Cited

U.S. PATENT DOCUMENTS

| 8,101,274 | B2* | 1/2012 | Spedden ................ A61L 27/54 210/633 |
| 8,268,627 | B2* | 9/2012 | Bayley ............... G01N 33/5432 436/55 |
| 8,784,929 | B2* | 7/2014 | Wallace ............. G01N 33/5432 427/2.1 |
| 2009/0074988 | A1* | 3/2009 | Faris ....................... B01J 19/00 427/596 |
| 2015/0265994 | A1* | 9/2015 | Hyde .................... B01L 3/5088 506/6 |

OTHER PUBLICATIONS

Creasy et al. Nanosensors, Biosensors, and Info-Tech Sensors and Systems, Proceedings of SPIE, vol. 7291, 2009, pp. 72910D-1-72910D-12.*

Bayley et al., Droplet interface bilayers. Mol Bios yst. Dec. 2008 ;4(12):1191-208. doi:10.1039/b808893d. Epub Sep. 5, 2008.

PCT/GB2013/052767, Feb. 28, 2014, International Search Report and Written Opinion.

* cited by examiner

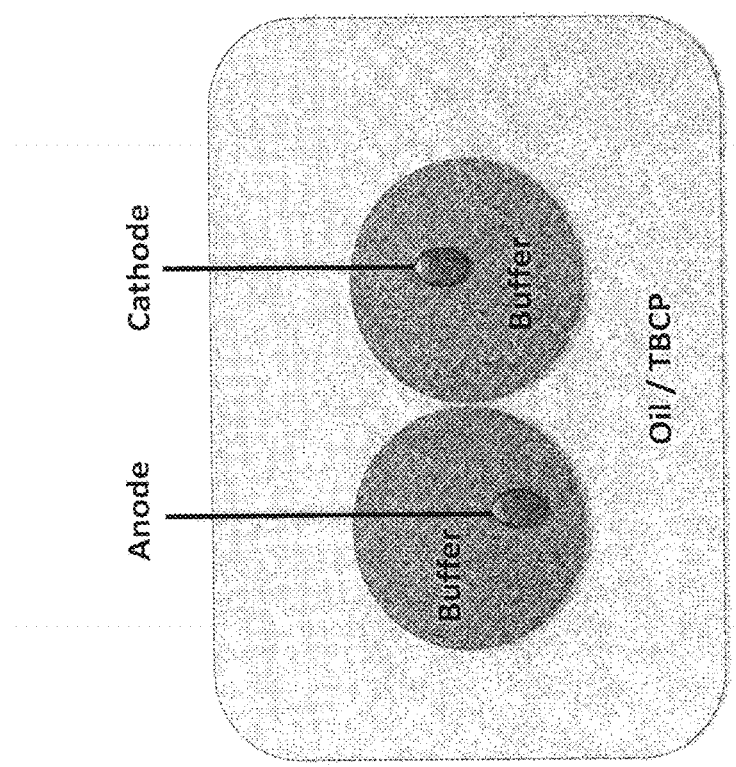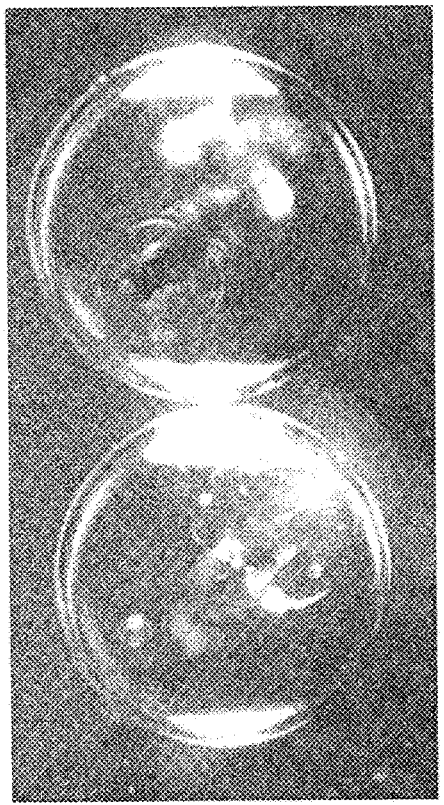
Fig. 4

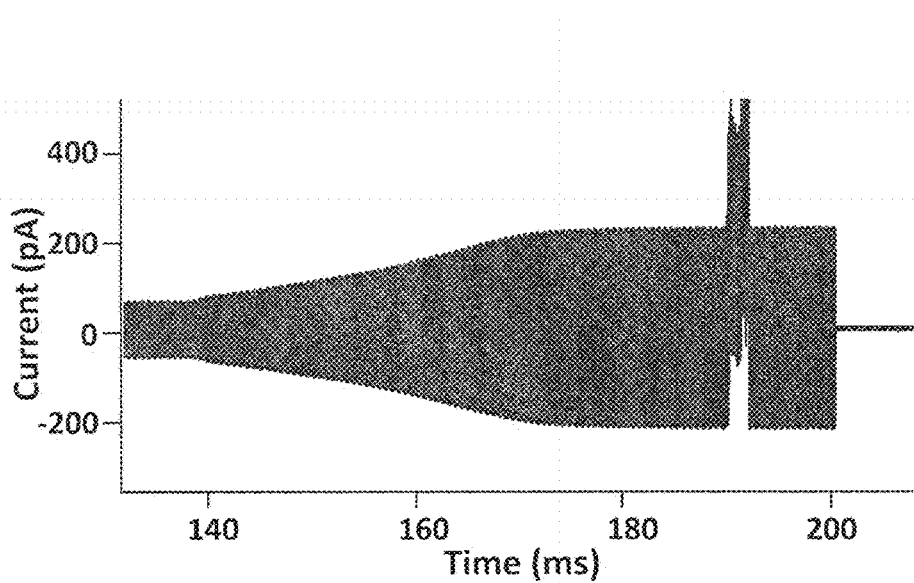
A
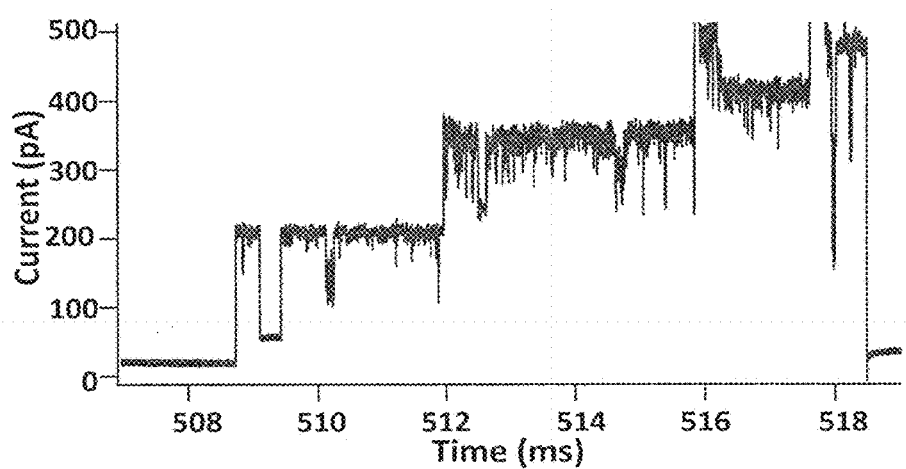
B
Fig. 7

DROPLET INTERFACES

RELATED APPLICATIONS

This application is a national stage filing under 35 U.S.C. §371 of International Application No. PCT/GB2013/052767, filed Oct. 23, 2013, which claims priority under 35 U.S.C. §119(e) to U.S. Provisional Application No. 61/718,982, filed Oct. 26, 2012. The contents of each of these applications are incorporated herein by reference in their entireties for all purposes.

FIELD OF THE INVENTION

The invention relates to a membrane between first and second volumes of a polar medium. The invention also relates to a method of forming such a membrane.

BACKGROUND TO THE INVENTION

Lipid bilayers are thin polar membranes formed from two layers of lipid molecules. Lipid bilayers are found in cell membranes of most living organisms and are usually composed of phospholipids. They are impermeable to most hydrophilic molecules and ions, and enable cells to regulate their salt concentrations and pH by pumping ions across the lipid bilayer using transmembrane proteins known as ion pumps. Lipid bilayers, or more generally bilayers of amphipathic molecules, also serve as excellent platforms for a range of experimental studies. Holden et al, J. Am. Chem. Soc. 2007, 129, 8650-8655 disclose the formation of functional bionetworks of aqueous droplets comprising lipid bilayers provided between droplets. Such networks can act as light sensors, batteries and electrical components by incorporating pumps, channels and pores into the bilayers. Sackmann, Science, New Series, Vol 271, No. 5245 (Jan. 5, 1996), pp. 43-48 provides a review of the scientific and practical applications of supported lipid-protein bilayers including their use in electrooptical biosensors. Jung et al, J. Am. Chem. Soc., 2009, 131 (3), 1006-1014 have developed optical assays for the detection of protein ligand binding on supported bilayers. The provision of ion channels in highly resistive amphipathic lipid bilayers for the detection of DNA and other analytes is well documented, see for example Bayley et al, Nature, Vol 413, September 2001. Aqueous solutions are provided on either side of the lipid bilayer and ion flow through the nanopore takes place under a potential gradient. DNA is caused to translocate the ion channel and the change in ion flow during translocation of DNA through the channel is measured. Due to the high resistance of the lipid bilayer, ion flow takes place exclusively through the ion channel. The lipid bilayer may be suspended across an aperture of a substrate and formed by methods well known in the art such as patch clamping or painting.

WO2009/077734 discloses a plurality of individually addressable lipid bilayers formed across an array of microwell apertures, each microwell containing an electrode and an aqueous medium in contact with the lipid bilayer.

WO2009/012552 discloses a bilayer of amphipathic lipid molecules formed between two droplets comprising a layer of amphipathic molecules containing a hydrophilic medium, the droplets being provided in a hydrophobic medium. Ion flow across the lipid bilayer is measured with electrodes provided within the hydrophilic interior of each droplet.

An amphipathic molecule may be considered as comprising a polar hydrophilic region attached to a non-polar hydrophobic region. A bilayer may be formed from two monolayers of amphiphilic molecules, wherein in aqueous solution, the polar groups face towards the hydrophilic media on either side of the bilayer and the hydrophobic groups face inwards.

WO2009/024775 discloses a method for producing a droplet interface bilayer (DIB) wherein droplets are prepared by contacting an oil/lipid solution with an aqueous solution and the resulting droplets are brought into contact with an aqueous agarose gel support layer.

Phospholipids such as 1,2-diphytanoyl-sn-glycero-3-phosphatidylcoline (DPhPC) are routinely used to form lipid bilayers. However drawbacks that are sometimes associated with lipid bilayers include that they are not particularly robust and are prone to rupture, for example by digestion by enzymes, and are not able to withstand large potential differences.

U.S. Pat. No. 6,723,814 discloses a planar membrane formed from amphiphilic copolymers having hydrophilic and hydrophobic segments. The copolymer may be an ABA triblock having methyloxazoline hydrophilic segments and a dimethylsiloxane hydrophobic core (PMOXA-PDMS-PMOXA). Membranes formed from this triblock are able to withstand higher potential differences than lipid membranes (Table 1 of U.S. Pat. No. 6,723,814).

U.S. Pat. No. 6,916,488 describes the preparation of vesicles made from PMOXA-PDMS-PMOXA in a hydrophilic medium (type ABA). The structure of an amphipathic ABA triblock vesicle (a droplet in a hydrophilic medium having a hydrophilic interior) may be conceptualised as a monolayer of triblock polymer in which the polymer molecules have a linear configuration in which the two hydrophilic 'A' segments face the respective hydrophilic solutions on either side of the vesicle wall. Such a configuration, which is shown in FIG. 1 of U.S. Pat. No. 6,916,488, would not however seem suitable for stabilising aqueous droplets in oil. Such ABA molecules do not therefore seem to be a viable alternative to the lipids described in WO2009/024775, for producing a droplet interface layer from a water-in-oil system.

There is thus an ongoing need to provide alternative methods for producing interface membranes that provide improved stability compared to conventional lipid bilayers.

SUMMARY OF THE INVENTION

It is a finding of the invention that contacting a polar medium with an apolar medium containing ABA molecules results in spontaneous formation of a layer of the ABA molecules around the polar medium, at the apolar-polar interface. Moreover, when two such volumes of polar media are then brought together, through the apolar medium, a stable membrane of ABA molecules forms at the interface between the first and second polar volumes.

The resultant membrane, being synthetic, has been shown to be robust, stable and less susceptible to degradation from detergents and proteins than conventional lipid systems. The membrane is also able to withstand larger potential differences applied across it. Proteins, such as transmembrane protein pores, may be inserted into the membrane and used to characterise target analytes, including DNA.

The successful formation of stable ABA membranes in this manner is counter-intuitive; the fact that the ABA molecules spontaneously form a layer at the polar-apolar interfaces, and then subsequently produce a stable membrane between two polar phases, was unexpected.

Accordingly, the invention provides in a first aspect a method of forming a membrane between a first volume of polar medium and a second volume of polar medium, which method comprises:

(a) providing a first volume comprising polar medium and a second volume comprising polar medium which are separated from one another by an apolar medium, wherein at least one of said first and second volumes comprises a layer comprising amphipathic molecules, at the interface between the polar medium and the apolar medium, wherein each of the amphipathic molecules comprises a first outer hydrophilic group, a hydrophobic core group, and a second outer hydrophilic group, wherein each of the first and second outer hydrophilic groups is linked to the hydrophobic core group; and (b) causing the first and second volumes to come into contact with one another to form a membrane comprising said amphipathic molecules between the first and second volumes of polar medium.

The first volume may be provided within the apolar medium.

In another aspect, the invention provides a membrane which is obtainable by the method of the invention.

In another aspect, the invention provides a system comprising a first volume of a polar medium;

a second volume of a polar medium; and a membrane between the first and second volumes of polar medium, which membrane comprises amphipathic molecules, wherein each of the amphipathic molecules comprises a first outer hydrophilic group, a hydrophobic core group, and a second outer hydrophilic group, wherein each of the first and second outer hydrophilic groups is linked to the hydrophobic core group, and wherein the first volume is within an apolar medium.

The system may further comprise a layer of said amphipathic molecules at an interface between the first volume of polar medium and the apolar medium.

The system may comprise a plurality of first volumes within the apolar medium and a plurality of respective membranes between the plurality of first volumes and the second volume.

The system may comprise a plurality of first volumes within the apolar medium, a plurality of second volumes, and a plurality of membranes provided between the respective first and second volumes. The one or more second volumes may also be provided within the apolar medium.

The invention also provides a volume comprising polar medium, which volume is disposed within an apolar medium, and which volume has a layer comprising amphipathic molecules around a surface thereof, between the polar medium and the apolar medium, wherein each of the amphipathic molecules comprises a first outer hydrophilic group, a hydrophobic core group, and a second outer hydrophilic group, wherein each of the first and second outer hydrophilic groups is linked to the hydrophobic core group, and wherein each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$.

Further provided is a process for producing a volume comprising polar medium, which volume is disposed within an apolar medium, and which volume has a layer of amphipathic molecules around a surface thereof, between the polar medium and the apolar medium, wherein each of the amphipathic molecules comprises a first outer hydrophilic group, a hydrophobic core group, and a second outer hydrophilic group, wherein each of the first and second outer hydrophilic groups is linked to the hydrophobic core group, and wherein each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$, which process comprises:

(i) introducing a volume of a polar medium into an apolar medium;

(ii) providing the amphipathic molecules, in the apolar medium or the polar medium or both, either before or after (i); and (iii) leaving the volume of polar medium for a time sufficient for the layer of the amphipathic molecules to form at the interface between the polar medium and the apolar medium.

The membrane may comprise a transmembrane pore for the determination of the presence of an analyte in or the movement of an analyte through the pore. The presence and/or amount of a transmembrane pore in the membrane may also be determined.

Accordingly, the invention further provides a method of characterising a target analyte, comprising:

(a) contacting the target analyte with a transmembrane pore present in a membrane of the system of the invention as defined herein, (b) taking one or more measurements as the analyte moves with respect to the pore or of the presence of analyte within the pore, wherein the measurements are indicative of one or more characteristics of the target analyte and thereby characterising the target analyte.

Further provided is a method of forming a sensor for characterising a target polynucleotide, comprising forming a complex between (a) a pore present in a membrane of the system of the invention as defined herein, and (b) a polynucleotide binding protein and thereby forming a sensor for characterising the target polynucleotide.

The invention also provides a sensor for characterising a target polynucleotide, comprising a complex between (a) a pore present in a membrane of the system of the invention as defined herein, and (b) a polynucleotide binding protein, and thereby forming a sensor for characterising the target polynucleotide.

Additionally provided is a kit for characterising a target polynucleotide comprising (a) a pore present a membrane of the system of the invention as defined herein, and (b) a polynucleotide binding protein and thereby forming a sensor for characterising the target polynucleotide.

In another aspect, the invention provides an apparatus for characterising target polynucleotides in a sample, comprising (a) a plurality of pores present in a plurality of membranes of one or more systems of the invention as defined herein, and (b) a plurality of polynucleotide binding proteins.

The polar medium may be a hydrophilic medium. The apolar medium may be a hydrophobic medium.

BRIEF DESCRIPTION OF THE FIGURES

FIG. 4 shows how the droplet-interface-bilayer experiment is set-up inside the faraday cage. A) shows a schematic view and B) shows the droplets as viewed from the microscope below the faraday cage.

FIG. 7 shows in section A) an example electrical trace illustrating how the capacitance of two 6-45PE-6 PolymerSource droplets in hexadecane increased over time and in section B) how an example electrical trace illustrating how a sharp current increase was observed when MspA-(B2C) (SEQ ID NO: 25, which is a variant of SEQ ID NO: 2 with the following mutations G75S/G77S/L88N/Q126R) inserted into 6-45PE-6 Polymersource tri-block co-polymer droplets in AR20 oil. Instances where pores have inserted into the tri-block are indicated by black arrows.

DESCRIPTION OF THE SEQUENCE LISTING

Figure 1:
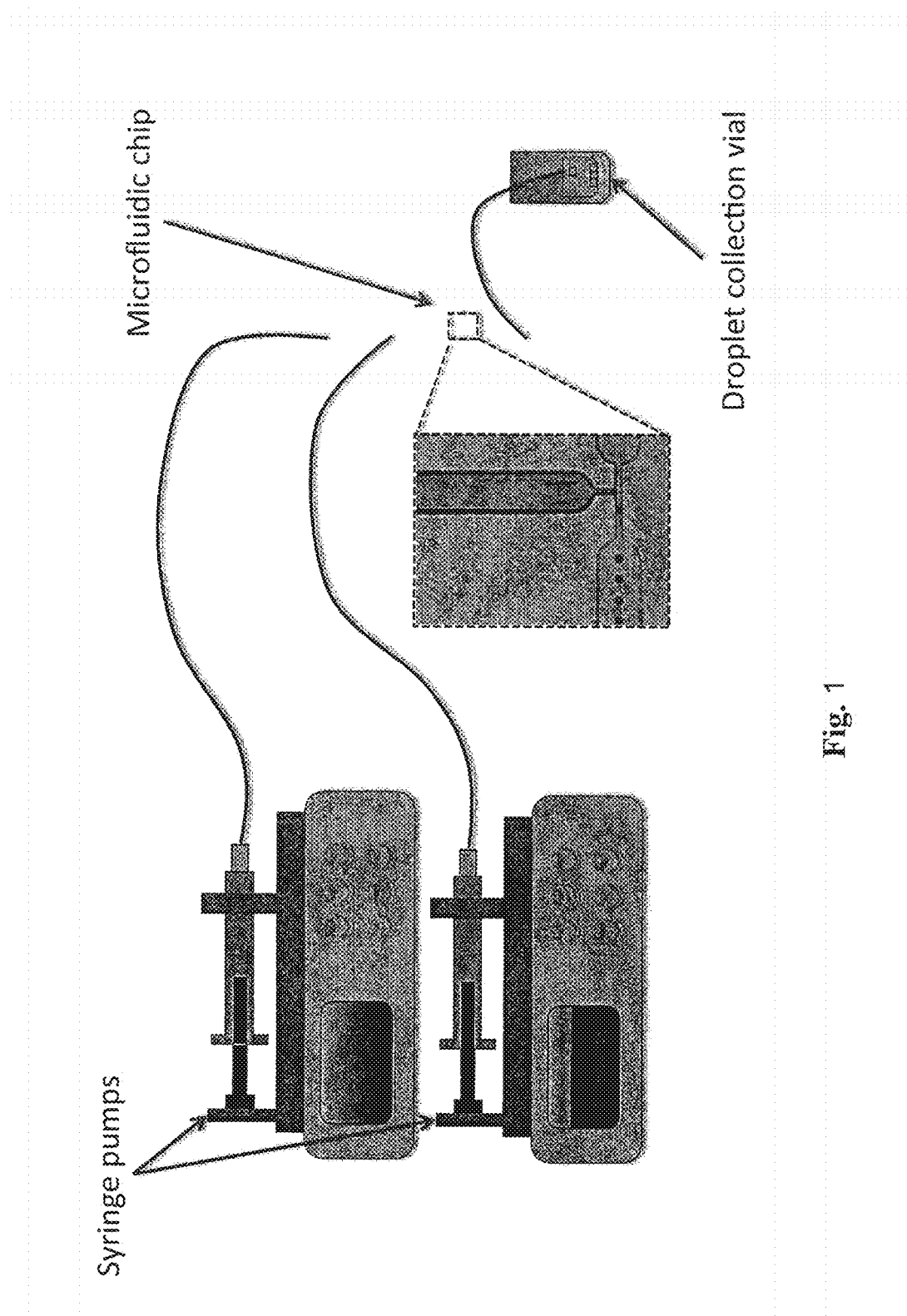
FIG. 1 shows a schematic for the droplet generation setup. This setup consists of two syringe pumps (Elite, Harvard Apparatus), two gastight syringes (Hamilton), Peak tubing (Upchurch Scientific), and a custom made T-junction microfluidic chip.

SEQ ID NO: 1 shows the codon optimised polynucleotide sequence encoding the MS-B 1 mutant MspA monomer. This mutant lacks the signal sequence and includes the following mutations: D90N, D91N, D93N, D118R, D134R and E139K.

SEQ ID NO: 2 shows the amino acid sequence of the mature form of the MS-B1 mutant of the MspA monomer. This mutant lacks the signal sequence and includes the following mutations: D90N, D91N, D93N, D118R, D134R and E139K.

SEQ ID NO: 3 shows the polynucleotide sequence encoding one monomer of α-hemolysin-E111N/K147N (α-HL-NN; Stoddart et al., PNAS, 2009; 106(19): 7702-7707).

SEQ ID NO: 4 shows the amino acid sequence of one monomer of α-HL-NN.

SEQ ID NOs: 5 to 7 show the amino acid sequences of MspB, C and D.

SEQ ID NO: 8 shows the polynucleotide sequence encoding the Phi29 DNA polymerase.

SEQ ID NO: 9 shows the amino acid sequence of the Phi29 DNA polymerase.

SEQ ID NO: 10 shows the codon optimised polynucleotide sequence derived from the sbcB gene from *E. coli*. It encodes the exonuclease I enzyme (EcoExo I) from *E. coli*.

SEQ ID NO: 11 shows the amino acid sequence of exonuclease I enzyme (EcoExo I) from *E. coli*.

SEQ ID NO: 12 shows the codon optimised polynucleotide sequence derived from the xthA gene from *E. coli*. It encodes the exonuclease III enzyme from *E. coli*.

SEQ ID NO: 13 shows the amino acid sequence of the exonuclease III enzyme from *E. coli*. This enzyme performs distributive digestion of 5' monophosphate nucleosides from one strand of double stranded DNA (dsDNA) in a 3'-5' direction. Enzyme initiation on a strand requires a 5' overhang of approximately 4 nucleotides.

SEQ ID NO: 14 shows the codon optimised polynucleotide sequence derived from the recJ gene from *T. thermophilus*. It encodes the RecJ enzyme from *T. thermophilus* (TthRecJ-cd).

SEQ ID NO: 15 shows the amino acid sequence of the RecJ enzyme from *T. thermophilus* (TthRecJ-cd). This enzyme performs processive digestion of 5' monophosphate nucleosides from ssDNA in a 5'-3' direction. Enzyme initiation on a strand requires at least 4 nucleotides.

SEQ ID NO: 16 shows the codon optimised polynucleotide sequence derived from the bacteriophage lambda exo (redX) gene. It encodes the bacteriophage lambda exonuclease.

SEQ ID NO: 17 shows the amino acid sequence of the bacteriophage lambda exonuclease. The sequence is one of three identical subunits that assemble into a trimer. The enzyme performs highly processive digestion of nucleotides from one strand of dsDNA, in a 5'-3' direction (http://www.neb.com/nebecomm/products/productM0262.asp). Enzyme initiation on a strand preferentially requires a 5' overhang of approximately 4 nucleotides with a 5' phosphate.

SEQ ID NO: 18 shows the amino acid sequence of Hel308 Mbu.

SEQ ID NO: 19 shows the Hel308 motif of Hel308 Csy.

SEQ ID NO: 20 shows the amino acid sequence of Hel308 Tga.

SEQ ID NO: 21 shows the amino acid sequence of Hel308 Mhu.

SEQ ID NO: 22 shows the amino acid sequence of TraI Eco.

SEQ ID NO: 23 shows the amino acid sequence of XPD Mbu.

SEQ ID NO: 24 shows the polynucleotide sequence encoding MspA-(B2C) (a variant of SEQ ID NO: 2 with the following mutations: G75S/G77S/L88N/Q126R).

SEQ ID NO: 25 shows the amino acid sequence of MspA-(B2C) (a variant of SEQ ID NO: 2 with the following mutations: G75S/G77S/L88N/Q126R).

DETAILED DESCRIPTION OF THE INVENTION

The method of the first aspect of the invention is straightforward to perform and results in a robust membrane comprising the amphipathic molecules, which can be used in a wide range of studies and applications in the field of biotechnology. The membrane is less susceptible to degradation than a conventional phospholipid bilayer, and is also able to withstand larger potential differences. The membrane has be shown to be more robust and stable having a longer lifetime than a convention lipid bilayer membrane enabling sensors to be provided and stored with prefabricated membranes. It also allows detergent and protein containing samples such as biological samples to be directly applied to the membrane for the detremination of an analyte.

The step of providing the first and second volumes comprising polar medium which are separated from one another by an apolar medium, may be performed very easily. It usually comprises contacting each of the volumes comprising polar medium with an apolar medium.

The polar medium may be provided in the form of one or more droplets and/or one or more beads. Droplets may be formed, for instance by introducing polar medium into the apolar medium by syringe or pipette. Droplet or droplets of polar medium can also be formed in an apolar medium using a microfluidic device, for instance as described in Example 1 hereinbelow. The sizes of the channels within the microfluidic device, and the flow rates of the apolar and polar media through the microfluidic device, can be varied as desired to control the size of the polar droplets produced. Particularly small droplets can be produced by using a microfluidic device, for instance in the size (diameter) range of from 5 µm to 500 µm. Droplets of polar medium formed within a microfluidic device may be transferred into a bulk apolar medium, outside of the microfluidic device, if desired, for further manipulation. A bead or beads of polar medium may be formed within an apolar medium in a similar manner to droplets. For instance, a polar flowable medium which is capable of forming a bead, such as a hydrogel, can be introduced into the apolar medium by pipette or syringe.

Alternatively one or more pre-formed beads comprising polar medium may simply be dispensed into the apolar medium. Examples of such are a non-crosslinked or crosslinked hydrogel such as agarose or sepharose, or porous glass or plastic beads containing a polar medium. A bead may be formed in-situ from a droplet for example by cooling or crosslinking with UV. A bead introduced into the apolar medium may form a droplet, for example by melting.

As an alternative to providing the second volume within the apolar medium, the second volume may be applied to the surface of the apolar medium. This can be done by any suitable method. For instance, the polar medium can be applied to the surface of the apolar medium by pipette or syringe, or by using a flow cell. In another method, a volume of polar medium may be initially provided, for example in a vessel, and the apolar medium applied to the surface of the polar medium. The first volume of polar medium may be subsequently applied to the surface of the apolar medium in order to provide the interface between the two volumes of polar medium.

A plurality of membranes may be provided at the interfaces between a plurality of discrete volumes of polar medium and a layer of polar medium. The volumes of polar medium may be separated from each other by the apolar medium.

The amphipathic molecules may be provided in either the apolar or polar medium. In the case of providing a single volume of the polar medium in the apolar medium, the amphipathic molecules may be provided either before or after the apolar and polar media have been brought into contact with each other. In the case however where a plurality of volumes of polar media are provided in the apolar medium, for example in the form of an emulsion, the amphipathic molecules are preferably provided in either the apolar or polar medium prior to contacting the apolar and polar media to avoid merging of the volumes of polar media. After the amphipathic molecules have been provided and the apolar and polar media have been contacted with one another, a layer comprising the amphipathic molecules forms naturally, at the interface between the apolar medium and the polar medium. The rate of formation of the layer of amphipathic molecules depends upon experimental factors such as the concentration of the amphipathic molecules present and whether they are provided within the apolar volume or within a polar volume. The time taken to form the amphipathic layer may vary and may be of the order of a few minutes or longer. The amphipathic molecules can be provided in the apolar or polar medium by dissolving them in the medium, or for instance by forming vesicles of the amphipathic molecules in the apolar or polar medium. The amphipathic molecules are usually provided in the apolar medium. Typically, they are dissolved in the apolar medium.

Without wishing to be bound by theory, it is thought that the amphipathic molecules in the or each layer at the interface between the polar medium and the apolar medium are probably folded, such that the hydrophobic core group faces outwards, away from the polar medium and towards the apolar medium, and such that the first and second outer hydrophilic groups face inwards, towards the polar medium. Thus, it may be the case that the or each layer of amphiphilic molecules at the interface between the polar medium and the apolar medium comprises a monolayer of the amphipathic molecules which are folded in that way. In cases where the molecule is a triblock ABA type copolymer, wherein each A is an outer hydrophilic polymer segment and B is an inner hydrophobic segment, the molecules in the layer may be U-shaped, such that the hydrophobic B group faces outwards, away from the polar medium and towards the apolar medium, and the two hydrophilic A groups face inwards, towards the polar medium.

The word "causing" as used in step (b) of the first aspect of the invention is intended to encompass, on the one hand, actively bringing the two volumes of polar medium into contact with one another, and, on the other hand, allowing the first and second volumes of polar medium to come into contact by themselves, i.e. allowing the two volumes of polar medium to contact one another and form the membrane by self-assembly.

The volumes of polar medium may be handled by a variety of techniques. For instance, a droplet or bead of polar medium may be moved by disposing an anchor having a hydrophilic outer surface inside the droplet or bead. Movement of the anchor allows the droplet or bead to be moved, for example to bring it into contact with another volume of polar medium. Such manipulation is described in Example 2 below, and in FIGS. 3 and 4, in which two electrodes having hydrophilic, agarose-coated contacts serve as the anchors.

In the step of causing the first and second volumes of polar medium to come into contact, the first and second volumes of polar medium move relatively towards each other through the intervening apolar medium, and intervening apolar medium is displaced from between the two volumes.

As soon as the apolar medium has been sufficiently displaced from between the first and second volumes comprising polar medium, such that the first and second volumes contact each other, the membrane of the amphipathic molecules forms between the first and second volumes.

Figure 5:
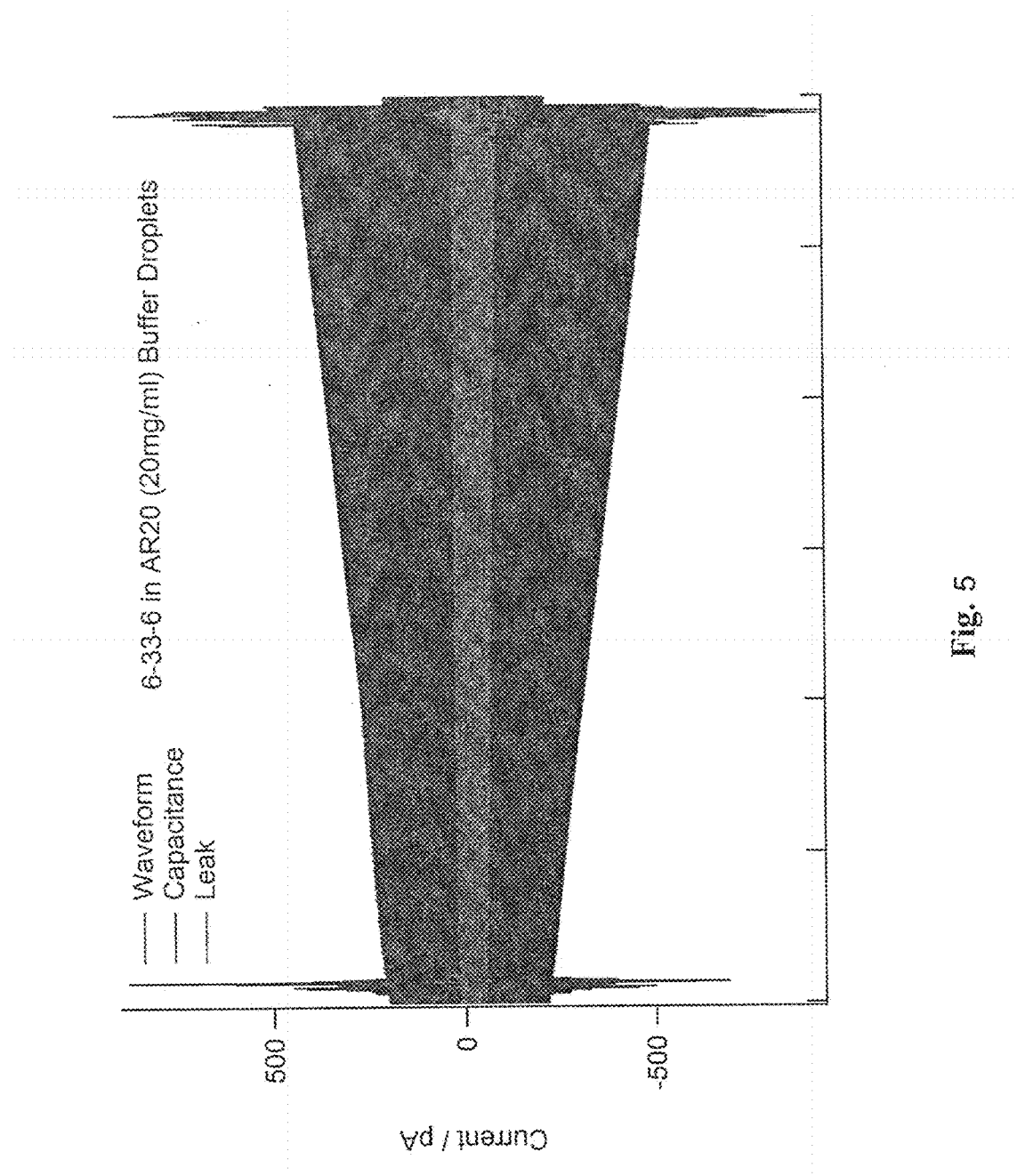
FIG. 5 shows an example electrical trace illustrating how the capacitance of two 6-33-6 PolymerSource droplets in AR20 oil increased over time.

The time taken to form the membrane may vary between seconds to hours depending upon the experimental conditions. The formation of the membrane of amphipathic molecules between two volumes of polar medium can be measured experimentally, by monitoring the change in capacitance between the two volumes of polar medium. Such an experiment is described in Example 2 hereinbelow, in section 2.3. The results are shown in FIG. 5, where the increase in capacitance over time demonstrated the formation of a membrane of the amphiphilic molecules between the two droplets of aqueous buffer that were tested. Thus, by monitoring capacitance, the skilled person can verify formation of the membrane comprising the amphipathic molecules between the first and second volumes of polar medium, in accordance with the method of the present invention.

Without wishing to be bound by theory, it is thought that the membrane formed between the two volumes of polar medium, in the process of the invention, may comprise a monolayer of the amphipathic molecules. In particular, it is thought that the membrane may comprise a monolayer of amphipathic molecules aligned next to one another such that the hydrophobic core groups are aligned to form a middle hydrophobic layer which is not in contact with either of the two volumes of polar medium, and such that the first and second outer hydrophilic groups are aligned to form first and second outer hydrophilic layers which contact the two volumes of polar medium on either side of the membrane.

If that is the case, and if, as postulated hereinbefore, the amphipathic molecules at the interfaces between the polar medium and the apolar medium are folded such that all the hydrophobic core groups face towards the apolar medium and all the first and second outer hydrophilic groups face towards the polar medium, then it is likely that the formation of the membrane in accordance with the method of the invention involves a re-arrangement of the amphipathic molecules, comprising unfolding of the amphipathic molecules.

Another possibility, however, is that the amphipathic molecules remain folded when the method of the invention is performed, and the membrane formed between the two volumes of polar medium comprises a bilayer of the folded amphipathic molecules, in which all the hydrophobic core groups face inwards towards the middle of the bilayer, and all the outer hydrophilic groups face outwards, towards the first and second polar medium. Such a bilayer might for instance be formed by bringing two monolayers of folded amphipathic molecules together, by performing the method of the invention as defined hereinbefore in which each of the first and second volumes of polar medium comprises a layer comprising the amphipathic molecules at the interface between the apolar and polar medium.

The term bilayer as used herein refers to a membrane comprising two monolayers of amphipathic molecules. The term monolayer refers to a membrane formed from a single layer of amphipathic molecules.

The term "bead" typically refers to a volume of a medium which has a defined shape and is generally pre-formed. Examples of such are a glass or plastic porous bead containing polar medium, or an uncrosslinked or crosslinked hydrogel such as agarose or sepharose.

A droplet, on the other hand, refers to a volume of a flowable medium which typically does not have a preformed shape prior to insertion into the apolar medium. Examples of such are an aqueous solution or a hydrogel. The hydrogel may be heated prior to insertion in the apolar medium to increase its flowability. A bead may be formed in situ from a droplet in the apolar medium, for example by cooling or by crosslinking with UV. A bead added to the apolar medium may subsequently form a droplet, for example by melting.

The bead may have any particular shape such as spherical, rod, triangular, square, hexagonal or irregular.

More than two volumes comprising polar medium may be brought together to form a chain or network of such volumes, wherein each volume comprising polar medium contacts a neighbouring volume comprising polar medium. Ion channels may be provided between the respective volumes to provide an interconnected ionic network.

In a preferred embodiment of the method of the invention, the second volume comprising polar medium is provided on the surface of the apolar medium. The second volume may be a sample suspected of comprising a target analyte of interest and measurements can be made to characterise the analyte. The second volume may be a sample comprising a target analyte.

The target analyte may for instance be a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The protein may be a transmembrane protein. In particular, the target analyte is a target polynucleotide. The sample may for instance be a biological sample.

In some embodiments of the method of the invention, the first volume is a droplet or bead and the second volume is a sample comprising or suspected of comprising a target analyte.

The mean diameter of the droplets or beads is typically from about 5 µm to about 500 µm.

The or each layer comprising the amphipathic molecules as well as the resultant membrane or membranes formed between the volumes of polar medium may additionally comprise further molecules.

The further molecules may include functional molecules, such as transmembrane pores and membrane proteins, which will be described in further detail hereinbelow. Additionally or alternatively, the further molecules may include additional amphiphilic molecules, i.e. amphiphilic molecules which do not themselves comprise a first outer polar group, an apolar core group, and a second outer polar group, wherein each of the first and second outer polar groups is linked to the apolar core group. Thus, the further molecules may include amphiphilic molecules such as conventional lipids, for instance phospholipids, fatty acids, fatty acyls, glycerolipids, glycerophospholipids, sphingolipids, sterol lipids, prenol lipids, saccharolipids and polyketides.

The amphipathic molecules in the layer or membrane which comprise a first outer hydrophilic group, a hydrophobic core group, and a second outer hydrophilic group, need not be all of the same type. Rather, mixtures of such amphipathic molecules may be present.

The term "linked" as disclosed with respect to the amphipathic molecules defined herein means bonded, either directly, or via one or more further groups. The one or more further groups may be selected from linker groups, further hydrophilic groups (i.e. hydrophilic groups other than the first and second outer hydrophilic groups), and further hydrophobic groups (i.e. hydrophobic groups other than the hydrophobic core group). Thus, in each of the amphipathic molecules, the first outer hydrophilic group is bonded to the hydrophobic core group either directly or via one or more further groups, and the second outer hydrophilic group is bonded to the hydrophobic core group, either directly or via one or more further groups.

It is important that the first and second outer hydrophilic groups are both linked independently to the hydrophobic core group in this way, because this ensures that the molecule contains at least three distinct regions in terms of hydrophobicity, i.e. an inner hydrophobic region and two outer hydrophilic regions. Thus, it is important that the molecule is not one in which only one of the first and second outer hydrophilic groups is linked to the hydrophobic core group, e.g. a molecule of type AAB in which the first and second hydrophilic groups are bonded to each other and only one of those groups is linked to the hydrophobic core. Rather, each of the first and second outer hydrophilic groups must be linked to the hydrophobic core group independently, to provide at least three distinct regions in the molecule in terms of hydrophobicity.

Generally, for the same reason, the first and second outer hydrophilic groups are independently linked to different regions of the hydrophobic core group, so that the first and second outer hydrophilic groups are spaced apart from one another to some extent by the hydrophobic core group.

Usually, therefore, the first and second outer hydrophilic groups are independently linked to different atoms of the hydrophobic core group. In a preferred embodiment, the first and second outer hydrophilic groups are linked to opposite ends of the hydrophobic core group.

As mentioned above, the amphipathic molecule may further comprise at least one additional hydrophobic or hydrophilic group, i.e. in addition to the first outer hydrophilic group, the hydrophobic core group, and the second outer hydrophilic group.

Thus, for instance, each of said amphipathic molecules may further comprise at least one additional hydrophobic group which is bonded to the first outer hydrophilic group or the second outer hydrophilic group.

The fact that the amphipathic molecules may further comprise one or more additional hydrophobic groups does not necessarily mean that the amphipathic molecule cannot adopt a triblock type configuration, i.e. a configuration in which the molecule still has three distinct regions in terms of hydrophobicity. For instance, when the amphipathic molecule has an additional hydrophobic group which is bonded to the first or second outer hydrophilic group, that additional hydrophobic group may be capable of folding inwards, to align itself with the hydrophobic core group. The resulting conformation of the amphipathic molecule still has "triblock character" because the additional hydrophobic group can fold inwards to essentially become part of a core hydrophobic region together with the hydrophobic core group; essentially, therefore, such an amphipathic molecule still has an inner hydrophobic region and two outer hydrophilic regions, and is therefore very useful for forming a membrane between the first and second volumes of polar medium in accordance with the method of the invention.

In some embodiments, each of the amphipathic molecules further comprises: a first additional hydrophobic group which is bonded to the first outer hydrophilic group, and a second additional hydrophobic group which is bonded to the second outer hydrophilic group. Such amphipathic molecules include pentablock molecules of type BABAB, wherein each group B, which may be the same or different, is a hydrophobic group and each group A, which may be the same or different, is hydrophilic. Typically, each additional hydrophobic group is capable of aligning itself with the hydrophobic core group. As mentioned above, this means that the amphipathic molecule can retain "triblock character" and essentially therefore still have an inner hydrophobic region and two outer hydrophilic regions, which is very useful for the purpose of forming a membrane between the first and second volumes of polar medium in accordance with the method of the invention.

Usually, some or all of the amphipathic molecules are copolymer molecules comprising at least three polymer segments, wherein the hydrophobic core group is an inner hydrophobic polymer segment, B, and the first and second outer hydrophilic groups are first and second outer hydrophilic polymer segments, $A_1$ and $A_2$.

However, amphipathic molecules other than copolymers are also envisaged, such as, for instance, bipolar or bola lipids. They may be naturally occurring or synthetic in nature. Thus, each of the amphipathic molecules may be a bipolar lipid, which comprises two hydrophilic head groups bonded to opposite ends of a hydrophobic tail group. Each hydrophilic head group may optionally be bonded to at least one further hydrophobic tail group. Any suitable such bipolar lipid may be employed. Particularly suitable bipolar lipids include bipolar phospholipids. Examples of bipolar and bola lipids are macrocyclic tetraethers with two polar heads linked by two hydrophobic C40 phytanyl chains as found in *Sulfolobus acidocaldarius*, an extreme thermophilic archaebacterium, bipolar lipids such as disclosed by Brard et at J. Org. Chem., 2007, 72 (22), pp 8267-8279 and bola lipids such as disclosed by Schubert et at J. Phys. Chem. B 2008, 1212, 10041-10044.

Bipolar lipids can be synthesised using synthetic routes that are well known to the skilled chemist, and are also commercially available. The structure and the synthesis of various bipolar lipids is described in the review article "Archaeabacteria bipolar lipid analogues: structure, synthesis and lyotropic properties" Thierry Benvegnu et al., Current Opinion in Colloid & Interface Science, Volume 8, Issue 6, April 2004, Pages 469-479.

Usually, however, each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$.

The copolymer may have for example a linear or graft structure. The first and second outer hydrophilic polymer segments, $A_1$ and $A_2$, may for instance be pendant from the inner hydrophobic polymer segment, B. Usually, $A_1$ and $A_2$, are linked to opposite ends of the inner hydrophobic polymer segment, B. As mentioned above, the term linked in this context means bonded, either directly, or via one or more further groups.

The copolymer may further comprise one or more additional polymer segments, i.e. one or more further polymer segments in addition to $A_1$, $A_2$ and B. The or each additional polymer segment may be the same or different. Typically, the or each additional polymer segment is an additional hydrophilic polymer segment or an additional hydrophobic polymer segment.

Thus, the first outer hydrophilic polymer segment $A_1$ may be bonded to one or more additional polymer segments. Likewise, the second outer hydrophilic polymer segment $A_2$ may be bonded to one or more additional polymer segments. In some embodiments, $A_1$ and $A_2$ are each bonded to one or more additional polymer segments.

Also, the inner hydrophobic polymer segment B may be bonded to the first outer hydrophilic polymer segment $A_1$ either directly or via one or more additional polymer segments. Likewise, the inner hydrophobic polymer segment B may be bonded to the second outer hydrophilic polymer segment $A_2$ directly, or via one or more additional polymer segments. In some embodiments, the inner hydrophobic polymer segment B is bonded to both $A_1$ and $A_2$, directly. However, other embodiments are envisaged in which the inner hydrophobic polymer segment B is bonded to both $A_1$ and $A_2$ via one or more additional polymer segments.

Each of these additional polymer segments may be independently selected from hydrophilic polymer segments and hydrophobic polymer segments.

Accordingly, the copolymer may be a block copolymer of formula (I)

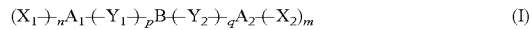

(I)

wherein:
- $A_1$ is said first outer hydrophilic polymer segment;
- B is said inner hydrophobic polymer segment;
- $A_2$ is said second outer hydrophilic polymer segment;
- $X_1$, $Y_1$, $Y_2$ and $X_2$ are additional polymer segments; and
- n, p, q and m are independently either 0 or 1.

The or each additional polymer segment, $X_1$, $Y_1$, $Y_2$ and $X_2$, may be the same or different. Each of these additional polymer segments may be a hydrophilic polymer segment or a hydrophobic polymer segment.

Usually, however, $X_1$ and $X_2$ are both additional hydrophilic polymer segments or $X_1$ and $X_2$ are both additional hydrophobic polymer segments.

Also, typically, $Y_1$ and $Y_2$ are both additional hydrophobic polymer segments or are both additional hydrophilic polymer segments.

In some embodiments, m and n in the block copolymer of formula (I) are both 1, and p and q are both 0, and the copolymer is therefore a pentablock copolymer. One preferred pentablock copolymer is a block copolymer of formula (I) in which m and n are both 1, and p and q are both 0, and $X_1$ and $X_2$ are both additional hydrophobic polymer segments.

Preferably, in this embodiment, the additional hydrophobic polymer segments $X_1$ and $X_2$ are capable of aligning themselves with the inner hydrophobic polymer segment B. For instance, $X_1$ and $X_2$ may be capable of folding inwards to align themselves with segment B. This means that the resulting conformation of the pentablock molecule still has "triblock character" because the hydrophobic polymer segments $X_1$ and $X_2$ essentially become part of a core hydrophobic region together with the hydrophobic core group. The copolymer still therefore has an inner hydrophobic region (comprising B and $X_1$ and $X_2$) and two outer hydrophilic regions, making it very useful for forming a membrane between the first and second volumes of polar medium in accordance with the method of the invention.

Thus, in some embodiments, the copolymer is a pentablock copolymer of formula (II):

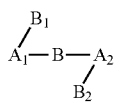 (II)

wherein:
- $A_1$ is said first outer hydrophilic polymer segment;
- B is said inner hydrophobic polymer segment;
- $A_2$ is said second outer hydrophilic polymer segment;
- $B_1$ is a first additional hydrophobic polymer segment; and
- $B_2$ is a second additional hydrophobic polymer segment.

$B_1$ and $B_2$, in this embodiment, are generally capable of folding inwards to align themselves with segment B, meaning that the pentablock molecule can adopt a conformation with "triblock character", with an inner hydrophobic region (comprising B, $B_1$ and $B_2$ aligned to each other) and two outer hydrophilic regions, $A_1$ and $A_2$, making the amphipathic molecule particularly useful for forming a membrane between the first and second volumes of a polar medium in accordance with the method of the invention.

Usually, however, the copolymer is a triblock copolymer having a middle polymer segment which is said inner hydrophobic polymer segment B, and two outer polymer segments which are said first and second outer hydrophilic polymer segments, $A_1$ and $A_2$.

Thus, typically, in formula (I), m, n, p and q are all 0, and the copolymer is a triblock copolymer of formula (III)

$$A_1\text{-B-}A_2 \qquad (III)$$

wherein
- $A_1$ is said first outer hydrophilic polymer segment;
- B is said inner hydrophobic polymer segment;
- $A_2$ is said second outer hydrophilic polymer segment.

Usually, in this embodiment, $A_1$ and $A_2$, are bonded to opposite ends of the inner hydrophobic polymer segment, B.

The following substituent definitions apply with respect to the compounds defined hereinbelow:

A $C_1$-$C_{18}$ alkyl group is an unsubstituted or substituted, straight or branched chain saturated hydrocarbon radical having from 1 to 18 carbon atoms. Typically it is $C_1$-$C_{10}$ alkyl, for example methyl, ethyl, propyl, butyl, pentyl, hexyl, heptyl, octyl, nonyl or decyl, or $C_1$-$C_6$ alkyl, for example methyl, ethyl, propyl, butyl, pentyl or hexyl, or $C_1$-$C_4$ alkyl, for example methyl, ethyl, i-propyl, n-propyl, t-butyl, s-butyl or n-butyl. The alkyl group may however be a $C_3$-$C_{18}$ alkyl, or for instance a $C_4$-$C_{12}$ alkyl group. When an alkyl group is substituted it typically bears one or more substituents selected from unsubstituted $C_1$-$C_{10}$ alkyl, substituted or unsubstituted aryl (for instance phenyl), cyano, amino, $C_1$-$C_{10}$ alkylamino, di($C_1$-$C_{10}$)alkylamino, arylamino, diarylamino, arylalkylamino, amido, acylamido, oxo, halo, ester, acyl, acyloxy, $C_1$-$C_{10}$ alkoxy, aryloxy, haloalkyl, $C_1$-$C_{10}$ alkylthio, sulfhydryl, arylthio, sulfonyl, phosphate ester. Particularly if the alkyl group is within a hydrophilic group or within a hydrophilic polymer segment, it may bear one or more substituents selected from hydroxy, carboxy, sulfonic acid, phosphoric acid, and phosphonic acid. Examples of substituted alkyl groups include haloalkyl, hydroxyalkyl, aminoalkyl, alkoxyalkyl and alkaryl groups. The term alkaryl, as used herein, pertains to a $C_1$-$C_{18}$ alkyl group in which at least one hydrogen atom has been replaced with an aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—). Typically a substituted $C_1$-$C_{18}$ alkyl group carries 1, 2 or 3 substituents, for instance 1 or 2, or more typically 1 substituent. Usually, however, the alkyl groups herein are unsubstituted, unless otherwise specified.

A vinyl $C_1$-$C_{18}$ alkanoate is therefore a compound of formula R—C(O)O—CH=CH$_2$, wherein R is a $C_1$-$C_{18}$ alkyl group as defined above.

Unless otherwise specified an "alkyl" group specified herein may be taken to be a $C_1$-$C_{18}$alkyl group as defined above, or for instance a $C_1$-$C_{10}$ alkyl group as defined above, or a $C_1$-$C_4$ alkyl group as defined above.

A $C_1$-$C_{10}$ perfluoroalkyl group is a straight or branched chain saturated perfluorinated hydrocarbon radical having from 1 to 10 carbon atoms. A $C_2$-$C_{10}$ perfluoroalkyl group is a straight or branched chain saturated perfluorinated hydrocarbon radical having from 2 to 10 carbon atoms. "Perfluorinated" in this context means completely fluorinated such that there are no carbon-bonded hydrogen atoms replaceable with fluorine. Examples of $C_2$-$C_{12}$ perfluoro alkyl groups are perfluoroethyl ($C_2$) perfluoropropyl ($C_3$) (including perfluoro-n-propyl and perfluoro-iso-propyl), perfluorobutyl ($C_4$) (including perfluoro-n-butyl, perfluoro-sec-butyl and perfluoro-tert-butyl), perfluoropentyl ($C_5$), perfluorohexyl ($C_6$), perfluoroheptyl ($C_7$), perfluorooctyl ($C_8$), perfluorononyl ($C_9$), and perfluorodecyl ($C_{10}$), including straight chained and branched isomers thereof. $C_1$-$C_{10}$ perfluoroalkyl also of course includes —$CF_3$.

"Partially fluorinated" means that one or more carbon-bonded hydrogen atoms are present which are replaceable with fluorine. Thus, a partially fluorinated $C_1$-$C_{10}$ alkyl group is a $C_1$-$C_{10}$ alkyl group which is substituted with one or more fluorine atoms but which is not perfluorinated. Likewise, a partially fluorinated $C_2$-$C_{10}$ alkyl group is a $C_2$-$C_{10}$ alkyl group which is substituted with one or more fluorine atoms but which is not perfluorinated. Thus, partially fluorinated $C_1$-$C_{10}$ alkyl groups and $C_2$-$C_{10}$ alkyl groups have at least one carbon-bonded hydrogen atom which is replaceable with fluorine.

A $C_3$-$C_{10}$ cycloalkyl group is an unsubstituted or substituted alkyl group which is also a cyclyl group; that is, a monovalent moiety obtained by removing a hydrogen atom from an alicyclic ring atom of a carbocyclic ring of a carbocyclic compound, which moiety has from 3 to 10 carbon atoms (unless otherwise specified), including from 3 to 10 ring atoms. Examples of groups of $C_3$-$C_{10}$ cycloalkyl groups include $C_3$-$C_7$ cycloalkyl. When a $C_3$-$C_{10}$ cycloalkyl group is substituted it typically bears one or more substituents selected from those specified above for alkyl groups. Typically a substituted $C_{3-10}$ cycloalkyl group carries 1, 2 or 3 substituents, for instance 1 or 2, or more typically 1 substituent. Usually, however, the cycloalkyl groups herein are unsubstituted unless otherwise specified. Examples of $C_{3-10}$ cycloalkyl groups include, but are not limited to, those derived from saturated monocyclic hydrocarbon compounds, which $C_{3-10}$ cycloalkyl groups are unsubstituted or substituted as defined above: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_m$).

An aryl group is a substituted or unsubstituted, monocyclic or bicyclic aromatic group which typically contains from 6 to 14 carbon atoms, preferably from 6 to 10 carbon atoms in the ring portion. Examples include phenyl, naphthyl, indenyl and indanyl groups. An aryl group may be unsubstituted or substituted, for instance, as specified above for alkyl. Typically it carries 0, 1, 2 or 3 substituents.

A $C_2$-$C_{18}$ alkene is a straight or branched chain alkene having from 2 to 20 carbon atoms. A halo group is chlorine, fluorine, bromine or iodine (a chloro group, a fluoro group, a bromo group or an iodo group). It is typically chlorine, fluorine or bromine. A $C_2$-$C_{18}$ haloalkene is therefore a straight or branched chain alkene having from 2 to 20 carbon atoms which is substituted with one or more halo groups. Typically it carries 0, 1, 2, 3 or 4 halo substituents.

As used herein the term amino represents a group of formula —$NH_2$. The term $C_1$-$C_6$ alkylamino represents a group of formula —$NHR'$ wherein $R'$ is a $C_1$-$C_6$ alkyl group, as defined previously. The term di($C_1$-$C_6$ alkylamino) represents a group of formula —$NR'R''$ wherein $R'$ and $R''$ are the same or different and represent $C_1$-$C_6$ alkyl groups as defined previously.

The inner hydrophobic polymer segment B of the amphipathic copolymer molecules defined above typically comprises a polymer of one or more monomers selected from: $C_1$-$C_{18}$ alkyl and $C_3$-$C_{18}$ cycloalkyl acrylates and methacrylates, $C_3$-$C_{18}$ alkylacrylamides and methacrylamides, acrylonitrile, methacrylonitrile, vinyl $C_1$-$C_{18}$ alkanoates, $C_2$-$C_{18}$ alkenes, $C_2$-$C_{18}$ haloalkenes, styrene, ($C_{1-6}$ alkyl)styrene, $C_4$-$C_{12}$ alkyl vinyl ethers, $C_2$-$C_{10}$ perfluoro-alkyl acrylates and methacrylates and correspondingly partially fluorinated acrylates and methacrylates, $C_3$-$C_{12}$ perfluoroalkylethylthiocarbonylaminoethyl acrylates and methacrylates, acryloxy- and methacryloxyalkylsiloxanes, di($C_1$-$C_6$ alkyl)halosilane, N-vinylcarbazole, $C_1$-$C_{12}$ alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane. Thus, the inner hydrophobic polymer segment B may comprise a polymer of any one of the monomers listed above, or it may comprise a copolymer of any two or more of the monomers listed above.

The inner hydrophobic polymer segment B may for instance comprise a polymer of one or more $C_2$-$C_{18}$ alkene monomers, for instance a polymer of one or more $C_2$-$C_4$ alkene monomers.

Alternatively, the hydrophobic polymer segment B could for instance comprise a polymer of one or more di($C_1$-$C_6$ alkyl)halosilane monomers, for instance a polymer of dimethylchlorosilane.

When one or more additional hydrophobic polymer segments are present in the copolymer, for instance when any of $X_1$, $Y_1$, $Y_2$ and $X_2$ is present in formula (I) above and is an additional hydrophobic polymer segment, or for instance when the copolymer is a pentablock copolymer of formula (II) above which comprises the additional hydrophobic polymer segments $B_1$ and $B_2$, the or each additional hydrophobic polymer segment, which may be the same or different, typically comprises a polymer of one or more monomers selected from: $C_1$-$C_{18}$ alkyl and $C_3$-$C_{18}$ cycloalkyl acrylates and methacrylates, $C_3$-$C_{18}$ alkylacrylamides and methacrylamides, acrylonitrile, methacrylonitrile, vinyl $C_1$-$C_{18}$ alkanoates, $C_2$-$C_{18}$ alkenes, $C_2$-$C_{18}$ haloalkenes, styrene, ($C_{1-6}$ alkyl)styrene, $C_4$-$C_{12}$ alkyl vinyl ethers, $C_2$-$C_{10}$ perfluoro-alkyl acrylates and methacrylates and correspondingly partially fluorinated acrylates and methacrylates, $C_3$-$C_{12}$ perfluoroalkylethylthiocarbonylaminoethyl acrylates and methacrylates, acryloxy- and methacryloxyalkylsiloxanes, N-vinylcarbazole, $C_1$-$C_{12}$ alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane. Thus, the or each additional hydrophobic polymer segment may comprise a polymer of any one of the monomers listed above, or may comprise a copolymer of any two or more of the monomers listed above.

The or each additional hydrophobic polymer segment may for instance comprise a polymer of one or more $C_2$-$C_{18}$ alkene monomers, for instance a polymer of one or more $C_2$-$C_4$ alkene monomers. The or each additional hydrophobic polymer segment may additionally or alternatively comprise a polymer of one or more di($C_1$-$C_6$ alkyl)halosilane monomers, for instance a polymer of dimethylchlorosilane.

Usually, the inner hydrophobic polymer segment B in the copolymer comprises a polymer selected from polysiloxane, polyalkene, perfluoropolyether, perfluoroalkyl polyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, poly(propylene oxide) and copolymers thereof.

Particularly preferred options for the inner hydrophobic polymer segment B include polysiloxane and polyalkene. Suitable polysiloxanes include polydimethylsiloxane and polydiphenylsiloxane. The inner hydrophobic polymer segment B may for instance comprise a polysiloxane block having terminal alkylene groups. Thus, the inner hydrophobic polymer segment B may comprise a polydimethylsiloxane block having terminal alkylene groups, or for instance a polydiphenylsiloxane block having terminal alkylene groups.

Alternatively, the inner hydrophobic polymer segment B may comprise a polyalkene. The polyalkene may for instance be polyethylene, polypropylene, or polybutene. Typically, the polyalkene is polyethylene.

Similarly, when one or more additional hydrophobic polymer segments are present in the copolymer, for instance when any of $X_1$, $Y_1$, $Y_2$ and $X_2$ is present in formula (I) above and is an additional hydrophobic polymer segment, or for instance when the copolymer is a pentablock copolymer of formula (II) above which comprises the additional hydrophobic polymer segments $B_1$ and $B_2$, the or each additional hydrophobic polymer segment, which may be the same or different, typically comprises a polymer selected from polysiloxane, polyalkene, perfluoropolyether, perfluoroalkyl polyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, poly(propylene oxide) and copolymers thereof. Particularly preferred options for the one or more additional hydrophobic polymer segments include polysiloxane and polyalkene. Suitable polysiloxanes include polydimethylsiloxane and polydiphenylsiloxane. The polyalkene may for instance be polyethylene, polypropylene or polybutene. Typically, the polyalkene is polyethylene.

Typically, therefore, the inner hydrophobic polymer segment B and, when present, the or each additional hydrophobic polymer segment, comprise a polysiloxane or a polyalkene. Suitable polysiloxanes include polydimethylsiloxane and polydiphenylsiloxane. The polyalkene may for instance be polyethylene, polypropylene, or polybutene.

In some embodiments, however, the inner hydrophobic polymer segment B comprises an unsaturated polymer. The unsaturated polymer may for instance be selected from: a polymer of a conjugated aliphatic or alicyclic diene, which diene is unsubstituted or substituted by halogen or $C_1$-$C_6$ alkyl; a polymer of an alkyne or dialkyne, which alkyne or dialkyne is unsubstituted or substituted by $C_1$-$C_6$ alkyl or trimethylsilyl; a copolymer of a conjugated diene and a hydrophilic or hydrophobic vinylic monomer; and partially hydrated derivatives thereof. Particularly preferred unsaturated polymers that may be used include: cis-, trans-, iso- or syndiotactic poly-1,2-butadiene, poly-1,4-butadiene or polyisoprene, poly-pentenamer, polychloroprene or polypiperylen; butadiene- or isoprene-copolymers with hydrophilic or hydrophobic vinylic monomers selected from acrylonitrile, styrene, acrylic acid, or hydroxyethylmethacrylate; or poly-1-trimethylsilyl-propyne.

When present, the or each additional hydrophobic polymer segment, which may be the same or different, may comprise an unsaturated polymer. When the or each additional hydrophobic polymer segment comprises an unsaturated polymer, the unsaturated polymer may for instance be selected from any of those listed above for the inner hydrophobic polymer segment B.

The inner hydrophobic polymer segment B and, when present, the or each additional hydrophobic polymer segment, may include a single type of polymer or more than one type of polymer, such as two or more of those discussed above.

The mean molecular weight of the inner hydrophobic polymer segment B is typically from about 150 to about 50,000. In some embodiments, it is from about 800 to about 15,000, or for instance from about 1,000 to about 12,000. In some embodiments, it is from about 5,000 to about 12,000, for instance from about 4,000 to about 11,000.

Likewise, the mean molecular weight of the or each additional hydrophobic polymer segment, when present, is typically from about 150 to about 50,000. In some embodiments, it is from about 800 to about 15,000, or for instance from about 1,000 to about 12,000. In some embodiments, it is from about 5,000 to about 12,000, for instance from about 4,000 to about 11,000.

The first outer hydrophilic polymer segment, $A_1$, and the second outer hydrophilic polymer segment, $A_2$, of the amphipathic copolymer molecules defined above may be the same or different. Usually, $A_1$ and $A_2$, which are the same or different, comprise a polymer of a monomer which is independently selected from: hydroxyl-substituted $C_1$-$C_6$ alkyl acrylates and methacrylates, acrylamide, methacrylamide, ($C_1$-$C_6$ alkyl)acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted ($C_1$-$C_6$ alkyl)acrylamides and methacrylamides, hydroxyl-substituted $C_1$-$C_6$ alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino($C_1$-$C_6$ alkyl)-, mono($C_1$-$C_6$ alkylamino)($C_1$-$C_6$alkyl)- and di($C_1$-$C_6$ alkylamino)($C_1$-$C_6$ alkyl)-acrylates and methacrylates, allyl alcohol, 3-trimethylammonium 2-hydroxypropylmethacrylate chloride, dimethylaminoethyl methacrylate (DMAEMA), dimethylaminoethylmethacrylamide, glycerol methacrylate, N-(1,1-dimethyl-3-oxobutyl)acrylamide, cyclic imino ethers, vinyl ethers, cyclic ethers including epoxides, cyclic unsaturated ethers, N-substituted aziridines, [beta]-lactones and [beta]-lactames, ketene acetals, vinyl acetals and phosphoranes. Thus, each of the first and second outer hydrophilic polymer segments, $A_1$ and $A_2$, may comprise a polymer of any one of the monomers listed above, or a copolymer of any two or more of the monomers listed above.

The first outer hydrophilic polymer segment, $A_1$, and the second outer hydrophilic polymer segment, $A_2$, which are the same or different, may for instance comprise a polymer of a monomer which is independently selected from: a cyclic imino ether selected from 2-methyloxazoline, 2-oxazoline, and 2-oxazoline having an alkenyl group in the 2 position, and a vinyl ether selected from methyl vinyl ether, ethyl vinyl ether and methoxy ethyl vinyl ether. More typically, $A_1$ and $A_2$ comprise a polymer of a monomer selected from: 2-methyloxazoline, 2-oxazoline, and 2-oxazoline having an alkenyl group in the 2 position. For instance, one or both of $A_1$ and $A_2$ may comprise poly(2-methyloxazoline) (PMOXA).

Likewise, when one or more additional hydrophilic polymer segments are present in the copolymer, for instance when any of $X_1$, $Y_1$, $Y_2$ and $X_2$ is present in formula (I) above and is an additional hydrophilic polymer segment, the or each additional hydrophilic polymer segment, which may be the same or different, typically comprises a polymer of one or more monomers selected from: hydroxyl-substituted $C_1$-$C_6$ alkyl acrylates and methacrylates, acrylamide, methacrylamide, ($C_1$-$C_6$ alkyl)acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted ($C_1$-$C_6$ alkyl)acrylamides and methacrylamides, hydroxyl-substituted $C_1$-$C_6$ alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino($C_1$-$C_6$ alkyl)-, mono($C_1$-$C_6$ alkylamino)($C_1$-$C_6$ alkyl)- and di($C_1$-$C_6$ alkylamino)($C_1$-$C_6$ alkyl)-acrylates and methacrylates, allyl alcohol, 3-trimethylammonium 2-hydroxypropylmethacrylate chloride, dimethylaminoethyl methacrylate (DMAEMA), dimethylaminoethylmethacrylamide, glycerol methacrylate, N-(1,1-dimethyl-3-oxobutyl)acrylamide, cyclic imino ethers, vinyl ethers, cyclic ethers including epoxides, cyclic unsaturated ethers, N-substituted aziridines, [beta]-lactones and [beta]-lactames, ketene acetals, vinyl acetals and phosphoranes. Thus, the or each additional hydrophilic polymer segment, when present, may comprise a polymer of any one of the monomers listed above, or a copolymer of any two or more of the monomers listed above.

In some embodiments, the or each additional hydrophilic polymer segment, when present, comprises a polymer of a monomer selected from: a cyclic imino ether selected from 2-methyloxazoline, 2-oxazoline, and 2-oxazoline having an alkenyl group in the 2 position, and a vinyl ether selected from methyl vinyl ether, ethyl vinyl ether and methoxy ethyl vinyl ether. More typically, the or each additional hydrophilic polymer segment comprises a polymer of a monomer selected from: 2-methyloxazoline, 2-oxazoline, and 2-oxazoline having an alkenyl group in the 2 position. For instance, the or each additional hydrophilic polymer segment may comprise poly(2-methyloxazoline) (PMOXA).

Typically, the first outer hydrophilic polymer segment, $A_1$, and the second outer hydrophilic polymer segment, $A_2$, which are the same or different, comprise a polymer selected from: polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly (vinylether), poly (N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more thereof, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

A particularly important choice of polymer for the hydrophilic polymer segments is poly(2-methyloxazoline), i.e. PMOXA. Thus, usually, the first outer hydrophilic polymer segment $A_1$ and the second outer hydrophilic polymer segment $A_2$ comprise poly(2-methyloxazoline).

Similarly, the or each additional hydrophilic polymer segment, when present, which may be the same or different when more than one additional hydrophilic polymer segment is present, comprises a polymer selected from: polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly (vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more thereof, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof. The additional hydrophilic polymer segment(s), when present, may for instance comprise poly(2-methyloxazoline), i.e. PMOXA.

The first outer hydrophilic polymer segment $A_1$ and the second outer hydrophilic polymer segment $A_2$ and, when present, the or each additional hydrophilic polymer segment, may include a single type of polymer or more than one type of polymer, such as two or more of those discussed above.

The mean molecular weight of the first and second outer hydrophilic polymer segments $A_1$ and $A_2$ respectively, is typically from about 150 to about 50,000. In some embodiments, it is from about 500 to about 15,000, or for instance from about 1,000 to about 12,000. In some embodiments, it is from about 5,000 to about 12,000, for instance from about 4,000 to about 11,000.

Likewise, the mean molecular weight of the or each additional hydrophilic polymer segment, when present, is typically from about 150 to about 50,000. In some embodiments, it is from about 500 to about 15,000, or for instance from about 1,000 to about 12,000. In some embodiments, it is from about 5,000 to about 12,000, for instance from about 4,000 to about 11,000.

Thus, the molecular weight of each of the first outer hydrophilic polymer segment $A_1$, the second outer hydrophilic polymer segment $A_2$ and, when present, the or each additional hydrophilic polymer segment, is usually from 150 to 50,000. In some embodiments, it is from about 500 to about 15,000, or for instance from about 1,000 to about 12,000. In some embodiments, it is from about 5,000 to about 12,000, for instance from about 4,000 to about 11,000.

The amphipathic molecules may for instance comprise the triblock copolymer poly(2-methyloxazoline)-block-poly(dimethylsiloxane)-block-poly(2-methyloxazoline) (PMOXA-PDMS-PMOXA), or for instance the triblock copolymer poly(2-methyloxazoline)-block-poly(ethylene)-block-poly(2-methyloxazoline) (PMOXA-PE-PMOXA).

The amphipathic molecules may for instance comprise the triblock copolymer 6-33-6 (PMOXA-PDMS-PMOXA), 6-32-6 (PMOXA-PDMS-PMOXA), or 6-45PE-6 (PMOXA-PE-PMOXA).

Polymeric amphipathic molecules of the kind defined above, i.e. copolymer molecules comprising an inner hydrophobic polymer segment, and first and second outer hydrophilic polymer segments, may be synthesised using standard copolymer synthesis methods which are known in the art. Such methods are described in U.S. Pat. No. 6,723,814 B2 and U.S. Pat. No. 6,916,488 B1.

Any suitable polymerisation method can be used to prepare a hydrophobic or hydrophilic polymer segment as appropriate, including for instance photopolymerisation, redox polymerisation, anionic polymerisation, condensation reactions, addition reactions, and chain polymerisation reactions. Also, a wide variety of hydrophilic and hydrophobic polymers which can be used as segments in an amphipathic block copolymer are commercially available.

Hydrophilic and hydrophobic segments may be linked together by, for instance, polymerizing a suitable hydrophilic monomer in the presence of a suitably functionalized hydrophobic polymer segment, such that a block of units of the hydrophilic monomer grows from the site of functionalization of the hydrophobic segment. Alternatively a suitable hydrophobic monomer may be polymerised in the presence of a suitably functionalized hydrophilic polymer segment, such that a block of units of the hydrophobic monomer grows from the site of functionalization of the hydrophilic segment.

Thus, for instance, a triblock copolymer may be prepared by polymerising one or more suitable hydrophilic monomers in the presence of a hydrophobic polymer segment which has been functionalised twice, such that two blocks of units of a hydrophilic monomer grow from the sites of functionalization of the hydrophobic segment.

The functionalized segment may be referred to as a macroinitiator. Suitable macroinitiators may bear one or more thermally or photochemically activatable cationic or anionic functional groups, or for instance one or more thermally or photochemically activatable radical initiator groups. Anionic polymerization, polycondensation, and polyaddition can also be used. Specific examples of preferred photochemically activatable cationic initiator groups are triflate ($-O-SO_2-CF_3$), $-I$ (iodide), $-O$-mesyl, $-O$-tosyl, and $-Cl^+AgSbF_6$. The initiator group is usually linked to the starting segment in a way that provides a covalent bond between the terminal group of the starting segment and the first monomer forming the growing segment that is attached to the starting segment during the graft copolymerization for preparing the amphiphilic copolymer. Grafting means that polymer chains are grown from a monomer either in terminal or in pendant position onto another preformed polymer.

The initiator group may be introduced into a preformed polymer segment in any suitable way, for example through linkage of cationic or thermal initiator groups to functional groups present on the starting monomer. Triflate groups, for instance, can be introduced by reaction of terminal or pendent functional hydroxyl groups with activated triflic acid derivatives such as $(CF_3SO)_2O$.

It is also possible to change the monomer during graft copolymerization such that, for example, first hydrophilic segments $A_1$ and $A_2$ are grown on a preformed hydrophobic segment B and then further hydrophobic segments $B_1$ and $B_2$ are attached to the termini of the earlier prepared segments $A_1$ and $A_2$. Such a process could be used to a pentablock copolymer of formula (II) as defined herein.

The polymerizations can of course be carried out in the presence or absence of a solvent, and under appropriate conditions for the polymerisation reaction to take place, as are known to the skilled person. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone or cyclohexanone, hydrocarbons such as toluene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture.

Complete copolymers comprising an inner hydrophobic polymer segment, and first and second outer hydrophilic polymer segments are also commercially available, from companies such as Polymer Source™, in Montreal, Canada, and for instance High Force Research Limited, Durham, UK.

The polar medium employed in the first and second volumes of polar medium (and in any further volumes of polar medium that are present) may be freely chosen for purpose. It is typically a liquid or a gel. The polar medium employed in the first and second volumes may be the same or different.

In the case that the polar medium is an aqueous medium. Any suitable aqueous medium may be employed. The aqueous medium may comprise one or more solutes. The aqueous medium may comprise a buffer in order to regulate the pH of the polar medium as appropriate.

The polar medium may further comprise a redox couple, or a member of a redox couple which may be partially oxidised or reduced to provide the redox couple. The redox couple may choen from those known in the art such as $Fe^{2+}/Fe^{3+}$, ferrocene/ferrocenium or $Ru^{2+}/Ru^{3+}$. Examples of such are ferro/ferricyanide, ruthenium hexamine and ferrocene carboxlic acid.

The apolar medium is typically an oil. The oil may be a single compound, or the oil may comprise a mixture of two or more compounds.

The oil may for instance comprise silicone oil. Suitable silicone oils include, for instance, poly(phenyl methyl siloxane) and poly(dimethylsiloxane) (PDMS). The silicone oil may comprise a hydroxy-terminated silicone oil, for instance hydroxy terminated PDMS.

The oil may comprise a single silicone oil, for instance poly(phenyl methyl siloxane) or poly(dimethylsiloxane). Alternatively, the oil may comprise a mixture of two or more different silicone oils, for instance a mixture of poly(phenyl methyl siloxane) and poly(dimethylsiloxane).

Additionally or alternatively, the oil may comprise a hydrocarbon, for instance hexadecane. When the oil comprises a hydrocarbon it may comprise a single hydrocarbon compound, or a mixture of two or more hydrocarbons. In some embodiments, the apolar medium is an oil which is a mixture comprising: (a) one or more hydrocarbons, and (b) one or more silicone oils.

Any suitable hydrocarbon may be employed as the oil. The hydrocarbon employed must of course be a liquid at the temperature of operation, i.e. at the temperature at which the method is performed. Typically, this is room temperature, and therefore the hydrocarbon employed will usually be one which is a liquid at room temperature.

When the oil comprises a hydrocarbon, the hydrocarbon may be branched or unbranched, for example a hydrocarbon having from 5 to 30 carbon atoms, or from 5 to 20 carbon atoms (although hydrocarbons of lower molecular weight would require control of evaporation). Preferably, the hydrocarbon is a liquid at the operating temperature of the droplet used in the invention. Suitable examples include alkanes or alkenes, such as hexadecane, decane, pentane or squalene. Usually, the oil comprises a hydrocarbon.

Typically the hydrocarbon is an unsubstituted $C_{10}$-$C_{20}$ alkane, for instance hexadecane.

In some embodiments the hydrocarbon is a longer-chain hydrocarbon, such as unsubstituted $C_{16}$-$C_{30}$ alkane, such as squalene.

Other types of oil are also possible. For example, the oil may be a fluorocarbon or a bromo-substituted $C_{10}$-$C_{30}$ alkane (for instance a bromo-substituted $C_{10}$-$C_{20}$ alkane, e.g. bromododecane). Typically, however, the oil comprises silicone oil or a hydrocarbon.

Silicone oil can be advantageous on account of its density being close to that of water, which ensures that a volume of polar medium which is an aqueous volume, is approximately neutrally buoyant in water. The silicone oil may for instance be poly(phenyl methyl siloxane), which has a density of about 1 g·cm$^{-3}$.

When a hydrocarbon is employed as the apolar medium the hydrocarbon typically has from 5 to 20 carbon atoms (a $C_5$-$C_{20}$ hydrocarbon), more typically from 10 to 20 carbon atoms (a $C_{10}$-$C_{20}$ hydrocarbon). Typically, it is an alkane or an alkene. Thus, the hydrocarbon may be a $C_5$-$C_{20}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. Thus, in a preferred embodiment, the hydrocarbon is an unsubstituted $C_5$-$C_{20}$ alkane, preferably an unsubstituted $C_{10}$-$C_{20}$ alkane. The hydrocarbon may for instance be squalene, hexadecane or decane. In one embodiment it is hexadecane. However, in some embodiments the hydrocarbon may be substituted with a halogen atom, for instance bromine.

The apolar medium may comprise a mixture of silicone oil and a hydrocarbon. The silicone oil and hydrocarbon in the mixture may be as further defined above. Typically, the hydrocarbon is an unsubstituted $C_{10}$-$C_{20}$ alkane, preferably hexadecane. The silicone oil may for instance be poly (phenyl methyl siloxane) or PDMS.

In certain preferred embodiments of the method of the invention, the apolar medium comprises hexadecane, poly (phenyl methyl siloxane) or PDMS, the amphipathic molecules comprise poly(2-methyloxazoline)-block-poly(dimethylsiloxane)-block-poly(2-methyloxazoline) (PMOXA-PDMS-PMOXA), or poly(2-methyloxazoline)-block-poly (ethylene)-block-poly(2-methyloxazoline) (PMOXA-PE-PMOXA), and the polar medium comprises an aqueous buffer solution.

A membrane protein or a transmembrane pore may be provided in one or more of the volumes of polar medium, for insertion into the membrane or membranes that are formed between the volumes of polar medium by the method of the invention. The present method does not limit the choice of membrane protein. Thus, the membrane protein may be of any type. The use of integral membrane proteins has been demonstrated, but it is equally expected that peripheral membrane proteins could be used. The present method applies to any membrane proteins including the two major classes that are β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction.

Thus, typically, in the method of the invention for forming a membrane, at least one of the volumes of polar medium contains a membrane protein, which membrane protein is capable of insertion into the membrane or membranes comprising the amphipathic molecules. Suitable membrane proteins include, but are not limited to, pumps, channels (for instance ion channels) and/or pores, receptor proteins, transporter proteins, and/or proteins which effect cell recognition or a cell-to-cell interaction. Usually, the membrane protein is a pump, channel and/or pore.

Usually the membrane protein is a transmembrane pore, for instance MspA-(B2C), which is used in Example 2 hereinbelow, or for instance an α-hemolysin (αHL) pore. However, any suitable membrane protein can be used including the two major classes that is β-barrels or α-helical bundles.

Typically, the transmembrane protein pore is:

(a) selected from a hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP) and WZA;

(b) formed of eight identical subunits as shown in SEQ ID NO: 2 or is a variant thereof in which one or more of the seven subunits has at least 50% homology to SEQ ID NO: 2 based on amino acid identity over the entire sequence and retains pore activity; or (c) α-hemolysin formed of seven identical subunits as shown in SEQ ID NO: 4 or is a variant thereof in which one or more of the seven subunits has at least 50% homology to SEQ ID NO: 4 based on amino acid identity over the entire sequence and retains pore activity.

Usually, when a membrane protein is present in the polar medium, the concentration of the membrane protein in the polar medium is equal to or greater than 1 ng mL$^{-1}$, for instance, equal to or greater than 10 ng mL$^{-1}$. Typically, the concentration of membrane protein in the polar medium is from 10 ng mL$^{-1}$ to 1000 ng mL$^{-1}$, or for instance from 200 ng mL$^{-1}$ to 800 ng mL$^{-1}$.

Insertion of the pore into the membrane may be assisted by the presence of a surfactant. The surfactant advantageously has chemical moeities which are compatable with the copolymer. For example it has been shown that organosilicon based surfactants such as Silwet® can assist in the insertion of protein pores such as MspA into copolymers comprising siloxanes. The surfactant may be provided in the polar medium or the apolar medium.

The method of the invention for forming a membrane may further comprise taking a measurement on the volumes of polar medium to perform an experiment involving a process occurring at or through the membrane between the volumes. For instance, the method may further comprise bringing electrodes into electrical contact with the volumes of polar medium and taking an electrical measurement using the electrodes. Such measurements can be used to characterise a target analyte, as is explained further hereinbelow.

The various features of the system of the invention may be as further defined hereinbefore for the method of the invention.

In the system of the invention, the first volume of polar medium may be completely or partially within the apolar medium. In the case where the first volume of polar medium is partially within the apolar medium, a portion of it may not be in contact with the apolar medium. The membrane may thus be formed between a second volume comprising polar medium contacted with the exposed portion of the first volume.

Since the first volume comprising polar medium is within the apolar medium, either completely or partially, the system of the invention may further comprise a layer of the amphipathic molecules at an interface between the first volume of polar medium and the apolar medium.

The first volume of polar medium in the system of the invention is usually a droplet or bead. In some embodiments each of the first and second volumes in the system of the invention is a droplet or bead.

In some embodiments each of the first and second volumes of polar medium is within said apolar medium and the system further comprises: a layer of said amphipathic molecules at an interface between the first volume of polar medium and the apolar medium, and a layer of said amphipathic molecules at an interface between the second volume of polar medium and the apolar medium.

The system may additionally comprise one or more further volumes of polar medium, and one or more further membranes comprising said amphipathic molecules, wherein each further volume of polar medium is separated from another of the volumes of polar medium (which may be the first or second volume, or another further volume) by a said further membrane comprising said amphipathic molecules. The first volume, the second volume, and the one or more further volumes of polar medium may be droplets or beads.

The system may for instance comprise a further volume of polar medium adjacent to the first volume, and a further membrane comprising the amphipathic molecules between the first volume of polar medium and the further volume of polar medium.

Similarly, the system can comprise a further volume of polar medium adjacent to the second volume, and a further membrane comprising the amphipathic molecules between the second volume of polar medium and the further volume of polar medium.

One important setup is one in which the system comprises a plurality of first volumes of polar medium within the apolar medium and a plurality of respective membranes between the plurality of first volumes and the second volume. The or each first volume may be a droplet or bead. The second volume may comprise a sample comprising or suspected of comprising a target analyte of interest. The target analyte may be as further defined hereinbefore.

In another case, the system may comprise a plurality of first volumes of polar medium within the apolar medium, a plurality of second volumes of polar medium, and a plurality of membranes provided between the respective first and second volumes. The one or more second volumes may also be provided within the apolar medium.

The invention also provides a volume, as defined hereinbefore, comprising polar medium, which volume is disposed within a apolar medium, and which volume has a layer comprising the amphipathic molecules around a surface thereof, between the polar medium and the apolar medium. The volume may be usefully employed in the method of the invention as defined herein for forming a membrane. A process for producing the volume is also provided herein.

The various features of the volume of the invention, and the process of the invention for producing the volume, may be as further defined herein for the method of the invention for forming a membrane, or for the system of the invention. Thus, for instance, in the volume of the invention, or in the process of the invention for producing the volume of the invention, the amphipathic copolymer, the layer comprising the amphipathic molecules, the polar medium and the apolar medium, may all be as defined hereinbefore for the method or system of the invention. Usually, the volume of the polar medium is a droplet or bead of said polar medium.

Methods of Characterising Analytes

The invention provides a method of characterising a target analyte. The method comprises contacting the target analyte with a pore present in a membrane of the system of the invention such that the target analyte moves through the pore. One or more characteristics of the target analyte are then measured as the analyte moves with respect to the pore using standard methods known in the art. One or more characteristics of the target analyte are preferably measured as the analyte moves through the pore. Steps (a) and (b) are preferably carried out with a potential applied across the pore. As discussed in more detail below, the applied potential may results in the formation of a complex between the pore and a polynucleotide binding protein. The applied potential may be a voltage potential. Alternatively, the applied potential may be a chemical potential. An example of this is using a salt gradient across an amphiphilic layer. A salt gradient is disclosed in Holden et al., J Am Chem Soc. 2007 Jul. 11; 129(27):8650-5.

The method of the invention is for characterising a target analyte. The method is for charaterising at least one analyte. The method may concern charaterising two or more analytes. The the method may comprise charaterising any number of analytes, such as 2, 5, 10, 15, 20, 30, 40, 50, 100 or more analytes.

The target analyte is preferably a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant. The method may concern characterising two or more analytes of the same type, such as two or more proteins, two or more nucleotides or two or more pharmaceuticals. Alternatively, the method may concern characterising two or more analytes of different types, such as one or more proteins, one or more nucleotides and one or more pharmaceuticals.

The target analyte can be secreted from cells. Alternatively, the target analyte can be an analyte that is present inside cells such that the analyte must be extracted from the cells before the invention can be carried out.

The analyte is preferably an amino acid, a peptide, a polypeptides and/or a protein. The amino acid, peptide, polypeptide or protein can be naturally-occurring or non-naturally-occurring. The polypeptide or protein can include within them synthetic or modified amino acids. A number of different types of modification to amino acids are known in the art. Suitable amino acids and modifications thereof are above. For the purposes of the invention, it is to be understood that the target analyte can be modified by any method available in the art.

The protein can be an enzyme, an antibody, a hormone, a growth factor or a growth regulatory protein, such as a cytokine. The cytokine may be selected from interleukins, preferably IFN-1, IL-1, IL-2, IL-4, IL-5, IL-6, IL-10, IL-12 and IL-13, interferons, preferably IL-$\gamma$, and other cytokines such as TNF-$\alpha$. The protein may be a bacterial protein, a fungal protein, a virus protein or a parasite-derived protein.

The target analyte is preferably a nucleotide, an oligonucleotide or a polynucleotide. A nucleotide typically contains a nucleobase, a sugar and at least one phosphate group. The nucleobase is typically heterocyclic. Nucleobases include, but are not limited to, purines and pyrimidines and more specifically adenine, guanine, thymine, uracil and cytosine. The sugar is typically a pentose sugar. Nucleotide sugars include, but are not limited to, ribose and deoxyribose. The nucleotide is typically a ribonucleotide or deoxyribonucleotide. The nucleotide typically contains a monophosphate, diphosphate or triphosphate. Phosphates may be attached on the 5' or 3' side of a nucleotide.

Nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), 5-methylcytidine monophosphate, 5-methylcytidine diphosphate, 5-methylcytidine triphosphate, 5-hydroxymethylcytidine monophosphate, 5-hydroxymethylcytidine diphosphate, 5-hydroxymethylcytidine triphosphate, cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP), 5-methyl-2'-deoxycytidine monophosphate, 5-methyl-2'-deoxycytidine diphosphate, 5-methyl-2'-deoxycytidine triphosphate, 5-hydroxymethyl-2'-deoxycytidine monophosphate, 5-hydroxymethyl-2'-deoxycytidine diphosphate and 5-hydroxymethyl-2'-deoxycytidine triphosphate. The nucleotides are preferably selected from AMP, TMP, GMP, UMP, dAMP, dTMP, dGMP or dCMP. The nucleotides may be abasic (i.e. lack a nucleobase). The nucleotides may contain additional modifications. In particular, suitable modified nucleotides include, but are not limited to, 2'amino pyrimidines (such as 2'-amino cytidine and 2'-amino uridine), 2'-hyrdoxyl purines (such as, 2'-fluoro pyrimidines (such as 2'-fluorocytidine and 2'fluoro uridine), hydroxyl pyrimidines (such as 5'-α-P-borano uridine), 2'-O-methyl nucelotides (such as 2'-O-methyl adenosine, 2'-O-methyl guanosine, 2'-O-methyl cytidine and 2'-O-methyl uridine), 4'-thio pyrimidines (such as 4'-thio uridine and 4'-thio cytidine) and nucleotides have modifications of the nucleobase (such as 5-pentynyl-2'-deoxy uridine, 5-(3-aminopropyl)-uridine and 1,6-diaminohexyl-N-5-carbamoylmethyl uridine).

Oligonucleotides are short nucleotide polymers which typically have 50 or fewer nucleotides, such 40 or fewer, 30 or fewer, 20 or fewer, 10 or fewer or 5 or fewer nucleotides. The oligonucleotides may comprise any of the nucleotides discussed above, including the abasic and modified nucleotides.

The method of the invention is preferably for characterising a target polynucleotide. A polynucleotide, such as a nucleic acid, is a macromolecule comprising two or more nucleotides. The polynucleotide or nucleic acid may comprise any combination of any nucleotides. The nucleotides can be naturally occurring or artificial. One or more nucleotides in the target polynucleotide can be oxidized or methylated. One or more nucleotides in the target polynucleotide may be damaged. For instance, the polynucleotide may comprise a pyrimidine dimer. Such dimers are typically associated with damage by ultraviolet light and are the primary cause of skin melanomas. One or more nucleotides in the target polynucleotide may be modified, for instance with a label or a tag. Suitable labels are described above. The target polynucleotide may comprise one or more spacers.

Nucleotides are defined above. Nucleotides present in the polynucleotide typically include, but are not limited to, adenosine monophosphate (AMP), guanosine monophosphate (GMP), thymidine monophosphate (TMP), uridine monophosphate (UMP), cytidine monophosphate (CMP), cyclic adenosine monophosphate (cAMP), cyclic guanosine monophosphate (cGMP), deoxyadenosine monophosphate (dAMP), deoxyguanosine monophosphate (dGMP), deoxythymidine monophosphate (dTMP), deoxyuridine monophosphate (dUMP) and deoxycytidine monophosphate (dCMP). The nucleotides are preferably selected from AMP, TMP, GMP, CMP, UMP, dAMP, dTMP, dGMP, dCMP and dUMP.

A nucleotide may be abasic (i.e. lack a nucleobase). A nucleotide may also lack a nucleobase and a sugar (i.e. is a C3 spacer).

The nucleotides in the polynucleotide may be attached to each other in any manner. The nucleotides are typically attached by their sugar and phosphate groups as in nucleic acids. The nucleotides may be connected via their nucleobases as in pyrimidine dimers.

The polynucleotide may be single stranded or double stranded. At least a portion of the polynucleotide is preferably double stranded. A single stranded polynucleotide may have one or more primers hybridised thereto and hence comprise one or more short regions of double stranded polynucleotide. The primers may be the same type of polynucleotide as the target polynucleotide or may be a different type of polynucleotide.

The polynucleotide can be a nucleic acid, such as deoxyribonucleic acid (DNA) or ribonucleic acid (RNA). The target polynucleotide can comprise one strand of RNA hybridized to one strand of DNA. The polynucleotide may be any synthetic nucleic acid known in the art, such as peptide nucleic acid (PNA), glycerol nucleic acid (GNA), threose nucleic acid (TNA), locked nucleic acid (LNA) or other synthetic polymers with nucleotide side chains.

The whole or only part of the target polynucleotide may be characterised using this method. The target polynucleotide can be any length. For example, the polynucleotide can be at least 10, at least 50, at least 100, at least 150, at least 200, at least 250, at least 300, at least 400 or at least 500 nucleotide pairs in length. The polynucleotide can be 1000 or more nucleotide pairs, 5000 or more nucleotide pairs in length or 100000 or more nucleotide pairs in length.

The target analyte, such as a target polynucleotide, is present in any suitable sample. The invention is typically carried out on a sample that is known to contain or suspected to contain the target analyte, such as the target polynucleotide. Alternatively, the invention may be carried out on a sample to confirm the identity of one or more target analytes, such as one or more target polynucleotides, whose presence in the sample is known or expected.

The sample may be a biological sample. The invention may be carried out in vitro on a sample obtained from or extracted from any organism or microorganism. The organism or microorganism is typically archaean, prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs. Alternatively a sample of plant origin is typically obtained from a commercial crop, such as a cereal, legume, fruit or vegetable, for example wheat, barley, oats, canola, maize, soya, rice, bananas, apples, tomatoes, potatoes, grapes, tobacco, beans, lentils, sugar cane, cocoa, cotton.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

The pore is present in the or a membrane of the system of the invention. Any of the embodiments discussed above with reference to the membrane of the system of the invention are applicable to the characterising method of the invention. The analyte, such as a target polynucleotide, may be coupled directly to the membrane. The analyte, such as a target polynucleotide, is preferably coupled to the membrane via a linker. Preferred linkers include, but are not limited to, polymers, such as polynucleotides, polyethylene glycols (PEGs) and polypeptides. If a polynucleotide is coupled directly to the membrane, then some data will be lost as the characterising run cannot continue to the end of the polynucleotide due to the distance between the membrane and the interior of the pore. If a linker is used, then the polynucleotide can be processed to completion. If a linker is used, the linker may be attached to the polynucleotide at any position. The linker is preferably attached to the polynucleotide at the tail polymer.

The coupling may be stable or transient. For certain applications, the transient nature of the coupling is preferred. If a stable coupling molecule were attached directly to either the 5' or 3' end of a polynucleotide, then some data will be lost as the characterising run cannot continue to the end of the polynucleotide due to the distance between the bilayer and the interior of the pore. If the coupling is transient, then when the coupled end randomly becomes free of the bilayer, then the polynucleotide can be processed to completion. Chemical groups that form stable or transient links with the membrane are discussed in more detail below. The analyte, such as a target polynucleotide, may be transiently coupled to an amphiphilic layer, such as a lipid bilayer using cholesterol or a fatty acyl chain. Any fatty acyl chain having a length of from 6 to 30 carbon atoms, such as hexadecanoic acid, may be used.

Coupling of analytes, such as a target polynucleotide, to synthetic lipid bilayers has been carried out previously with various different tethering strategies. These are summarised in Table 1 below.

TABLE 1

| Attachment group | Type of coupling | Reference |
| --- | --- | --- |
| Thiol | Stable | Yoshina-Ishii, C. and S. G. Boxer (2003). "Arrays of mobile tethered vesicles on supported lipid bilayers." *J Am Chem Soc* 125(13): 3696-7. |
| Biotin | Stable | Nikolov, V., R. Lipowsky, et al. (2007). "Behavior of giant vesicles with |

TABLE 1-continued

| Attachment group | Type of coupling | Reference |
| --- | --- | --- |
| | | anchored DNA molecules." *Biophys J* 92(12): 4356-68 |
| Cholestrol | Transient | Pfeiffer, I. and F. Hook (2004). "Bivalent cholesterol-based coupling of oligonucletides to lipid membrane assemblies." *J Am Chem Soc* 126(33): 10224-5 |
| Lipid | Stable | van Lengerich, B., R. J. Rawle, et al. "Covalent attachment of lipid vesicles to a fluid-supported bilayer allows observation of DNA-mediated vesicle interactions." *Langmuir* 26(11): 8666-72 |

Polynucleotides may be functionalized using a modified phosphoramidite in the synthesis reaction, which is easily compatible for the addition of reactive groups, such as thiol, cholesterol, lipid and biotin groups. These different attachment chemistries give a suite of attachment options for polynucleotides. Each different modification group tethers the polynucleotide in a slightly different way and coupling is not always permanent so giving different dwell times for the polynucleotide to the bilayer. The advantages of transient coupling are discussed above.

Coupling of polynucleotides can also be achieved by a number of other means provided that a reactive group can be added to the polynucleotide. The addition of reactive groups to either end of DNA has been reported previously. A thiol group can be added to the 5' of ssDNA using polynucleotide kinase and ATPγS (Grant, G. P. and P. Z. Qin (2007). "A facile method for attaching nitroxide spin labels at the 5' terminus of nucleic acids." Nucleic Acids Res 35(10): e77). A more diverse selection of chemical groups, such as biotin, thiols and fluorophores, can be added using terminal transferase to incorporate modified oligonucleotides to the 3' of ssDNA (Kumar, A., P. Tchen, et al. (1988). "Nonradioactive labeling of synthetic oligonucleotide probes with terminal deoxynucleotidyl transferase." Anal Biochem 169(2): 376-82).

Alternatively, the reactive group could be considered to be the addition of a short piece of DNA complementary to one already coupled to the bilayer, so that attachment can be achieved via hybridisation. Ligation of short pieces of ssDNA have been reported using T4 RNA ligase I (Troutt, A. B., M. G. McHeyzer-Williams, et al. (1992). "Ligation-anchored PCR: a simple amplification technique with single-sided specificity." Proc Natl Acad Sci USA 89(20): 9823-5). Alternatively either ssDNA or dsDNA could be ligated to native dsDNA and then the two strands separated by thermal or chemical denaturation. To native dsDNA, it is possible to add either a piece of ssDNA to one or both of the ends of the duplex, or dsDNA to one or both ends. Then, when the duplex is melted, each single strand will have either a 5' or 3' modification if ssDNA was used for ligation or a modification at the 5' end, the 3' end or both if dsDNA was used for ligation. If the polynucleotide is a synthetic strand, the coupling chemistry can be incorporated during the chemical synthesis of the polynucleotide. For instance, the polynucleotide can be synthesized using a primer a reactive group attached to it.

A common technique for the amplification of sections of genomic DNA is using polymerase chain reaction (PCR). Here, using two synthetic oligonucleotide primers, a number of copies of the same section of DNA can be generated, where for each copy the 5' of each strand in the duplex will be a synthetic polynucleotide. By using an antisense primer that has a reactive group, such as a cholesterol, thiol, biotin or lipid, each copy of the target DNA amplified will contain a reactive group for coupling.

A transmembrane pore is a structure that crosses the membrane to some degree. It permits hydrated ions driven by an applied potential to flow across or within the membrane. The transmembrane pore typically crosses the entire membrane so that hydrated ions may flow from one side of the membrane to the other side of the membrane. However, the transmembrane pore does not have to cross the membrane. It may be closed at one end. For instance, the pore may be a well in the membrane along which or into which hydrated ions may flow.

Any transmembrane pore may be used in the invention. The pore may be biological or artificial. Suitable pores include, but are not limited to, protein pores and polynucleotide pores.

The transmembrane pore is preferably a transmembrane protein pore. A transmembrane protein pore is a polypeptide or a collection of polypeptides that permits hydrated ions, such as analyte, to flow across or within the membrane. In the present invention, the transmembrane protein pore is preferably capable of forming a pore that permits hydrated ions driven by an applied potential to flow from one side of the membrane to the other. The transmembrane protein pore permits analytes, such as nucleotides, to flow from one side of the membrane to the other. The transmembrane protein pore allows a polynucleotide, such as DNA or RNA, to be moved through the pore.

The transmembrane protein pore may be a monomer or an oligomer. The pore is preferably made up of several repeating subunits, such as 6, 7, 8 or 9 subunits. The pore is preferably a hexameric, heptameric, octameric or nonameric pore.

The transmembrane protein pore typically comprises a barrel or channel through which the ions may flow. The subunits of the pore typically surround a central axis and contribute strands to a transmembrane β barrel or channel or a transmembrane α-helix bundle or channel.

The barrel or channel of the transmembrane protein pore typically comprises amino acids that facilitate interaction with analyte, such as nucleotides, polynucleotides or nucleic acids. These amino acids are preferably located near a constriction of the barrel or channel. The transmembrane protein pore typically comprises one or more positively charged amino acids, such as arginine, lysine or histidine, or aromatic amino acids, such as tyrosine or tryptophan. These amino acids typically facilitate the interaction between the pore and nucleotides, polynucleotides or nucleic acids.

Transmembrane protein pores for use in accordance with the invention can be derived from β-barrel pores or α-helix bundle pores. β-barrel pores comprise a barrel or channel that is formed from β-strands. Suitable β-barrel pores include, but are not limited to, β-toxins, such as α-hemolysin, anthrax toxin and leukocidins, and outer membrane proteins/porins of bacteria, such as *Mycobacterium smegmatis* porin (Msp), for example MspA MspB, MspC or MspD, outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and αouter membrane proteins, such as WZA and ClyA toxin. The transmembrane pore may be derived from Msp or from α-hemolysin (α-HL).

The transmembrane protein pore is preferably derived from Msp, preferably from MspA. Such a pore will be oligomeric and typically comprises 7, 8, 9 or 10 monomers derived from Msp. The pore may be a homo-oligomeric pore derived from Msp comprising identical monomers. Alternatively, the pore may be a hetero-oligomeric pore derived from Msp comprising at least one monomer that differs from the others. Preferably the pore is derived from MspA or a homolog or paralog thereof.

A monomer derived from Msp typically comprises the sequence shown in SEQ ID NO: 2 or a variant thereof. SEQ ID NO: 2 is the MS-(B1)8 mutant of the MspA monomer. It includes the following mutations: D90N, D91N, D93N, D118R, D134R and E139K. A variant of SEQ ID NO: 2 is a polypeptide that has an amino acid sequence which varies from that of SEQ ID NO: 2 and which retains its ability to form a pore. The ability of a variant to form a pore can be assayed using any method known in the art. For instance, the variant may be inserted into an amphiphilic layer along with other appropriate subunits and its ability to oligomerise to form a pore may be determined. Methods are known in the art for inserting subunits into membranes, such as amphiphilic layers. For example, subunits may be suspended in a purified form in a solution containing a lipid bilayer such that it diffuses to the lipid bilayer and is inserted by binding to the lipid bilayer and assembling into a functional state. Alternatively, subunits may be directly inserted into the membrane using the "pick and place" method described in M. A. Holden, H. Bayley. J. Am. Chem. Soc. 2005, 127, 6502-6503 and International Application No. PCT/GB2006/001057 (published as WO 2006/100484).

Over the entire length of the amino acid sequence of SEQ ID NO: 2, a variant will preferably be at least 50% homologous to that sequence based on amino acid identity. More preferably, the variant may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 100 or more, for example 125, 150, 175 or 200 or more, contiguous amino acids ("hard homology").

Standard methods in the art may be used to determine homology. For example the UWGCG Package provides the BESTFIT program which can be used to calculate homology, for example used on its default settings (Devereux et at (1984) Nucleic Acids Research 12, p 387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et at (1990) J Mol Biol 215:403-10. Software for performing BLAST analyses is publicly available through the National Center for Biotechnology Information (http://www.ncbi.nlm.nih.gov/).

SEQ ID NO: 2 is the MS-(B1)8 mutant of the MspA monomer. The variant may comprise any of the mutations in the MspB, C or D monomers compared with MspA. The mature forms of MspB, C and D are shown in SEQ ID NOs: 5 to 7. In particular, the variant may comprise the following substitution present in MspB: A138P. The variant may comprise one or more of the following substitutions present in MspC: A96G, N102E and A138P. The variant may comprise one or more of the following mutations present in MspD: Deletion of G1, L2V, E5Q, L8V, D13G, W21A, D22E, K47T, I49H, I68V, D91G, A96Q, N102D, S103T, V104I, S136K and G141A. The variant may comprise combinations of one or more of the mutations and substitutions from Msp B, C and D. The variant preferably comprises the mutation L88N. A variant of SEQ ID NO: 2 has the mutation L88N in addition to all the mutations of MS-B1 and is called MS-(B2)8. The pore used in the invention is preferably MS-(B2)8. A variant of SEQ ID NO: 2 has the mutations G75S/G77S/L88N/Q126R in addition to all the mutations of MS-B1 and is called MS-B2C. The pore used in the invention is preferably MS-(B2)8 or MS-(B2C)8.

Amino acid substitutions may be made to the amino acid sequence of SEQ ID NO: 2 in addition to those discussed above, for example up to 1, 2, 3, 4, 5, 10, 20 or 30 substitutions. Conservative substitutions replace amino acids with other amino acids of similar chemical structure, similar chemical properties or similar side-chain volume. The amino acids introduced may have similar polarity, hydrophilicity, apolarity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table 2 below. Where amino acids have similar polarity, this can also be determined by reference to the hydropathy scale for amino acid side chains in Table 2.

TABLE 2

Chemical properties of amino acids

| | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

TABLE 3

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |

TABLE 3-continued

Hydropathy scale

| Side Chain | Hydropathy |
|---|---|
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

One or more amino acid residues of the amino acid sequence of SEQ ID NO: 2 may additionally be deleted from the polypeptides described above. Up to 1, 2, 3, 4, 5, 10, 20 or 30 residues may be deleted, or more.

Variants may include fragments of SEQ ID NO: 2. Such fragments retain pore forming activity. Fragments may be at least 50, 100, 150 or 200 amino acids in length. Such fragments may be used to produce the pores. A fragment preferably comprises the pore forming domain of SEQ ID NO: 2. Fragments must include one of residues 88, 90, 91, 105, 118 and 134 of SEQ ID NO: 2. Typically, fragments include all of residues 88, 90, 91, 105, 118 and 134 of SEQ ID NO: 2.

One or more amino acids may be alternatively or additionally added to the polypeptides described above. An extension may be provided at the amino terminal or carboxy terminal of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention. Other fusion proteins are discussed in more detail below.

As discussed above, a variant is a polypeptide that has an amino acid sequence which varies from that of SEQ ID NO: 2 and which retains its ability to form a pore. A variant typically contains the regions of SEQ ID NO: 2 that are responsible for pore formation. The pore forming ability of Msp, which contains a β-barrel, is provided by β-sheets in each subunit. A variant of SEQ ID NO: 2 typically comprises the regions in SEQ ID NO: 2 that form β-sheets. One or more modifications can be made to the regions of SEQ ID NO: 2 that form β-sheets as long as the resulting variant retains its ability to form a pore. A variant of SEQ ID NO: 2 preferably includes one or more modifications, such as substitutions, additions or deletions, within its α-helices and/or loop regions.

The monomers derived from Msp may be modified to assist their identification or purification, for example by the addition of histidine residues (a hist tag), aspartic acid residues (an asp tag), a streptavidin tag or a flag tag, or by the addition of a signal sequence to promote their secretion from a cell where the polypeptide does not naturally contain such a sequence. An alternative to introducing a genetic tag is to chemically react a tag onto a native or engineered position on the pore. An example of this would be to react a gel-shift reagent to a cysteine engineered on the outside of the pore. This has been demonstrated as a method for separating hemolysin hetero-oligomers (Chem Biol. 1997 July; 4(7):497-505).

The monomer derived from Msp may be labelled with a revealing label. The revealing label may be any suitable label which allows the pore to be detected. Suitable labels are described below.

The monomer derived from Msp may also be produced using D-amino acids. For instance, the monomer derived from Msp may comprise a mixture of L-amino acids and D-amino acids. This is conventional in the art for producing such proteins or peptides.

The monomer derived from Msp contains one or more specific modifications to facilitate nucleotide discrimination. The monomer derived from Msp may also contain other non-specific modifications as long as they do not interfere with pore formation. A number of non-specific side chain modifications are known in the art and may be made to the side chains of the monomer derived from Msp. Such modifications include, for example, reductive alkylation of amino acids by reaction with an aldehyde followed by reduction with $NaBH_4$, amidination with methylacetimidate or acylation with acetic anhydride.

The monomer derived from Msp can be produced using standard methods known in the art. The monomer derived from Msp may be made synthetically or by recombinant means. For example, the pore may be synthesized by in vitro translation and transcription (IVTT). Suitable methods for producing pores are discussed in International Application Nos. PCT/GB09/001690 (published as WO 2010/004273), PCT/GB09/001679 (published as WO 2010/004265) or PCT/GB10/000133 (published as WO 2010/086603). Methods for inserting pores into membranes are discussed above.

The transmembrane protein pore is also preferably derived from α-hemolysin (α-HL). The wild type α-HL pore is formed of seven identical monomers or subunits (i.e. it is heptameric). The sequence of one monomer or subunit of α-hemolysin-NN is shown in SEQ ID NO: 4. The transmembrane protein pore preferably comprises seven monomers each comprising the sequence shown in SEQ ID NO: 4 or a variant thereof. Amino acids 1, 7 to 21, 31 to 34, 45 to 51, 63 to 66, 72, 92 to 97, 104 to 111, 124 to 136, 149 to 153, 160 to 164, 173 to 206, 210 to 213, 217, 218, 223 to 228, 236 to 242, 262 to 265, 272 to 274, 287 to 290 and 294 of SEQ ID NO: 4 form loop regions. Residues 113 and 147 of SEQ ID NO: 4 form part of a constriction of the barrel or channel of α-HL.

In such embodiments, a pore comprising seven proteins or monomers each comprising the sequence shown in SEQ ID NO: 4 or a variant thereof are preferably used in the method of the invention. The seven proteins may be the same (homo-heptamer) or different (hetero-heptamer).

A variant of SEQ ID NO: 4 is a protein that has an amino acid sequence which varies from that of SEQ ID NO: 4 and which retains its pore forming ability. The ability of a variant to form a pore can be assayed using any method known in the art. For instance, the variant may be inserted into an amphiphilic layer, such as a lipid bilayer, along with other appropriate subunits and its ability to oligomerise to form a pore may be determined. Methods are known in the art for inserting subunits into amphiphilic layers, such as lipid bilayers. Suitable methods are discussed above.

The variant may include modifications that facilitate covalent attachment to or interaction with the construct. The variant preferably comprises one or more reactive cysteine residues that facilitate attachment to the construct. For instance, the variant may include a cysteine at one or more of positions 8, 9, 17, 18, 19, 44, 45, 50, 51, 237, 239 and 287 and/or on the amino or carboxy terminus of SEQ ID NO: 4. Preferred variants comprise a substitution of the residue at position 8, 9, 17, 237, 239 and 287 of SEQ ID NO: 4 with cysteine (A8C, T9C, N17C, K237C, S239C or E287C). The variant is preferably any one of the variants described in International Application No. PCT/GB09/001690 (published as WO 2010/004273), PCT/GB09/001679 (published as WO 2010/004265) or PCT/GB10/000133 (published as WO 2010/086603).

The variant may also include modifications that facilitate any interaction with nucleotides.

The variant may be a naturally occurring variant which is expressed naturally by an organism, for instance by a *Staphylococcus* bacterium. Alternatively, the variant may be expressed in vitro or recombinantly by a bacterium such as *Escherichia coli*. Variants also include non-naturally occurring variants produced by recombinant technology. Over the entire length of the amino acid sequence of SEQ ID NO: 4, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 4 over the entire sequence. There may be at least 80%, for example at least 85%, 90% or 95%, amino acid identity over a stretch of 200 or more, for example 230, 250, 270 or 280 or more, contiguous amino acids ("hard homology"). Homology can be determined as discussed above.

Amino acid substitutions may be made to the amino acid sequence of SEQ ID NO: 4 in addition to those discussed above, for example up to 1, 2, 3, 4, 5, 10, 20 or 30 substitutions. Conservative substitutions may be made as discussed above.

One or more amino acid residues of the amino acid sequence of SEQ ID NO: 4 may additionally be deleted from the polypeptides described above. Up to 1, 2, 3, 4, 5, 10, 20 or 30 residues may be deleted, or more.

Variants may be fragments of SEQ ID NO: 4. Such fragments retain pore-forming activity. Fragments may be at least 50, 100, 200 or 250 amino acids in length. A fragment preferably comprises the pore-forming domain of SEQ ID NO: 4. Fragments typically include residues 119, 121, 135. 113 and 139 of SEQ ID NO: 4.

One or more amino acids may be alternatively or additionally added to the polypeptides described above. An extension may be provided at the amino terminus or carboxy terminus of the amino acid sequence of SEQ ID NO: 4 or a variant or fragment thereof. The extension may be quite short, for example from 1 to 10 amino acids in length. Alternatively, the extension may be longer, for example up to 50 or 100 amino acids. A carrier protein may be fused to a pore or variant.

As discussed above, a variant of SEQ ID NO: 4 is a subunit that has an amino acid sequence which varies from that of SEQ ID NO: 4 and which retains its ability to form a pore. A variant typically contains the regions of SEQ ID NO: 4 that are responsible for pore formation. The pore forming ability of α-HL, which contains a β-barrel, is provided by β-strands in each subunit. A variant of SEQ ID NO: 4 typically comprises the regions in SEQ ID NO: 4 that form β-strands. The amino acids of SEQ ID NO: 4 that form β-strands are discussed above. One or more modifications can be made to the regions of SEQ ID NO: 4 that form β-strands as long as the resulting variant retains its ability to form a pore. Specific modifications that can be made to the β-strand regions of SEQ ID NO: 4 are discussed above.

A variant of SEQ ID NO: 4 preferably includes one or more modifications, such as substitutions, additions or deletions, within its α-helices and/or loop regions. Amino acids that form α-helices and loops are discussed above.

The variant may be modified to assist its identification or purification as discussed above.

Pores derived from α-HL can be made as discussed above with reference to pores derived from Msp.

In some embodiments, the transmembrane protein pore is chemically modified. The pore can be chemically modified in any way and at any site. The transmembrane protein pore is preferably chemically modified by attachment of a molecule to one or more cysteines (cysteine linkage), attachment of a molecule to one or more lysines, attachment of a molecule to one or more non-natural amino acids, enzyme modification of an epitope or modification of a terminus. Suitable methods for carrying out such modifications are well-known in the art. The transmembrane protein pore may be chemically modified by the attachment of any molecule. For instance, the pore may be chemically modified by attachment of a dye or a fluorophore.

Any number of the monomers in the pore may be chemically modified. One or more, such as 2, 3, 4, 5, 6, 7, 8, 9 or 10, of the monomers is preferably chemically modified as discussed above.

The reactivity of cysteine residues may be enhanced by modification of the adjacent residues. For instance, the basic groups of flanking arginine, histidine or lysine residues will change the pKa of the cysteines thiol group to that of the more reactive $S^-$ group. The reactivity of cysteine residues may be protected by thiol protective groups such as dTNB. These may be reacted with one or more cysteine residues of the pore before a linker is attached.

The molecule (with which the pore is chemically modified) may be attached directly to the pore or attached via a linker as disclosed in International Application Nos. PCT/GB09/001690 (published as WO 2010/004273), PCT/GB09/001679 (published as WO 2010/004265) or PCT/GB10/000133 (published as WO 2010/086603).

Any of the proteins described herein, such as the transmembrane protein pores, may be modified to assist their identification or purification, for example by the addition of histidine residues (a his tag), aspartic acid residues (an asp tag), a streptavidin tag, a flag tag, a SUMO tag, a GST tag or a MBP tag, or by the addition of a signal sequence to promote their secretion from a cell where the polypeptide does not naturally contain such a sequence. An alternative to introducing a genetic tag is to chemically react a tag onto a native or engineered position on the pore or construct. An example of this would be to react a gel-shift reagent to a cysteine engineered on the outside of the pore. This has been demonstrated as a method for separating hemolysin hetero-oligomers (Chem Biol. 1997 July; 4(7):497-505).

The pore may be labelled with a revealing label. The revealing label may be any suitable label which allows the pore to be detected. Suitable labels include, but are not limited to, fluorescent molecules, radioisotopes, e.g. $^{125}I$, $^{35}S$, enzymes, antibodies, antigens, polynucleotides and ligands such as biotin.

Any of the proteins described herein, such as the transmembrane protein pores, may be made synthetically or by recombinant means. For example, the pore may be synthesized by in vitro translation and transcription (IVTT). The amino acid sequence of the pore may be modified to include non-naturally occurring amino acids or to increase the stability of the protein. When a protein is produced by synthetic means, such amino acids may be introduced during production. The pore may also be altered following either synthetic or recombinant production.

The pore may also be produced using D-amino acids. For instance, the pore or construct may comprise a mixture of L-amino acids and D-amino acids. This is conventional in the art for producing such proteins or peptides.

The pore may also contain other non-specific modifications as long as they do not interfere with pore formation or construct function. A number of non-specific side chain modifications are known in the art and may be made to the side chains of the protein(s). Such modifications include, for example, reductive alkylation of amino acids by reaction with an aldehyde followed by reduction with $NaBH_4$, amidination with methylacetimidate or acylation with acetic anhydride.

Any of the proteins described herein, such as the transmembrane protein pores, can be produced using standard methods known in the art. Polynucleotide sequences encoding a pore or construct may be derived and replicated using standard methods in the art. Polynucleotide sequences encoding a pore or construct may be expressed in a bacterial host cell using standard techniques in the art. The pore may be produced in a cell by in situ expression of the polypeptide from a recombinant expression vector. The expression vector optionally carries an inducible promoter to control the expression of the polypeptide. These methods are described in Sambrook, J. and Russell, D. (2001). Molecular Cloning: A Laboratory Manual, 3rd Edition. Cold Spring Harbor Laboratory Press, Cold Spring Harbor, N.Y.

The pore may be produced in large scale following purification by any protein liquid chromatography system from protein producing organisms or after recombinant expression. Typical protein liquid chromatography systems include FPLC, AKTA systems, the Bio-Cad system, the Bio-Rad BioLogic system and the Gilson HPLC system.

The method is preferably for characterising a target polynucleotide and step (a) comprises contacting the target polynucleotide with the pore and a polynucleotide binding protein and the protein controls the movement of the target polynucleotide through the pore. The target polynucleotide may be contacted with the pore and the polynucleotide binding protein in any order. In is preferred that, when the target polynucleotide is contacted with the protein and the pore, the target polynucleotide firstly forms a complex with the protein. When the voltage is applied across the pore, the target polynucleotide/protein complex then forms a complex with the pore and controls the movement of the polynucleotide through the pore.

The polynucleotide binding protein may be any protein that is capable of binding to the polynucleotide and controlling its movement through the pore. It is straightforward in the art to determine whether or not a protein binds to a polynucleotide. The protein typically interacts with and modifies at least one property of the polynucleotide. The protein may modify the polynucleotide by cleaving it to form individual nucleotides or shorter chains of nucleotides, such as di- or trinucleotides. The moiety may modify the polynucleotide by orienting it or moving it to a specific position, i.e. controlling its movement.

The polynucleotide binding protein is preferably a polynucleotide handling enzyme. A polynucleotide handling enzyme is a polypeptide that is capable of interacting with and modifying at least one property of a polynucleotide. The enzyme may modify the polynucleotide by cleaving it to form individual nucleotides or shorter chains of nucleotides, such as di- or trinucleotides. The enzyme may modify the polynucleotide by orienting it or moving it to a specific position. The polynucleotide handling enzyme does not need to display enzymatic activity as long as it is capable of binding the target sequence and controlling its movement through the pore. For instance, the enzyme may be modified to remove its enzymatic activity or may be used under conditions which prevent it from acting as an enzyme. Such conditions are discussed in more detail below.

The polynucleotide handling enzyme is preferably derived from a nucleolytic enzyme. The polynucleotide handling enzyme used in the construct of the enzyme is more preferably derived from a member of any of the Enzyme Classification (EC) groups 3.1.11, 3.1.13, 3.1.14, 3.1.15, 3.1.16, 3.1.21, 3.1.22, 3.1.25, 3.1.26, 3.1.27, 3.1.30 and 3.1.31. The enzyme may be any of those disclosed in International Application No. PCT/GB10/000133 (published as WO 2010/086603).

Preferred enzymes are polymerases, exonucleases, helicases and topoisomerases, such as gyrases. Suitable enzymes include, but are not limited to, exonuclease I from *E. coli* (SEQ ID NO: 11), exonuclease III enzyme from *E. coli* (SEQ ID NO: 13), RecJ from *T. thermophilus* (SEQ ID NO: 15) and bacteriophage lambda exonuclease (SEQ ID NO: 17) and variants thereof. Three subunits comprising the sequence shown in SEQ ID NO: 15 or a variant thereof interact to form a trimer exonuclease. The enzyme is preferably Phi29 DNA polymerase (SEQ ID NO: 9) or a variant thereof. The topoisomerase is preferably a member of any of the Moiety Classification (EC) groups 5.99.1.2 and 5.99.1.3.

The enzyme is most preferably derived from a helicase, such as Hel308 Mbu (SEQ ID NO: 18), Hel308 Csy (SEQ ID NO: 19), Hel308 Tga (SEQ ID NO: 20); Hel308 Mhu (SEQ ID NO: 21), TraI Eco (SEQ ID NO: 22), XPD Mbu (SEQ ID NO: 23) or a variant thereof.

A variant of SEQ ID NOs: 9, 11, 13, 15, 17, 18, 19, 20, 21, 22 or 23 is an enzyme that has an amino acid sequence which varies from that of SEQ ID NO: 9, 11, 13, 15, 17, 18, 19, 20, 21, 22 or 23 and which retains polynucleotide binding ability. This can be measured using any method known in the art. For instance, the variant can be contacted with a polynucleotide and its ability to bind to and move along the polynucleotide can be measured. The variant may include modifications that facilitate binding of the polynucleotide and/or facilitate its activity at high salt concentrations and/or room temperature.

Over the entire length of the amino acid sequence of SEQ ID NO: 9, 11, 13, 15, 17, 18, 19, 20, 21, 22 or 23, a variant will preferably be at least 50% homologous to that sequence based on amino acid identity. More preferably, the variant polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 9, 11, 13, 15, 17, 18, 19, 20, 21, 22 or 23 over the entire sequence. There may be at least 80%, for example at least 85%, 90% or 95%, amino acid identity over a stretch of 200 or more, for example 230, 250, 270, 280, 300, 400, 500, 600, 700, 800, 900 or 1000 or more, contiguous amino acids ("hard homology"). Homology is determined as described above. The variant may differ from the wild-type sequence in any of the ways discussed above with reference to SEQ ID NO: 2 and 4 above. The enzyme may be covalently attached to the pore. Any method may be used to covalently attach the enzyme to the pore. There are two main strategies for sequencing polynucleotides using nanopores, namely strand sequencing and exonuclease sequencing. The method of the invention may concern either strand sequencing or exonuclease sequencing.

In strand sequencing, the DNA is translocated through the nanopore either with or against an applied potential. Exonucleases that act progressively or processively on double stranded DNA can be used on the cis side of the pore to feed the remaining single strand through under an applied potential or the trans side under a reverse potential. Likewise, a helicase that unwinds the double stranded DNA can also be used in a similar manner. A polymerase may also be used. There are also possibilities for sequencing applications that require strand translocation against an applied potential, but the DNA must be first "caught" by the enzyme under a reverse or no potential. With the potential then switched back following binding the strand will pass cis to trans through the pore and be held in an extended conformation by the current flow. The single strand DNA exonucleases or single strand DNA dependent polymerases can act as molecular motors to pull the recently translocated single strand back through the pore in a controlled stepwise manner, trans to cis, against the applied potential.

In one embodiment, the method of characterising a target polynucleotide involves contacting the target sequence with a pore and a helicase enzyme. Any helicase may be used in the method. Helicases may work in two modes with respect to the pore. First, the method is preferably carried out using a helicase such that it moves the target sequence through the pore with the field resulting from the applied voltage. In this mode the 5' end of the DNA is first captured in the pore, and the enzyme moves the DNA into the pore such that the target sequence is passed through the pore with the field until it finally translocates through to the trans side of the bilayer. Alternatively, the method is preferably carried out such that a helicase enzyme moves the target sequence through the pore against the field resulting from the applied voltage. In this mode the 3' end of the DNA is first captured in the pore, and the enzyme moves the DNA through the pore such that the target sequence is pulled out of the pore against the applied field until finally ejected back to the cis side of the bilayer.

In exonuclease sequencing, an exonuclease releases individual nucleotides from one end of the target polynucleotie and these individual nucleotides are identified as discussed below. In another embodiment, the method of characterising a target polynucleotide involves contacting the target sequence with a pore and an exonuclease enzyme. Any of the exonuclease enzymes discussed above may be used in the method. The enzyme may be covalently attached to the pore as discussed above.

Exonucleases are enzymes that typically latch onto one end of a polynucleotide and digest the sequence one nucleotide at a time from that end. The exonuclease can digest the polynucleotide in the 5' to 3' direction or 3' to 5' direction. The end of the polynucleotide to which the exonuclease binds is typically determined through the choice of enzyme used and/or using methods known in the art. Hydroxyl groups or cap structures at either end of the polynucleotide may typically be used to prevent or facilitate the binding of the exonuclease to a particular end of the polynucleotide.

The method involves contacting the polynucleotide with the exonuclease so that the nucleotides are digested from the end of the polynucleotide at a rate that allows characterisation or identification of a proportion of nucleotides as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The rate at which the exonuclease functions is typically slower than the optimal rate of a wild-type exonuclease. A suitable rate of activity of the exonuclease in the method of the invention involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of exonuclease activity can be achieved in various ways. For example, variant exonucleases with a reduced optimal rate of activity may be used in accordance with the invention.

The method of the invention involves measuring one or more characteristics of the target analyte, such as a target polynucleotide. The method may involve measuring two, three, four or five or more characteristics of the target analyte, such as a target polynucleotide. For target polynucleotides, the one or more characteristics are preferably selected from (i) the length of the target polynucleotide, (ii) the identity of the target polynucleotide, (iii) the sequence of the target polynucleotide, (iv) the secondary structure of the target polynucleotide and (v) whether or not the target polynucleotide is modified. Any combination of (i) to (v) may be measured in accordance with the invention.

For (i), the length of the polynucleotide may be measured using the number of interactions between the target polynucleotide and the pore.

For (ii), the identity of the polynucleotide may be measured in a number of ways. The identity of the polynucleotide may be measured in conjunction with measurement of the sequence of the target polynucleotide or without measurement of the sequence of the target polynucleotide. The former is straightforward; the polynucleotide is sequenced and thereby identified. The latter may be done in several ways. For instance, the presence of a particular motif in the polynucleotide may be measured (without measuring the remaining sequence of the polynucleotide). Alternatively, the measurement of a particular electrical and/or optical signal in the method may identify the target polynucleotide as coming from a particular source.

For (iii), the sequence of the polynucleotide can be determined as described previously. Suitable sequencing methods, particularly those using electrical measurements, are described in Stoddart D et al., Proc Natl Acad Sci, 12; 106(19):7702-7, Lieberman K R et al, J Am Chem Soc. 2010; 132(50):17961-72, and International Application WO 2000/28312.

For (iv), the secondary structure may be measured in a variety of ways. For instance, if the method involves an electrical measurement, the secondary structure may be measured using a change in dwell time or a change in current flowing through the pore. This allows regions of single-stranded and double-stranded polynucleotide to be distinguished.

For (v), the presence or absence of any modification may be measured. The method preferably comprises determining whether or not the target polynucleotide is modified by methylation, by oxidation, by damage, with one or more proteins or with one or more labels, tags or spacers. Specific modifications will result in specific interactions with the pore which can be measured using the methods described below. For instance, methylcyotsine may be distinguished from cytosine on the basis of the current flowing through the pore during its interation with each nucleotide.

The invention also provides a method of estimating the sequence of a target polynucleotide. The invention further provides a method of sequencing a target polynucleotide.

A variety of different types of measurements may be made. This includes without limitation: electrical measurements and optical measurements. Possible electrical measurements include: current measurements, impedance measurements, tunnelling measurements (Ivanov A P et al., Nano Lett. 2011 Jan. 12; 11(1):279-85), and FET measurements (International Application WO 2005/124888). Optical measurements may be combined 10 with electrical measurements (Soni G V et al., Rev Sci Instrum. 2010 Jan; 81(1): 014301). The measurement may be a transmembrane current measurement such as measurement of ionic current flowing through the pore.

Electrical measurements may be made using standard single channel recording equipment as describe in Stoddart D et al., Proc Natl Acad Sci, 12; 106(19):7702-7, Lieberman K R et al, J Am Chem Soc. 2010; 132(50):17961-72, and International Application WO-2000/28312. Alternatively, electrical measurements may be made using a multi-channel system, for example as described in International Application WO-2009/077734 and International Application WO-2011/067559.

In a preferred embodiment, step (b) comprises measuring the current passing through the pore as the analyte moves with respect to the pore wherein the current is indicative of one or more characteristics of the target analyte and thereby characterising the target analyte. In a more preferred embodiment, the target analyte is a target polynucleotide and the method comprises (a) contacting the target polynucleotide with a transmembrane pore present in a membrane of the system of the invention and a polynucleotide binding protein such that the protein controls the movement of the target polynucleotide through the pore and (b) measuring the current passing through the pore as the polynucleotide moves with respect to the pore wherein the current is indicative of one or more characteristics of the target polynucleotide and thereby characterising the target polynucleotide.

The methods may be carried out using any apparatus that is suitable for investigating a membrane/pore system in which a pore is inserted into a membrane of the system of the invention.

The methods may involve measuring the current passing through the pore as the analyte, such as a target polynucleotide, moves with respect to the pore. Therefore the apparatus may also comprise an electrical circuit capable of applying a potential and measuring an electrical signal across the membrane and pore. The methods may be carried out using a patch clamp or a voltage clamp. The methods preferably involve the use of a voltage clamp.

The methods of the invention may involve the measuring of a current passing through the pore as the analyte, such as a target polynucleotide, moves with respect to the pore. Suitable conditions for measuring ionic currents through transmembrane protein pores are known in the art and disclosed in the Example. The method is typically carried out with a voltage applied across the membrane and pore. The voltage used is typically from +2 V to −2 V, typically −400 mV to +400 mV. The voltage used is preferably in a range having a lower limit selected from −400 mV, −300 mV, −200 mV, −150 mV, −100 mV, −50 mV, −20 mV and 0 mV and an upper limit independently selected from +10 mV, +20 mV, +50 mV, +100 mV, +150 mV, +200 mV, +300 mV and +400 mV. The voltage used is more preferably in the range 100 mV to 240 mV and most preferably in the range of 120 mV to 220 mV. It is possible to increase discrimination between different nucleotides by a pore by using an increased applied potential.

The methods are typically carried out in the presence of any charge carriers, such as metal salts, for example alkali metal salt, halide salts, for example chloride salts, such as alkali metal chloride salt. Charge carriers may include ionic liquids or organic salts, for example tetramethyl ammonium chloride, trimethylphenyl ammonium chloride, phenyltrimethyl ammonium chloride, or 1-ethyl-3-methyl imidazolium chloride. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration may be at saturation. The salt concentration may be 3M or lower and is typically from 0.1 to 2.5 M, from 0.3 to 1.9 M, from 0.5 to 1.8 M, from 0.7 to 1.7 M, from 0.9 to 1.6 M or from 1 M to 1.4 M. The salt concentration is preferably from 150 mM to 1 M. The method is preferably carried out using a salt concentration of at least 0.3 M, such as at least 0.4 M, at least 0.5 M, at least 0.6 M, at least 0.8 M, at least 1.0 M, at least 1.5 M, at least 2.0 M, at least 2.5 M or at least 3.0 M. High salt concentrations provide a high signal to noise ratio and allow for currents indicative of the presence of a nucleotide to be identified against the background of normal current fluctuations.

The methods are typically carried out in the presence of a buffer. In the exemplary apparatus discussed above, the buffer is present in the aqueous solution in the chamber. Any buffer may be used in the method of the invention. Typically, the buffer is HEPES. Another suitable buffer is Tris-HCl buffer. The methods are typically carried out at a pH of from 4.0 to 12.0, from 4.5 to 10.0, from 5.0 to 9.0, from 5.5 to 8.8, from 6.0 to 8.7 or from 7.0 to 8.8 or 7.5 to 8.5. The pH used is preferably about 7.5.

The methods may be carried out at from 0° C. to 100° C., from 15° C. to 95° C., from 16° C. to 90° C., from 17° C. to 85° C., from 18° C. to 80° C., 19° C. to 70° C., or from 20° C. to 60° C. The methods are typically carried out at room temperature. The methods are optionally carried out at a temperature that supports enzyme function, such as about 37° C.

The method is typically carried out in the presence of free nucleotides or free nucleotide analogues and an enzyme cofactor that facilitate the action of the polynucleotide binding protein, such as a helicase or an exonuclease. The free nucleotides may be one or more of any of the individual nucleotides discussed above. The free nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The free nucleotides are preferably selected from AMP, TMP, GMP, CMP, UMP, dAMP, dTMP, dGMP or dCMP. The free nucleotides are preferably adenosine triphosphate (ATP). The enzyme cofactor is a factor that allows the helicase to function. The enzyme cofactor is preferably a divalent metal cation. The divalent metal cation is preferably $Mg^{2+}$, $Mn^{2+}$, $Ca^{2+}$ or $Co^{2+}$. The enzyme cofactor is most preferably $Mg^{2+}$.

Methods of Forming Sensors

The invention also provides a method of forming a sensor for characterising a target polynucleotide. The method comprises forming a complex between (a) a pore present in a membrane of the system of the invention and (b) a polynucleotide binding protein, such as a helicase or an exonuclease. The complex may be formed by contacting the pore and the protein in the presence of the target polynucleotide and then applying a potential across the pore. The applied potential may be a chemical potential or a voltage potential as described above. Alternatively, the complex may be formed by covalently attaching the pore to the protein. Methods for covalent attachment are known in the art and disclosed, for example, in International Application Nos. PCT/GB09/001679 (published as WO 2010/004265) and PCT/GB10/000133 (published as WO 2010/086603). The complex is a sensor for characterising the target polynucleotide. The method preferably comprises forming a complex between the pore and a helicase. Any of the embodiments discussed above equally apply to this method.

The invention also provides a sensor for characterising a target polynucleotide. The sensor comprises a complex between (a) a pore present in a membrane of the system of the invention and (b) a polynucleotide binding protein. Any of the embodiments discussed above equally apply to the sensor of the invention.

Kits

The present invention also provides a kit for characterising, such as sequencing, a target polynucleotide. The kit comprises (a) a pore present in a membrane of the system of the invention and (b) a polynucleotide binding protein, such as a helicase or an exonuclease. Any of the embodiments discussed above equally applicable to the kits of the invention.

The kits of the invention may additionally comprise one or more other reagents or instruments which enable any of the embodiments mentioned above to be carried out. Such reagents or instruments include one or more of the following: suitable buffer(s) (aqueous solutions), means to obtain a sample from a subject (such as a vessel or an instrument comprising a needle), means to amplify and/or express polynucleotide sequences or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

Apparatus

The invention also provides an apparatus for characterising, such as sequencing, target polynucleotides in a sample. The apparatus may comprise (a) a plurality of pores present in a plurality of membranes of one or more systems of the invention and (b) a plurality of polynucleotide binding proteins, such as helicases or exonucleases. The apparatus may be any conventional apparatus for analyte analysis, such as an array or a chip.

The apparatus preferably comprises:
a sensor device that is capable of supporting the plurality of pores and membranes and being operable to perform polynucleotide characterising or sequencing using the pores and proteins;
at least one reservoir for holding material for performing the characterising or sequencing;
a fluidics system configured to controllably supply material from the at least one reservoir to the sensor device; and
a plurality of containers for receiving respective samples, the fluidics system being configured to supply the samples selectively from the containers to the sensor device.

The apparatus may be any of those described in International Application No. PCT/GB10/000789 (published as WO 2010/122293), International Application No. PCT/GB10/002206 (not yet published) or International Application No. PCT/US99/25679 (published as WO 00/28312).

The invention will be further described in the Examples which follow.

EXAMPLES

Example 1

This example describes the method used to produce the triblock co-polymer droplets which are used to fill the interconnecting compartments on the microfluidic chips.
Materials and Methods
The T-junction chips are prepared for droplet generation by affixing nanoport assemblies (Upchurch Scientific) as fluidic interfaces.

The droplet generation mechanism in a T-junction is well documented in the literature [Garstecki et al., Lab Chip, 2006, 6, 437-446 and Thorsen et al., Physical Reviw Letters, 86, 18, 4163-4166]. Taking into account the fluid viscosities of the reagents involved the chosen T-junction geometry was 50 μm channel width for both cases (oil and buffer).
1.1—Droplet Reagents
In order to make aqueous phase droplets in oil, buffer is used as the disperse phase, while a silicon oil (e.g. AR20), is used as the continuous phase. Both buffer and triblock co-polymer-containing oil are prepared as described below.

A solution of buffer (buffer 1) was prepared by adding 298 mg of KCl (99.99% Purity, Sigma) to 10 mL of degassed DI water. To this solution 30.35 mg of 2-Amino-2-(hydroxymethyl)-1,3-propanediol (99.9%, Sigma) was added. The solution was buffered to pH 8 using small quantities of HCl and NaOH. 316.5 mg of $K_2[Fe(CN)_6]$ (99.9%, Sigma) and 82.3 mg of $K_3[Fe(CN)_6]$ (99.9%, Sigma) was added to the solution and stirred until dissolved.

Oil-triblock co-polymer solution was prepared by adding 20 mg of polymer (6-33-6, PMOXA-PDMS-PMOXA, PolymerSource) to 1 mL of AR20 (99%, Sigma). The polymer was left stirring in the oil for 24 hrs until all of the polymer had dissolved.
1.2—Droplet Generation Setup
A schematic for the droplet generation setup can be seen in FIG. 1. This setup consists of two syringe pumps (Elite, Harvard Apparatus), two gastight syringes (Hamilton), peak tubing (Upchurch Scientific), and a custom made T-junction microfluidic chip. Once the syringes are loaded with oil and buffer and mounted on the syringe pumps, the peak tubing is used to establish the fluidic connections to the ports on the chip. The oil syringe should be connected to the continuous phase channel input while the buffer should be connected to the disperse phase channel input.

Both syringe pumps were set to infuse at a flow rate of 10 μL/min, which produced an average droplet size (diameter) of 129.46 with a standard deviation of 10.87 The droplets were then collected in a vial.

Example 2

Figure 2:
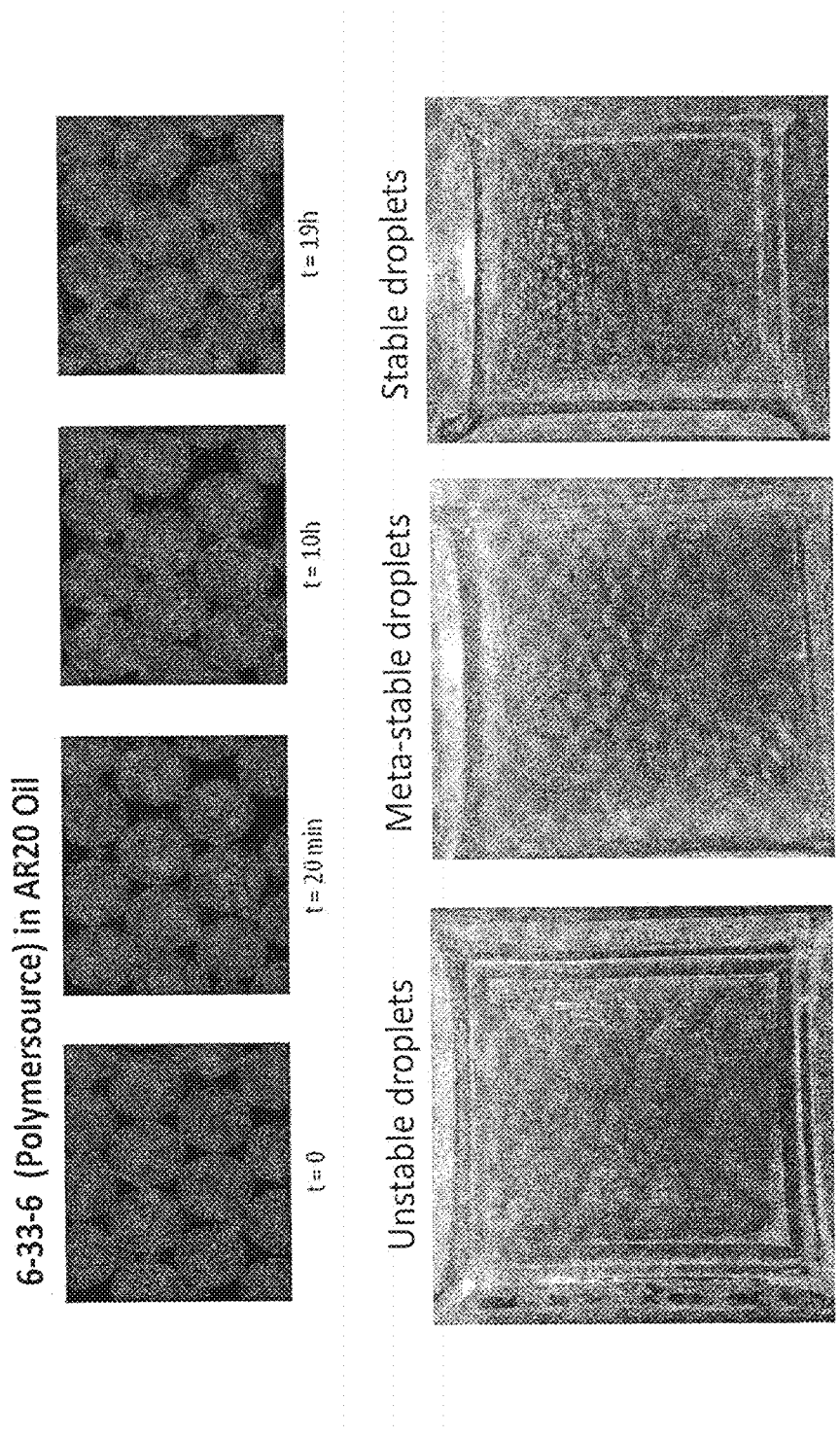
FIG. 2 shows droplet stability experiments. A) shows the stability of the 6-33-6 Polymersource droplets in AR20 oil changed over time. After 20 hours these droplets were found to have not merged. B) shows examples of unstable, metastable and stable droplets for illustrative purposes.
Figure 3:
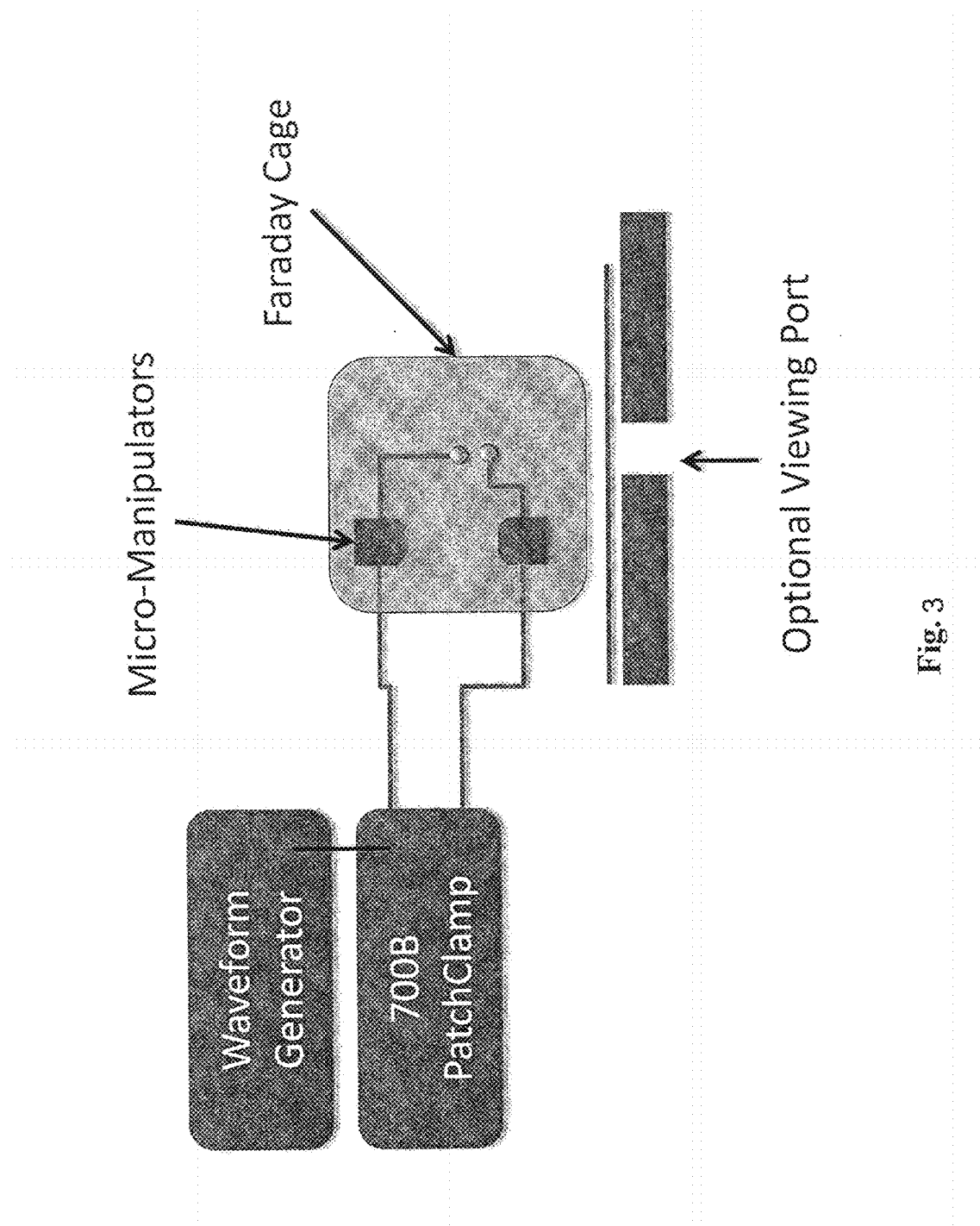
FIG. 3 shows the experimental set-up for the droplet-interface-bilayer experiments.

This example describes the method used to produce droplet-interface-bilayers (DIBs) using a number of different tri-block co-polymers in different oils (experimental set-up shown in FIG. 3). The ability to form bilayers and to allow insertion of biological nanopores (such as mutants of MspA) was also investigated.
Materials and Methods
Experiments 2.1, 2.3 and 2.4 were carried out on the below combinations of tri-block co-polymer and oil.
1—6-33-6 (PMOXA-PDMS-PMOXA) PolymerSource (20 mg/mL) in AR20 oil (polyphenyl-methylsiloxane, Sigma Aldrich).
2—6-33-6 (PMOXA-PDMS-PMOXA) PolymerSource (20 mg/mL) in PDMS-OH 65cSt oil (poly(dimethylsiloxane), hydroxyl terminated, Sigma Aldrich).
3—6-45PE-6 (PMOXA-PE-PMOXA, where PE=a polyethylene hydrocarbon chain approximately 45 carbon atoms in length.) PolymerSource (20 mg/mL) in hexadecane (99.9%, Sigma Aldrich).
4—6-32-6 (PMOXA-PDMS-PMOXA) HighForce (20 mg/mL) in AR20 oil (polyphenyl-methylsiloxane, Sigma Aldrich).
2.1—Droplet Stability Experiments
Droplet stability was measured off-line by preparing solutions of buffer and triblock ABA polymer in various oils. A small 0.5 $cm^2$ tray was prepared using polycarbonate and a glass slide (FIG. 2). The tray was filled with oil. To the oil, 1 μL buffer droplets were added and monitored over 24 hrs. Droplets that exhibited only a small degree of merging were progressed to electrical DIBs testing.
2.2—Experimental Set-up
The experimental apparatus was set-up as shown in FIG. 3. A 700B axopatch was connected inside a shielded box containing two micro-manipulators. The entire faraday cage was placed on an inverted microscope (Nikon) such that it was possible to view the manipulation of the droplets from underneath. This allowed the droplets to be moved without opening the Faraday cage.

Within the Faraday cage, the electrodes of the 700B axopatch were connected via pure gold (Au) wire The Au was prepared for use in the droplet setup by flaming the end such that the wire formed a small gold bead. The Au wire was cleaned by emersion in conc.$HNO_3$ for 30 s, and washed thoroughly with DI water. The ball-ended wire was then repeatedly moved through a liquid agarose solution prepared from the buffer (5% wt low-melt agarose, Lonza/Buffer 400 mM KCl, 75 mM $K_2[Fe(CN)_6]$ (99.9%, Sigma) and 25 mM $K_3[Fe(CN)_6]$ (99.9%, Sigma), 10 mM Tris). Once a small bead had formed on the end the agarose was allowed to cool, and the wire was stored in an excess of buffer solution in order to come to equilibrium.

The droplet chamber was mounted on the stage within the Faraday cage, and the electrodes were mounted such that both fell within the central section of the chamber. The manipulators were situated such that a full range of movement in X and Y directions were achievable by both electrodes over the area of the chamber. The chamber was then filled to the brim with the AR20 tri-block co-polymer solution and allowed to stand for a few minutes. 1 μL of buffer was pipetted directly onto each of the agarose tipped Au wires and both electrodes were moved directly under the AR20/triblock co-polymer solution. The droplets were left under the solution for 30 s before movement.

2.3—Membrane Formation

To form a membrane with the droplet pair, a waveform of ±20 mV was applied to the electrodes in addition to a bias voltage of 180 mV. The current response was monitored as the indicator of the formation of a capacitive membrane (see FIG. 5 for a sample trace showing the increase in capacitance over time). The droplets were carefully brought together such that contact between the two buffer volumes was made (see FIG. 4 (B)). The droplets were left in this state until a membrane was formed (see FIG. 5). In situations where the membrane growth was very slow, the droplets were moved in the XY direction, which forced exclusion of the AR20/triblock co-polymer between the droplets and facilitated membrane growth.

2.4—Nanopore Insertion Experiments

In order to insert trans-membrane pores across the membrane, a 0.0005 mg/ml solution of MspA-(B2C) (SEQ ID NO: 25, which is a variant of SEQ ID NO: 2 with the following mutations G75S/G77S/L88N/Q126R) was added to the buffer that formed the anolyte. Insertion of the pore was observed by an instantaneous increase in current (See FIG. 6). This was performed in the absence of the waveform, but under the applied bias potential.

Results

The different tri-block co-polymer and oil combinations that were investigated are shown in table 4 below.

TABLE 4

| Tri-Block Co-Polymer | Oil | Off-line Stability Test | Membrane Formation | MspA-(B2C) Pore Insertion |
|---|---|---|---|---|
| 6-33-6 PolymerSource | AR20 | stable droplets formed | capacitive membrane growth observed | pores inserted |
| 6-33-6 PolymerSource | PDMS-OH 65 cSt | stable droplets formed | capacitive membrane growth observed | pores inserted |
| 6-45PE-6 PolymerSource | C16 | stable droplets formed | capacitive membrane growth observed | pores inserted |
| 6-32-6 HighForce | AR20 | stable droplets formed | capacitive membrane growth observed | pores inserted |

Figure 6:
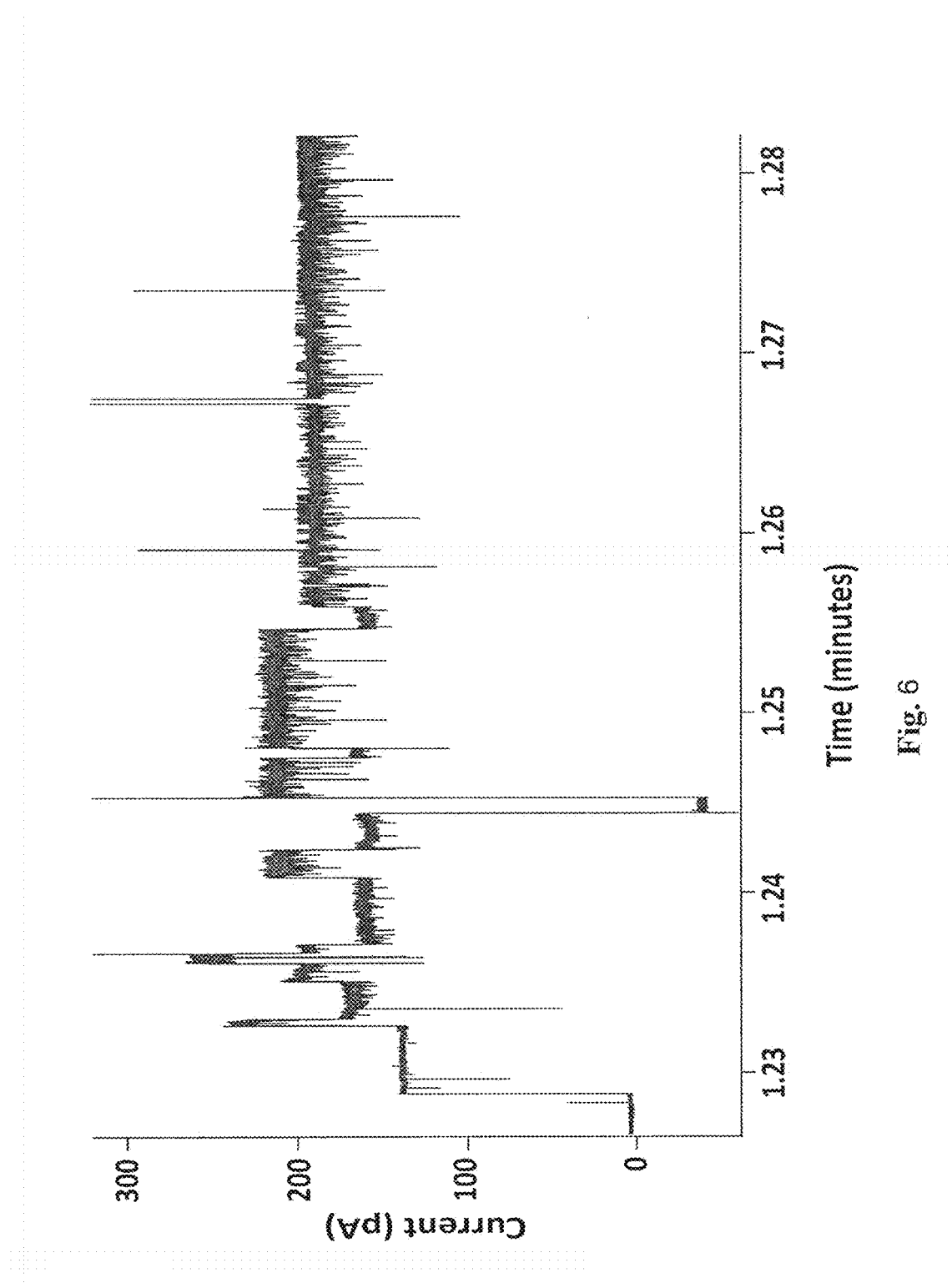
FIG. 6 shows an example electrical trace illustrating how a sharp current increase was observed when MspA-(B2C) (SEQ ID NO: 25, which is a variant of SEQ ID NO: 2 with the following mutations G75S/G77S/L88N/Q126R) inserted into 6-33-6 Polymersource tri-block co-polymer droplets in AR20 oil. Instances where pores have inserted into the tri-block are indicated by black arrows.

Capacitive membrane growth and pore insertion was observed for all of the tri-block co-polymer/oils tested. FIGS. 5 and 6 show membrane growth and MspA-(B2C) (SEQ ID NO: 25, which is a variant of SEQ ID NO: 2 with the following mutations G75S/G77S/L88N/Q126R) pore insertion for the 6-33-6 PolymerSource tri-block co-polymer used with AR20 silicone oil. FIG. 7 shows membrane growth and pore insertion for the 6-45PE-6 PolymerSource used with hexadecane as an example of a triblock co-polymer which does not have the PMOXA central core structure.

The Oxford Nanopore Technologies Limited reference for this application is ONT IP 039.

The invention claimed is:

1. A method of forming a membrane between a first volume of polar medium and a second volume of polar medium, which method comprises:
   providing a first volume comprising polar medium and a second volume comprising polar medium which are separated from one another by an apolar medium,
   wherein at least one of the first and second volumes comprises a layer comprising amphipathic molecules at an interface between the polar medium and the apolar medium,
   wherein each of the amphipathic molecules comprises a first outer hydrophilic group, a hydrophobic core group, and a second outer hydrophilic group, wherein the first and second outer hydrophilic groups are linked to opposite ends of the hydrophobic core group, and
   wherein the contact between the first and second volumes of polar medium allows the apolar medium located between the first and second volumes to become displaced and a membrane to form comprising the amphipathic molecules located between the first and second volumes of polar medium.

2. A method according to claim 1 wherein each of the first and second volumes comprises a layer comprising the amphipathic molecules at the interface between the polar medium and the apolar medium.

3. A method according to claim 1 wherein the first and second outer hydrophilic groups are independently linked to different atoms of the hydrophobic core group.

4. A method according to claim 1 wherein each of the amphipathic molecules further comprises at least one additional hydrophobic or hydrophilic group.

5. A method according to claim 4 wherein each of the amphipathic molecules further comprises at least one additional hydrophobic group which is bonded to the first outer hydrophilic group or the second outer hydrophilic group.

6. A method according to claim 5 wherein each of the amphipathic molecules further comprises: a first additional hydrophobic group which is bonded to the first outer hydrophilic group, and a second additional hydrophobic group which is bonded to the second outer hydrophilic group.

7. A method according to claim 5 wherein each additional hydrophobic group is capable of aligning itself with the hydrophobic core group.

8. A method according to claim 1 wherein each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$.

9. A method according to claim 8 wherein the copolymer has a linear or graft structure, and wherein the first and second outer hydrophilic polymer segments, $A_1$ and $A_2$, are pendant from the inner hydrophobic polymer segment, B.

10. A method according to claim 8 wherein the first and second outer hydrophilic polymer segments, $A_1$ and $A_2$, are linked to opposite ends of the inner hydrophobic polymer segment, B.

11. A method according to claim 8 wherein the copolymer further comprises one or more additional polymer segments.

12. A method according to claim 11 wherein the or each additional polymer segment is the same or different and is an additional hydrophilic polymer segment or an additional hydrophobic polymer segment.

13. A method according to claim 8 wherein the first outer hydrophilic polymer segment $A_1$, the second outer hydrophilic polymer segment $A_2$, or both $A_1$ and $A_2$, are bonded to one or more additional polymer segments, and/or wherein the inner hydrophobic polymer segment B is bonded to the first outer hydrophilic polymer segment $A_1$, the second outer hydrophilic polymer segment $A_2$, or both $A_1$ and $A_2$, directly, or via one or more additional polymer segments.

14. A method according to claim 8 wherein the copolymer is a block copolymer of formula (I)

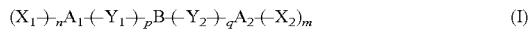
(I)

wherein:
$A_1$ is said first outer hydrophilic polymer segment;
B is said inner hydrophobic polymer segment;
$A_2$ is said second outer hydrophilic polymer segment;
$X_1$, $Y_1$, $Y_2$ and $X_2$ are additional polymer segments; and n, p, q and m are independently either 0 or 1.

15. A method according to claim 14 wherein $X_1$ and $X_2$ are both additional hydrophilic polymer segments or are both additional hydrophobic polymer segments, and wherein $Y_1$ and $Y_2$ are both additional hydrophobic polymer segments or are both additional hydrophilic polymer segments.

16. A method according to claim 14 wherein m and n are both 1, p and q are both 0, and the copolymer is a pentablock copolymer.

17. A method according to claim 16 wherein $X_1$ and $X_2$ are both additional hydrophobic polymer segments and are capable of aligning themselves with the inner hydrophobic polymer segment B.

18. A method according to claim 16 wherein the copolymer is a pentablock copolymer of formula (II):

(II)

wherein:
$A_1$ is said first outer hydrophilic polymer segment;
B is said inner hydrophobic polymer segment;
$A_2$ is said second outer hydrophilic polymer segment;
$B_1$ is a first additional hydrophobic polymer segment; and
$B_2$ is a second additional hydrophobic polymer segment.

19. A method according to claim 14 wherein m, n, p and q are 0, and the copolymer is a triblock copolymer of formula (III)

(III)

wherein
$A_1$ is said first outer hydrophilic polymer segment;
B is said inner hydrophobic polymer segment;
$A_2$ is said second outer hydrophilic polymer segment.

20. A method according to claim 8 wherein the copolymer is a triblock copolymer having a middle polymer segment which is said inner hydrophobic polymer segment B, and two outer polymer segments which are said first and second outer hydrophilic polymer segments, $A_1$ and $A_2$.

21. A method according to claim 8, wherein the inner hydrophobic polymer segment B and, when present, one or more additional hydrophobic polymer segments, which may be the same or different, comprise a polymer of a monomer selected from: $C_1$-$C_{18}$ alkyl and $C_3$-$C_{18}$ cycloalkyl acrylates and methacrylates, $C_3$-$C_{18}$ alkylacrylamides and methacrylamides, acrylonitrile, methacrylonitrile, vinyl $C_1$-$C_{18}$ alkanoates, $C_2$-$C_{18}$ alkenes, $C_2$-$C_{18}$ haloalkenes, styrene, ($C_{1-6}$ alkyl)styrene, $C_4$-$C_{12}$ alkyl vinyl ethers, $C_2$-$C_{10}$ perfluoro-alkyl acrylates and methacrylates and correspondingly partially fluorinated acrylates and methacrylates, $C_3$-$C_{12}$ perfluoroalkylethylthiocarbonylaminoethyl acrylates and methacrylates, acryloxy- and methacryloxyalkylsiloxanes, N-vinylcarbazole, $C_1$-$C_{12}$ alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobomyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane.

22. A method according to claim 8, wherein the inner hydrophobic polymer segment B and, when present, one or more additional hydrophobic polymer segments, which may be the same or different, comprise a polymer selected from polysiloxane, polyalkene, perfluoropolyether, perfluoroalkyl polyether, polystyrene, polyoxypropylene, polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, poly(propylene oxide) and copolymers thereof.

23. A method according to claim 8, wherein the inner hydrophobic polymer segment B and, when present, one or more additional hydrophobic polymer segments, which may be the same or different, comprises an unsaturated polymer selected from: a polymer of a conjugated aliphatic or alicyclic diene, which diene is unsubstituted or substituted by halogen or $C_1$-$C_6$ alkyl; a polymer of an alkyne or dialkyne, which alkyne or dialkyne is unsubstituted or substituted by $C_1$-$C_6$ alkyl or trimethylsilyl; a copolymer of a conjugated diene and a hydrophilic or hydrophobic vinylic monomer; and partially hydrated derivatives thereof.

24. A method according to claim 23 wherein the unsaturated polymer is: cis-, trans-, iso- or syndiotactic poly-1,2-butadiene, poly-1,4-butadiene or polyisoprene, poly-pentenamer, polychloroprene or polypiperylen; butadiene- or isoprene-copolymers with hydrophilic or hydrophobic vinylic monomers selected from acrylonitrile, styrene, acrylic acid, or hydroxyethylmethacrylate; or poly-1-trimethylsilyl-propyne.

25. A method according to claim 8, wherein the inner hydrophobic polymer segment B and, when present, one or more additional hydrophobic polymer segments comprise a polysiloxane or a polyalkene.

26. A method according to claim 25 wherein the polysiloxane is polydimethylsiloxane or polydiphenylsiloxane, and wherein the polyalkene is polyethylene.

27. A method according to claim 8 wherein the inner hydrophobic polymer segment B comprises a polysiloxane block having terminal alkylene groups.

28. A method according to claim 8, wherein the molecular weight of each of the inner hydrophobic polymer segment B and, when present, one or more additional hydrophobic polymer segments is from 150 to 50,000.

29. A method according to claim 8, wherein the first outer hydrophilic polymer segment $A_1$, the second outer hydrophilic polymer segment $A_2$ and, when present, one or more additional hydrophilic polymer segments, which may be the same or different, comprise a polymer of a monomer selected from: hydroxyl-substituted $C_1$-$C_6$ alkyl acrylates and methacrylates, acrylamide, methacrylamide, ($C_1$-$C_6$ alkyl) acrylamides and methacrylamides, N,N-dialkyl-acrylamides, ethoxylated acrylates and methacrylates, polyethyleneglycol-mono methacrylates and polyethyleneglycol-monomethylether methacrylates, hydroxyl-substituted ($C_1$-$C_6$ alkyl)acrylamides and methacrylamides, hydroxyl-substituted $C_1$-$C_6$ alkyl vinyl ethers, sodium vinylsulfonate, sodium styrenesulfonate, 2-acrylamido-2-methylpropane-sulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino($C_1$-$C_6$ alkyl)-, mono($C_1$-$C_6$ alkylamino)($C_1$-$C_6$ alkyl) and di($C_1$-$C_6$ alkylamino)($C_1$-$C_6$ alkyl) acrylates and methacrylates, allyl alcohol, 3-trimethylammonium 2-hydroxypropylmethacrylate chloride, dimethylaminoethyl methacrylate (DMAEMA), dimethylaminoethylmethacrylamide, glycerol methacrylate, N-(1,1-dimethyl-3-oxobutyl)acrylamide, cyclic imino ethers, vinyl ethers, cyclic ethers including epoxides, cyclic unsaturated ethers, N-substituted aziridines, [beta]-lactones and [beta]-lactames, ketene acetals, vinyl acetals and phosphoranes.

30. A method according to claim 8, wherein the first outer hydrophilic polymer segment $A_1$, the second outer hydrophilic polymer segment $A_2$ and, when present, one or more additional hydrophilic polymer segments, which may be the same or different, comprise a polymer of a monomer selected from: a cyclic imino ether selected from 2-methyloxazoline, 2-oxazoline, and 2-oxazoline having an alkenyl group in the 2 position, and a vinyl ether selected from methyl vinyl ether, ethyl vinyl ether and methoxy ethyl vinyl ether.

31. A method according to claim 8, wherein the first outer hydrophilic polymer segment $A_1$, the second outer hydrophilic polymer segment $A_2$ and, when present, one or more additional hydrophilic polymer segments, which may be the same or different, comprise a polymer selected from polyoxazoline, polyethylene glycol, polyethylene oxide, polyvinyl alcohol, polyvinylpyrrolidone, polyacrylamide, poly (meth)acrylic acid, polyethylene oxide-co-polypropyleneoxide block copolymers, poly (vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more thereof, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

32. A method according to claim 8, wherein the first outer hydrophilic polymer segment $A_1$, the second outer hydrophilic polymer segment $A_2$ and, when present, one or more additional hydrophilic polymer segments, which may be the same or different, comprise poly(2-methyloxazoline).

33. A method according to claim 8, wherein the molecular weight of each of the first outer hydrophilic polymer segment $A_1$, the second outer hydrophilic polymer segment $A_2$ and, when present, one or more additional hydrophilic polymer segments, is from 150 to 50,000.

34. A method according to claim 1 wherein each of the amphipathic molecules is a bipolar lipid, comprising two hydrophilic head groups bonded to opposite ends of a hydrophobic tail group, wherein each hydrophilic head group is optionally bonded to at least one further hydrophobic tail group.

35. A method according to claim 34 wherein the bipolar lipid is a bipolar phospholipid.

36. A method according to claim 1 wherein the amphipathic molecules are poly(2-methyloxazoline)-block-poly(dimethylsiloxane)-block-poly(2-methyloxazoline) (PMOXA-PDMS-PMOXA).

37. A method according to claim 1 wherein the membrane which is formed between the volumes of polar medium comprises a monolayer of the amphipathic molecules.

38. A method according to claim 1 wherein the membrane which is formed between the volumes of polar medium comprises first and second outer hydrophilic layers formed by the first and second outer hydrophilic groups of the amphipathic molecules, and a middle hydrophobic layer formed by the hydrophobic core group of the amphipathic molecules, wherein said first and second outer hydrophilic layers contact the volumes of polar medium on either side of the membrane.

39. A method according to claim 1 wherein the step of providing a first volume comprising polar medium and a second volume comprising polar medium which are separated from one another by an apolar medium, comprises:
(i) contacting a first volume comprising polar medium with the apolar medium;
(ii) either before or after step (i), providing the amphipathic molecules in the apolar medium and/or in the first volume of polar medium;
(iii) leaving the first volume comprising polar medium in contact with the apolar medium for a time sufficient for a layer of the amphipathic molecules to form at the interface between the polar medium and the apolar medium; and, either before, during or after any one of steps (i) to (iii),
(iv) contacting a second volume comprising polar medium with the apolar medium.

40. A method according to claim 39 wherein the first volume is a droplet or bead and step (i) comprises forming or introducing a droplet or bead of polar medium in the apolar medium.

41. A method according to claim 39 wherein step (iv) comprises applying a second volume of polar medium onto a surface of the apolar medium.

42. A method according to claim 1 wherein the first volume comprising polar medium is a droplet or bead.

43. A method according to claim 42 wherein a mean diameter of the droplets or beads is from 5 µm to 500 µm.

44. A method according to claim 1 wherein the second volume comprises a sample suspected of comprising a target analyte.

45. A method according to claim 44 wherein the target analyte is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

46. A method according to claim 1 wherein the first and second volumes comprising polar medium are both droplets or beads.

47. A method according to claim 1 which comprises:
(a) providing at least three volumes comprising polar medium which are separated from one another by an apolar medium, wherein at least one of, or each of, said volumes comprises a layer comprising said amphipathic molecules at the interface between the polar medium and the apolar medium; and
(b) causing each of said volumes to come into contact with another of said volumes to form a membrane comprising said amphipathic molecules between the volumes of polar medium.

48. A method according to claim 47 wherein each of said volumes is a droplet or bead and step (b) produces a chain or network of the droplets or beads.

49. A method according to claim 1 which comprises:
(a) providing a plurality of first volumes comprising polar medium and a second volume comprising polar medium, wherein the plurality of first volumes are separated from the second volume by an apolar medium,
wherein each of the first volumes is a droplet or bead, and
wherein each of the first volumes, and optionally the second volume, comprises a layer comprising said amphipathic molecules at the interface between the polar medium and the apolar medium; and
(b) causing the second volume to come into contact with each of the first volumes to form membranes comprising said amphipathic molecules between the second volume and each of the first volumes.

50. A method according to claim 49 wherein the second volume of polar medium comprises a sample suspected of comprising a target analyte.

51. A method according to claim 1 wherein at least one of the volumes comprising polar medium, or the apolar medium, further comprises a membrane protein, which membrane protein is capable of insertion into the membrane or a plurality of membranes comprising the amphipathic molecules.

52. A method according to claim 51 wherein the membrane protein is an ion channel or pore.

53. A method according to claim 52 wherein first volume comprising polar medium or the apolar medium comprises a surfactant.

54. A method according to claim 53 wherein the hydrophobic core group and, when present, one or more additional hydrophobic core groups, comprise a polysiloxane and the surfactant is organosilicon based.

55. A method according to claim 54 wherein the apolar medium is a silicone oil.

56. A method according to claim 1 wherein the membrane or each of a plurality of membranes comprising said amphipathic molecules further comprises a membrane protein.

57. A method according to claim 1, further comprising taking an electrical measurement and/or an optical measurement on the volumes comprising polar medium to perform an experiment involving a process occurring at or through the membrane between the volumes.

58. A method according to claim 1, further comprising bringing electrodes into electrical contact with the volumes of polar medium before a membrane has formed between the volumes of polar medium and taking an electrical measurement using the electrodes.

59. A method according to claim 1 wherein at least one of the volumes comprising polar medium is an aqueous medium.

60. A method according to claim 59 wherein the aqueous medium is a gel.

61. A method according to claim 59 wherein the at least one of the volumes is the first volume.

62. A method according to claim 1 wherein at least one of the volumes comprising polar medium further comprises a redox couple or a member of a redox couple which may be partially oxidised or reduced to provide the redox couple.

63. A method according to claim 1 wherein the apolar medium is an oil.

64. A method according to claim 1 wherein the apolar medium comprises a hydrocarbon or a silicone oil or a mixture thereof.

65. A system comprising
a first volume of a polar medium;
a second volume of a polar medium; and
a membrane between the first and second volumes of polar medium, which membrane comprises amphipathic molecules,
wherein each of the amphipathic molecules comprises a first outer hydrophilic group, a hydrophobic core group, and a second outer hydrophilic group, wherein the first and second outer hydrophilic groups are linked to opposite ends of the hydrophobic core group,
and wherein the first volume of polar medium is within an apolar medium.

66. A system according to claim 65 which further comprises a layer of said amphipathic molecules at an interface between the first volume of polar medium and the apolar medium.

67. A system according to claim 65 wherein the first volume of polar medium is a droplet or bead.

68. A system according to claim 67 wherein a mean diameter of the droplets or beads is from 5 µm to 500 µm.

69. A system according to claim 65 wherein the amphipathic molecules are poly(2-methyloxazoline)-block-poly(dimethylsiloxane)-block-poly(2-methyloxazoline) (PMOXA-PDMS-PMOXA).

70. A system according to claim 65, wherein the membrane comprises a monolayer of the amphipathic molecules.

71. A system according to claim 65, wherein the membrane comprises first and second outer polar regions formed by the first and second outer hydrophilic groups of the amphipathic molecules, and a middle apolar region formed by the hydrophobic core group of the amphipathic molecules, wherein said first and second outer polar regions contact the volumes of polar medium on either side of the membrane.

72. A system according to claim 65 wherein each of the first and second volumes of polar medium is a droplet or a bead.

73. A system according to claim 65 wherein each of the first and second volumes of polar medium is within said apolar medium and the system further comprises: a layer of said amphipathic molecules at an interface between the first volume of polar medium and the apolar medium, and a layer of said amphipathic molecules at an interface between the second volume of polar medium and the apolar medium.

74. A system according to claim 65 which comprises one or more further volumes of polar medium and one or more further membranes comprising said amphipathic molecules, wherein each further volume of polar medium is separated from another of the volumes of polar medium by a said further membrane.

75. A system according to claim 74 wherein each of the first, second and further volumes of polar medium is a droplet or a bead.

76. A system according to claim 65 which comprises a plurality of first volumes within the apolar medium and a plurality of respective membranes comprising said amphipathic molecules between the plurality of first volumes and the second volume.

77. A system according to claim 76 wherein each of the first volumes of polar medium is a droplet or bead.

78. A system according to claim 65 wherein the second volume comprises a sample suspected of comprising a target analyte.

79. A system according to claim 78 wherein the target analyte is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

80. A system according to claim 65, wherein the membrane or each of a plurality of membranes further comprise a membrane protein.

81. A system according to claim 80 wherein the membrane protein is an ion channel or a pore.

82. A system according to claim 65, wherein at least one of the first and second volumes of polar medium has an electrode in contact therewith.

83. A system according to claim 65 wherein the polar medium is an aqueous medium.

84. A system according to claim 65 wherein the polar medium is a gel.

85. A system according to claim 65 wherein at least one of the volumes of polar medium further comprises a redox couple or a member of a redox couple which may be partially oxidised or reduced to provide the redox couple.

86. A system according to claim 85 wherein the at least one of the volumes is the first volume.

87. A system according to claim 65 wherein the apolar medium is an oil.

88. A system according to claim 65 further comprising a surfactant in the apolar medium or in one of the volumes of polar medium.

89. A system according to claim 88 wherein the apolar medium comprises a silicone oil, the surfactant is organo-silicon-based and the hydrophobic core group and, when present, one or more additional hydrophobic polymer segments, comprises a polysiloxane.

90. A system according to claim 65 wherein the apolar medium comprises a hydrocarbon or a silicone oil or a mixture thereof.

91. A method of characterising a target analyte, comprising:
   (a) contacting the target analyte with a transmembrane pore present in a membrane of the system as defined in claim 65; and
   (b) taking one or more electrical measurements and/or one or more optical measurements as the analyte moves with respect to the pore or of the presence of analyte within the pore, wherein the measurements are indicative of one or more characteristics of the target analyte and thereby characterising the target analyte.

92. A method according to claim 91, wherein step (b) comprises measuring a current passing through the pore as the analyte moves with respect to the pore wherein the current is indicative of one or more characteristics of the analyte and thereby characterising the analyte.

93. A method according to claim 91, wherein the target analyte is a metal ion, an inorganic salt, a polymer, an amino acid, a peptide, a polypeptide, a protein, a nucleotide, an oligonucleotide, a polynucleotide, a dye, a bleach, a pharmaceutical, a diagnostic agent, a recreational drug, an explosive or an environmental pollutant.

94. A method according to claim 93, wherein the target analyte is a target polynucleotide.

95. A method according to claim 94, wherein step (a) comprises forming a complex, outside of the pore, between the target polynucleotide and a polynucleotide binding protein, and contacting the pore with the complex such that the polynucleotide binding protein controls the movement of the target polynucleotide through the pore.

96. A method according to claim 91, wherein the pore is a transmembrane protein pore.

97. A method according to claim 96, wherein the transmembrane protein pore is:
   (a) selected from a hemolysin, leukocidin, *Mycobacterium smegmatis* porin A (MspA), outer membrane porin F (OmpF), outer membrane porin G (OmpG), outer membrane phospholipase A, *Neisseria* autotransporter lipoprotein (NalP) and WZA;
   (b) formed of eight identical subunits as shown in SEQ ID NO: 2 or is a variant thereof in which one or more of the eight subunits has at least 50% homology to SEQ ID NO: 2 based on amino acid identity over the entire sequence and retains pore activity; or
   (c) α-hemolysin formed of seven identical subunits as shown in SEQ ID NO: 4 or is a variant thereof in which one or more of the seven subunits has at least 50% homology to SEQ ID NO: 4 based on amino acid identity over the entire sequence and retains pore activity.

98. A method of forming a sensor for characterising a target polynucleotide, comprising forming a complex between (a) a pore present in a membrane of the system as defined in claim 65 and (b) a polynucleotide binding protein and thereby forming a sensor for characterising the target polynucleotide.

99. A sensor for characterising a target polynucleotide, comprising a complex between (a) a pore present in a membrane of the system as defined in claim 65 and (b) a polynucleotide binding protein.

100. A kit for characterising a target polynucleotide comprising (a) a pore present in a membrane of the system as defined in claim 65 and (b) a separate polynucleotide binding protein.

101. An apparatus for characterising target polynucleotides in a sample, comprising (a) a plurality of pores present in a plurality of membranes of one or more systems as defined in claim 65 and separately (b) a plurality of polynucleotide binding proteins.

102. A volume comprising polar medium, which volume is disposed within an apolar medium, and which volume has a structure comprising a layer comprising amphipathic molecules around a surface thereof, between the polar medium and the apolar medium, wherein each of the amphipathic molecules comprises a first outer hydrophilic group, a hydrophobic core group, and a second outer hydrophilic group, wherein the first and second outer hydrophilic groups are linked to opposite ends of the hydrophobic core group, and wherein each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$.

103. A volume of a polar medium according to claim 102 wherein the amphipathic molecules are each a copolymer having a linear or graft structure and comprising at least three polymer segments, wherein the hydrophobic core group is an inner hydrophobic polymer segment, B, and the first and second outer hydrophilic groups are first and second outer hydrophilic polymer segments, A1 and A2, and wherein the first and second outer hydrophilic polymer segments, A1 and A2, are pendant from the inner hydrophobic polymer segment, B.

104. A volume of a polar medium according to claim 102, wherein the volume comprising polar medium is a droplet of said polar medium or a bead comprising said polar medium.

105. A process for producing a volume comprising polar medium, which volume is disposed within an apolar medium, and which volume has a structure comprising a layer comprising amphipathic molecules around a surface thereof, between the polar medium and the apolar medium, wherein each of the amphipathic molecules comprises a first outer hydrophilic group, a hydrophobic core group, and a second outer hydrophilic group, wherein the first and second outer hydrophilic groups are linked to opposite ends of the hydrophobic core group, and wherein each of the amphipathic molecules is a copolymer comprising at least three polymer segments, wherein the hydrophobic core group is an inner hydrophobic polymer segment, B, and the first and second outer hydrophilic groups are first and second outer hydrophilic polymer segments, $A_1$ and $A_2$, which process comprises:
(i) introducing a volume of a polar medium into an apolar medium;
(ii) providing the amphipathic molecules, in the apolar medium or the polar medium or both, either before or after (i); and
(iii) leaving the volume of polar medium for a time sufficient for the layer comprising the amphipathic molecules to form at an interface between the polar medium and the apolar medium.

\* \* \* \* \*

UNITED STATES PATENT AND TRADEMARK OFFICE
CERTIFICATE OF CORRECTION

PATENT NO. : 9,823,235 B2
APPLICATION NO. : 14/438670
DATED : November 21, 2017
INVENTOR(S) : Andrew John Heron et al.

It is certified that error appears in the above-identified patent and that said Letters Patent is hereby corrected as shown below:

On the Title Page

At Column 1 (73) Assignee:
"Oxford Nanopre Technologies Ltd.,
Ocford (GB)"
Should read:
"Oxford Nanopore Technologies Ltd.,
Oxford (GB)"

Signed and Sealed this
Eighth Day of May, 2018

Andrei Iancu
*Director of the United States Patent and Trademark Office*

SEQUENCE LISTING

<160> NUMBER OF SEQ ID NOS: 25

<210> SEQ ID NO 1
<211> LENGTH: 558
<212> TYPE: DNA
<213> ORGANISM: Artificial sequence
<220> FEATURE:
<223> OTHER INFORMATION: MS-B1

<400> SEQUENCE: 1

```
atgggtctgg ataatgaact gagcctggtg gacggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180
ggcacgctgg aactgggtta tcagattggc tttccgtggt cactgggcgt tggtatcaac     240
ttctcgtaca ccacgccgaa tattctgatc aacaatggta acattaccgc accgccgttt     300
ggcctgaaca gcgtgattac gccgaacctg tttccgggtg ttagcatctc tgcccgtctg     360
ggcaatggtc cgggcattca agaagtggca acctttagtg tgcgcgtttc cggcgctaaa     420
ggcggtgtcg cggtgtctaa cgcccacggt accgttacgg gcgcggccgg cggtgtcctg     480
ctgcgtccgt tcgcgcgcct gattgcctct accggcgaca gcgttacgac ctatggcgaa     540
ccgtggaata tgaactaa                                                   558
```

<210> SEQ ID NO 2
<211> LENGTH: 184
<212> TYPE: PRT
<213> ORGANISM: Artificial sequence
<220> FEATURE:
<223> OTHER INFORMATION: MS-B1

<400> SEQUENCE: 2

```
Gly Leu Asp Asn Glu Leu Ser Leu Val Asp Gly Gln Asp Arg Thr Leu
1               5                   10                  15
Thr Val Gln Gln Trp Asp Thr Phe Leu Asn Gly Val Phe Pro Leu Asp
            20                  25                  30
Arg Asn Arg Leu Thr Arg Glu Trp Phe His Ser Gly Arg Ala Lys Tyr
        35                  40                  45
Ile Val Ala Gly Pro Gly Ala Asp Glu Phe Glu Gly Thr Leu Glu Leu
    50                  55                  60
Gly Tyr Gln Ile Gly Phe Pro Trp Ser Leu Gly Val Gly Ile Asn Phe
65                  70                  75                  80
Ser Tyr Thr Thr Pro Asn Ile Leu Ile Asn Asn Gly Asn Ile Thr Ala
                85                  90                  95
Pro Pro Phe Gly Leu Asn Ser Val Ile Thr Pro Asn Leu Phe Pro Gly
            100                 105                 110
Val Ser Ile Ser Ala Arg Leu Gly Asn Gly Pro Gly Ile Gln Glu Val
        115                 120                 125
Ala Thr Phe Ser Val Arg Val Ser Gly Ala Lys Gly Gly Val Ala Val
    130                 135                 140
Ser Asn Ala His Gly Thr Val Thr Gly Ala Ala Gly Gly Val Leu Leu
145                 150                 155                 160
Arg Pro Phe Ala Arg Leu Ile Ala Ser Thr Gly Asp Ser Val Thr Thr
                165                 170                 175
Tyr Gly Glu Pro Trp Asn Met Asn
            180
```

<210> SEQ ID NO 3
<211> LENGTH: 885
<212> TYPE: DNA
<213> ORGANISM: Artificial sequence
<220> FEATURE:
<223> OTHER INFORMATION: a-HL-NN

<400> SEQUENCE: 3

```
atggcagatt ctgatattaa tattaaaacc ggtactacag atattggaag caatactaca      60
gtaaaaacag gtgatttagt cacttatgat aaagaaaatg gcatgcacaa aaaagtattt     120
tatagttta tcgatgataa aaatcacaat aaaaaactgc tagttattag aacaaaaggt     180
accattgctg gtcaatatag agtttatagc gaagaaggtg ctaacaaaag tggtttagcc     240
tggccttcag cctttaaggt acagttgcaa ctacctgata tgaagtagc tcaaatatct     300
gattactatc caagaaattc gattgataca aaaaactata tgagtacttt aacttatgga     360
ttcaacggta atgttactgg tgatgataca ggaaaaattg gcggccttat tggtgcaaat     420
gtttcgattg gtcatacact gaactatgtt caacctgatt tcaaaacaat tttagagagc     480
ccaactgata aaaagtagg ctggaaagtg atatttaaca aatggtgaa tcaaaattgg     540
ggaccatacg atcgagattc ttggaacccg gtatatggca atcaacttt catgaaaact     600
agaaatggtt ctatgaaagc agcagataac ttccttgatc taacaaagc aagttctcta     660
ttatcttcag ggttttcacc agacttcgct acagttatta ctatggatag aaagcatcc     720
aaacaacaaa caaatataga tgtaatatac gaacgagttc gtgatgatta ccaattgcat     780
tggacttcaa caaattggaa aggtaccaat actaaagata atggacaga tcgttcttca     840
gaaagatata aaatcgattg ggaaaagaa gaaatgacaa attaa                     885
```

```
<210> SEQ ID NO 4
<211> LENGTH: 293
<212> TYPE: PRT
<213> ORGANISM: Artificial sequence
<220> FEATURE:
<223> OTHER INFORMATION: a-HL-NN

<400> SEQUENCE: 4
```

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Asn Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
130                 135                 140

Thr Leu Asn Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

```
<210> SEQ ID NO 5
<211> LENGTH: 184
<212> TYPE: PRT
<213> ORGANISM: Mycobacterium smegmatis

<400> SEQUENCE: 5
```

Gly Leu Asp Asn Glu Leu Ser Leu Val Asp Gly Gln Asp Arg Thr Leu
1               5                   10                  15

Thr Val Gln Gln Trp Asp Thr Phe Leu Asn Gly Val Phe Pro Leu Asp
                20                  25                  30

-continued

Arg Asn Arg Leu Thr Arg Glu Trp Phe His Ser Gly Arg Ala Lys Tyr
         35                  40                  45

Ile Val Ala Gly Pro Gly Ala Asp Glu Phe Glu Gly Thr Leu Glu Leu
 50                  55                  60

Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asp Asp Gly Asp Ile Thr Ala
                 85                  90                  95

Pro Pro Phe Gly Leu Asn Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Val Ala Val
        130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 6
<211> LENGTH: 184
<212> TYPE: PRT
<213> ORGANISM: Mycobacterium smegmatis

<400> SEQUENCE: 6

Gly Leu Asp Asn Glu Leu Ser Leu Val Asp Gly Gln Asp Arg Thr Leu
 1               5                  10                  15

Thr Val Gln Gln Trp Asp Thr Phe Leu Asn Gly Val Phe Pro Leu Asp
             20                  25                  30

Arg Asn Arg Leu Thr Arg Glu Trp Phe His Ser Gly Arg Ala Lys Tyr
         35                  40                  45

Ile Val Ala Gly Pro Gly Ala Asp Glu Phe Glu Gly Thr Leu Glu Leu
 50                  55                  60

Gly Tyr Gln Ile Gly Phe Pro Trp Ser Leu Gly Val Gly Ile Asn Phe
 65                  70                  75                  80

Ser Tyr Thr Thr Pro Asn Ile Leu Ile Asp Asp Gly Asp Ile Thr Gly
                 85                  90                  95

Pro Pro Phe Gly Leu Glu Ser Val Ile Thr Pro Asn Leu Phe Pro Gly
                100                 105                 110

Val Ser Ile Ser Ala Asp Leu Gly Asn Gly Pro Gly Ile Gln Glu Val
            115                 120                 125

Ala Thr Phe Ser Val Asp Val Ser Gly Pro Ala Gly Val Ala Val
        130                 135                 140

Ser Asn Ala His Gly Thr Val Thr Gly Ala Ala Gly Val Leu Leu
145                 150                 155                 160

Arg Pro Phe Ala Arg Leu Ile Ala Ser Thr Gly Asp Ser Val Thr Thr
                165                 170                 175

Tyr Gly Glu Pro Trp Asn Met Asn
            180

<210> SEQ ID NO 7
<211> LENGTH: 183
<212> TYPE: PRT

<213> ORGANISM: Mycobacterium smegmatis

<400> SEQUENCE: 7

| | | | | | | | | | | | | | | | |
|---|---|---|---|---|---|---|---|---|---|---|---|---|---|---|---|
| Val | Asp | Asn | Gln | Leu | Ser | Val | Val | Asp | Gly | Gln | Gly | Arg | Thr | Leu | Thr |
| 1 | | | | 5 | | | | | 10 | | | | | 15 | |
| Val | Gln | Gln | Ala | Glu | Thr | Phe | Leu | Asn | Gly | Val | Phe | Pro | Leu | Asp | Arg |
| | | | 20 | | | | | 25 | | | | | 30 | | |
| Asn | Arg | Leu | Thr | Arg | Glu | Trp | Phe | His | Ser | Gly | Arg | Ala | Thr | Tyr | His |
| | | | 35 | | | | | 40 | | | | | 45 | | |
| Val | Ala | Gly | Pro | Gly | Ala | Asp | Glu | Phe | Glu | Gly | Thr | Leu | Glu | Leu | Gly |
| | | 50 | | | | | 55 | | | | | 60 | | | |
| Tyr | Gln | Val | Gly | Phe | Pro | Trp | Ser | Leu | Gly | Val | Gly | Ile | Asn | Phe | Ser |
| 65 | | | | | 70 | | | | | 75 | | | | | 80 |
| Tyr | Thr | Thr | Pro | Asn | Ile | Leu | Ile | Asp | Gly | Gly | Asp | Ile | Thr | Gln | Pro |
| | | | | 85 | | | | | 90 | | | | | 95 | |
| Pro | Phe | Gly | Leu | Asp | Thr | Ile | Ile | Thr | Pro | Asn | Leu | Phe | Pro | Gly | Val |
| | | | | 100 | | | | | 105 | | | | | 110 | |
| Ser | Ile | Ser | Ala | Asp | Leu | Gly | Asn | Gly | Pro | Gly | Ile | Gln | Glu | Val | Ala |
| | | | | 115 | | | | | 120 | | | | | 125 | |
| Thr | Phe | Ser | Val | Asp | Val | Lys | Gly | Ala | Lys | Gly | Ala | Val | Ala | Val | Ser |
| | | | 130 | | | | | 135 | | | | | 140 | | |
| Asn | Ala | His | Gly | Thr | Val | Thr | Gly | Ala | Ala | Gly | Gly | Val | Leu | Leu | Arg |
| 145 | | | | | 150 | | | | | 155 | | | | | 160 |
| Pro | Phe | Ala | Arg | Leu | Ile | Ala | Ser | Thr | Gly | Asp | Ser | Val | Thr | Thr | Tyr |
| | | | | 165 | | | | | 170 | | | | | 175 | |
| Gly | Glu | Pro | Trp | Asn | Met | Asn | | | | | | | | | |
| | | | | 180 | | | | | | | | | | | |

<210> SEQ ID NO 8
<211> LENGTH: 1830
<212> TYPE: DNA
<213> ORGANISM: bacteriophage phi AR29

<400> SEQUENCE: 8

| | | | | | |
|---|---|---|---|---|---|
| atgaaacaca | tgccgcgtaa | aatgtatagc | tgcgcgtttg | aaaccacgac | caaagtggaa | 60 |
| gattgtcgcg | tttgggccta | tggctacatg | aacatcgaag | atcattctga | atacaaaatc | 120 |
| ggtaacagtc | tggatgaatt | tatggcatgg | gtgctgaaag | ttcaggcgga | tctgtacttc | 180 |
| cacaacctga | aatttgatgg | cgcattcatt | atcaactggc | tggaacgtaa | tggctttaaa | 240 |
| tggagcgcgg | atggtctgcc | gaacacgtat | aataccatta | tctctcgtat | gggccagtgg | 300 |
| tatatgattg | atatctgcct | gggctacaaa | ggtaaacgca | aaattcatac | cgtgatctat | 360 |
| gatagcctga | aaaactgccg | tttccggtg | aagaaaattg | cgaaagattt | caaactgacg | 420 |
| gttctgaaag | gcgatattga | ttatcacaaa | gaacgtccgg | ttggttacaa | aatcaccccg | 480 |
| gaagaatacg | catacatcaa | aaacgatatc | cagatcatcg | cagaagcgct | gctgattcag | 540 |
| tttaaacagg | gcctggatcg | catgaccgcg | ggcagtgata | gcctgaaagg | tttcaaagat | 600 |
| atcatcacga | ccaaaaaatt | caaaaaagtg | ttcccgacgc | tgagcctggg | tctggataaa | 660 |
| gaagttcgtt | atgcctaccg | cggcggtttt | acctggctga | acgatcgttt | caaagaaaaa | 720 |
| gaaattggcg | agggtatggt | gtttgatgtt | aatagtctgt | atccggcaca | gatgtacagc | 780 |
| cgcctgctgc | cgtatggcga | accgatcgtg | ttcgagggta | aatatgtttg | ggatgaagat | 840 |
| tacccgctgc | atattcagca | catccgttgt | gaatttgaac | tgaaagaagg | ctatattccg | 900 |
| accattcaga | tcaaacgtag | tcgcttctat | aagggtaacg | aatacctgaa | aagctctggc | 960 |

```
ggtgaaatcg cggatctgtg gctgagtaac gtggatctgg aactgatgaa agaacactac   1020
gatctgtaca acgttgaata catcagcggc ctgaaattta agccacgac cggtctgttc   1080 aaagatttca tcgataaatg gacctacatc aaaacgacct ctgaaggcgc gattaaacag   1140
ctggccaaac tgatgctgaa cagcctgtat ggcaaattcg cctctaatcc ggatgtgacc   1200
ggtaaagttc cgtacctgaa agaaaatggc gcactgggtt ttcgcctggg cgaagaagaa   1260
acgaaagatc cggtgtatac cccgatgggt gttttcatta cggcctgggc acgttacacg   1320
accatcaccg cggcccaggc atgctatgat cgcattatct actgtgatac cgattctatt   1380
catctgacgg gcaccgaaat cccgatgtg attaaagata tcgttgatcc gaaaaaactg   1440
ggttattggg cccacgaaag tacgtttaaa cgtgcaaaat acctgcgcca gaaaacctac   1500
atccaggata tctacatgaa agaagtggat ggcaaactgg ttgaaggttc tccggatgat   1560
tacaccgata tcaaattcag tgtgaaatgc gccggcatga cggataaaat caaaaaagaa   1620
gtgaccttcg aaaacttcaa agttggtttc agccgcaaaa tgaaaccgaa accggtgcag   1680
gttccgggcg tgtggttct ggtggatgat acgtttacca ttaaatctgg cggtagtgcg   1740
tggagccatc cgcagttcga aaaggcggt ggctctggtg gcggttctgg cggtagtgcc   1800
tggagccacc cgcagtttga aaataataa                                    1830
```

<210> SEQ ID NO 9
<211> LENGTH: 608
<212> TYPE: PRT
<213> ORGANISM: bacteriophage phi AR29

<400> SEQUENCE: 9

```
Met Lys His Met Pro Arg Lys Met Tyr Ser Cys Ala Phe Glu Thr Thr
1               5                   10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
    50                  55                  60

Phe Asp Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
    130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
```

```
            210                 215                 220
Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
    290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
    370                 375                 380

Met Leu Asn Ser Leu Tyr Gly Lys Phe Ala Ser Asn Pro Asp Val Thr
385                 390                 395                 400

Gly Lys Val Pro Tyr Leu Lys Glu Asn Gly Ala Leu Gly Phe Arg Leu
                405                 410                 415

Gly Glu Glu Glu Thr Lys Asp Pro Val Tyr Thr Pro Met Gly Val Phe
            420                 425                 430

Ile Thr Ala Trp Ala Arg Tyr Thr Thr Ile Thr Ala Ala Gln Ala Cys
        435                 440                 445

Tyr Asp Arg Ile Ile Tyr Cys Asp Thr Asp Ser Ile His Leu Thr Gly
    450                 455                 460

Thr Glu Ile Pro Asp Val Ile Lys Asp Ile Val Asp Pro Lys Lys Leu
465                 470                 475                 480

Gly Tyr Trp Ala His Glu Ser Thr Phe Lys Arg Ala Lys Tyr Leu Arg
                485                 490                 495

Gln Lys Thr Tyr Ile Gln Asp Ile Tyr Met Lys Glu Val Asp Gly Lys
            500                 505                 510

Leu Val Glu Gly Ser Pro Asp Asp Tyr Thr Asp Ile Lys Phe Ser Val
        515                 520                 525

Lys Cys Ala Gly Met Thr Asp Lys Ile Lys Lys Glu Val Thr Phe Glu
    530                 535                 540

Asn Phe Lys Val Gly Phe Ser Arg Lys Met Lys Pro Lys Pro Val Gln
545                 550                 555                 560

Val Pro Gly Gly Val Val Leu Val Asp Asp Thr Phe Thr Ile Lys Ser
                565                 570                 575

Gly Gly Ser Ala Trp Ser His Pro Gln Phe Glu Lys Gly Gly Gly Ser
            580                 585                 590

Gly Gly Gly Ser Gly Gly Ser Ala Trp Ser His Pro Gln Phe Glu Lys
        595                 600                 605

<210> SEQ ID NO 10
<211> LENGTH: 1390
<212> TYPE: DNA
<213> ORGANISM: Escherichia coli
```

<400> SEQUENCE: 10

```
atgatgaacg atggcaaaca gcagagcacc ttcctgtttc atgattatga aaccttcggt      60
acccatccgg ccctggatcg tccggcgcag tttgcggcca ttcgcaccga tagcgaattc     120
aatgtgattg gcgaaccgga agtgttttat tgcaaaccgg ccgatgatta tctgccgcag     180
ccgggtgcgg tgctgattac cggtattacc ccgcaggaag cgcgcgcgaa aggtgaaaac     240
gaagcggcgt ttgccgcgcg cattcatagc ctgtttaccg tgccgaaaac ctgcattctg     300
ggctataaca atgtgcgctt cgatgatgaa gttacccgta atatctttta tcgtaacttt     360
tatgatccgt atgcgtggag ctggcagcat gataacagcc gttgggatct gctggatgtg     420
atgcgcgcgt gctatgcgct cgcccggaa ggcattaatt ggccggaaaa cgatgatggc      480
ctgccgagct ttcgtctgga acatctgacc aaagccaacg gcattgaaca tagcaatgcc     540
catgatgcga tggccgatgt ttatgcgacc attgcgatgg cgaaactggt taaaacccgt     600
cagccgcgcc tgtttgatta tctgtttacc caccgtaaca acacaaact gatggcgctg      660
attgatgttc gcagatgaa accgctggtg catgtgagcg gcatgtttgg cgcctggcgc      720
ggcaacacca gctgggtggc cccgctggcc tggcacccgg aaaatcgtaa cgccgtgatt     780
atggttgatc tggccggtga tattagcccg ctgctggaac tggatagcga taccctgcgt     840
gaacgcctgt ataccgccaa aaccgatctg ggcgataatg ccgccgtgcc ggtgaaactg     900
gttcacatta acaaatgccc ggtgctggcc caggcgaaca ccctgcgccc ggaagatgcg     960
gatcgtctgg gtattaatcg ccagcattgt ctggataatc tgaaaatcct gcgtgaaaac    1020
ccgcaggtgc gtgaaaaagt ggtggcgatc ttcgcggaag cggaaccgtt caccccgagc    1080
gataacgtgg atgcgcagct gtataacggc ttctttagcg atgccgatcg cgcggcgatg    1140
aaaatcgttc tggaaaccga accgcgcaat ctgccggcgc tggatattac ctttgttgat    1200
aaacgtattg aaaaactgct gtttaattat cgtgcgcgca ttttccgggg taccctggat    1260
tatgccgaac agcagcgttg gctggaacat cgtcgtcagg ttttcacccc ggaatttctg    1320
cagggttatg cggatgaact gcagatgctg gttcagcagt atgccgatga taagaaaaaa    1380
gtggcgctgc                                                           1390
```

<210> SEQ ID NO 11
<211> LENGTH: 485
<212> TYPE: PRT
<213> ORGANISM: Escherichia coli

<400> SEQUENCE: 11

```
Met Met Asn Asp Gly Lys Gln Gln Ser Thr Phe Leu Phe His Asp Tyr
1               5                   10                  15

Glu Thr Phe Gly Thr His Pro Ala Leu Asp Arg Pro Ala Gln Phe Ala
            20                  25                  30

Ala Ile Arg Thr Asp Ser Glu Phe Asn Val Ile Gly Glu Pro Glu Val
        35                  40                  45

Phe Tyr Cys Lys Pro Ala Asp Asp Tyr Leu Pro Gln Pro Gly Ala Val
    50                  55                  60

Leu Ile Thr Gly Ile Thr Pro Gln Glu Ala Arg Ala Lys Gly Glu Asn
65                  70                  75                  80

Glu Ala Ala Phe Ala Ala Arg Ile His Ser Leu Phe Thr Val Pro Lys
                85                  90                  95

Thr Cys Ile Leu Gly Tyr Asn Asn Val Arg Phe Asp Asp Glu Val Thr
            100                 105                 110
```

```
Arg Asn Ile Phe Tyr Arg Asn Phe Tyr Asp Pro Tyr Ala Trp Ser Trp
            115                 120                 125

Gln His Asp Asn Ser Arg Trp Asp Leu Leu Asp Val Met Arg Ala Cys
    130                 135                 140

Tyr Ala Leu Arg Pro Glu Gly Ile Asn Trp Pro Glu Asn Asp Asp Gly
145                 150                 155                 160

Leu Pro Ser Phe Arg Leu Glu His Leu Thr Lys Ala Asn Gly Ile Glu
                165                 170                 175

His Ser Asn Ala His Asp Ala Met Ala Asp Val Tyr Ala Thr Ile Ala
            180                 185                 190

Met Ala Lys Leu Val Lys Thr Arg Gln Pro Arg Leu Phe Asp Tyr Leu
        195                 200                 205

Phe Thr His Arg Asn Lys His Lys Leu Met Ala Leu Ile Asp Val Pro
    210                 215                 220

Gln Met Lys Pro Leu Val His Val Ser Gly Met Phe Gly Ala Trp Arg
225                 230                 235                 240

Gly Asn Thr Ser Trp Val Ala Pro Leu Ala Trp His Pro Glu Asn Arg
                245                 250                 255

Asn Ala Val Ile Met Val Asp Leu Ala Gly Asp Ile Ser Pro Leu Leu
            260                 265                 270

Glu Leu Asp Ser Asp Thr Leu Arg Glu Arg Leu Tyr Thr Ala Lys Thr
        275                 280                 285

Asp Leu Gly Asp Asn Ala Ala Val Pro Val Lys Leu Val His Ile Asn
    290                 295                 300

Lys Cys Pro Val Leu Ala Gln Ala Asn Thr Leu Arg Pro Glu Asp Ala
305                 310                 315                 320

Asp Arg Leu Gly Ile Asn Arg Gln His Cys Leu Asp Asn Leu Lys Ile
                325                 330                 335

Leu Arg Glu Asn Pro Gln Val Arg Glu Lys Val Val Ala Ile Phe Ala
            340                 345                 350

Glu Ala Glu Pro Phe Thr Pro Ser Asp Asn Val Asp Ala Gln Leu Tyr
        355                 360                 365

Asn Gly Phe Phe Ser Asp Ala Asp Arg Ala Ala Met Lys Ile Val Leu
    370                 375                 380

Glu Thr Glu Pro Arg Asn Leu Pro Ala Leu Asp Ile Thr Phe Val Asp
385                 390                 395                 400

Lys Arg Ile Glu Lys Leu Leu Phe Asn Tyr Arg Ala Arg Asn Phe Pro
                405                 410                 415

Gly Thr Leu Asp Tyr Ala Glu Gln Gln Arg Trp Leu Glu His Arg Arg
            420                 425                 430

Gln Val Phe Thr Pro Glu Phe Leu Gln Gly Tyr Ala Asp Glu Leu Gln
        435                 440                 445

Met Leu Val Gln Gln Tyr Ala Asp Asp Lys Glu Lys Val Ala Leu Leu
    450                 455                 460

Lys Ala Leu Trp Gln Tyr Ala Glu Glu Ile Val Ser Gly Ser Gly His
465                 470                 475                 480

His His His His His
            485

<210> SEQ ID NO 12
<211> LENGTH: 804
<212> TYPE: DNA
<213> ORGANISM: Escherichia coli
```

<400> SEQUENCE: 12

```
atgaaatttg tctcttttaa tatcaacggc ctgcgcgcca gacctcacca gcttgaagcc      60
atcgtcgaaa agcaccaacc ggatgtgatt ggcctgcagg agacaaaagt tcatgacgat     120
atgtttccgc tcgaagaggt ggcgaagctc ggctacaacg tgttttatca cgggcagaaa     180
ggccattatg gcgtggcgct gctgaccaaa gagacgccga ttgccgtgcg tcgcggcttt     240
cccggtgacg acgaagaggc gcagcggcgg attattatgg cggaaatccc ctcactgctg     300
ggtaatgtca ccgtgatcaa cggttacttc ccgcagggtg aaagccgcga ccatccgata     360
aaattcccgg caaaagcgca gttttatcag aatctgcaaa actacctgga aaccgaactc     420
aaacgtgata atccggtact gattatgggc gatatgaata tcagccctac agatctggat     480
atcggcattg gcgaagaaaa ccgtaagcgc tggctgcgta ccggtaaatg ctcttttcctg    540
ccggaagagc gcgaatggat ggacaggctg atgagctggg ggttggtcga taccttccgc     600
catgcgaatc cgcaaacagc agatcgtttc tcatggtttg attaccgctc aaaaggtttt     660
gacgataacc gtggtctgcg catcgacctg ctgctcgcca gccaaccgct ggcagaatgt     720
tgcgtagaaa ccggcatcga ctatgaaatc gcagcatgg aaaaaccgtc gatcacgcc      780
cccgtctggg cgaccttccg ccgc                                            804
```

<210> SEQ ID NO 13
<211> LENGTH: 268
<212> TYPE: PRT
<213> ORGANISM: Escherichia coli

<400> SEQUENCE: 13

```
Met Lys Phe Val Ser Phe Asn Ile Asn Gly Leu Arg Ala Arg Pro His
1               5                   10                  15

Gln Leu Glu Ala Ile Val Glu Lys His Gln Pro Asp Val Ile Gly Leu
            20                  25                  30

Gln Glu Thr Lys Val His Asp Asp Met Phe Pro Leu Glu Glu Val Ala
        35                  40                  45

Lys Leu Gly Tyr Asn Val Phe Tyr His Gly Gln Lys Gly His Tyr Gly
    50                  55                  60

Val Ala Leu Leu Thr Lys Glu Thr Pro Ile Ala Val Arg Arg Gly Phe
65                  70                  75                  80

Pro Gly Asp Asp Glu Glu Ala Gln Arg Arg Ile Ile Met Ala Glu Ile
                85                  90                  95

Pro Ser Leu Leu Gly Asn Val Thr Val Ile Asn Gly Tyr Phe Pro Gln
            100                 105                 110

Gly Glu Ser Arg Asp His Pro Ile Lys Phe Pro Ala Lys Ala Gln Phe
        115                 120                 125

Tyr Gln Asn Leu Gln Asn Tyr Leu Glu Thr Glu Leu Lys Arg Asp Asn
    130                 135                 140

Pro Val Leu Ile Met Gly Asp Met Asn Ile Ser Pro Thr Asp Leu Asp
145                 150                 155                 160

Ile Gly Ile Gly Glu Glu Asn Arg Lys Arg Trp Leu Arg Thr Gly Lys
                165                 170                 175

Cys Ser Phe Leu Pro Glu Glu Arg Glu Trp Met Asp Arg Leu Met Ser
            180                 185                 190

Trp Gly Leu Val Asp Thr Phe Arg His Ala Asn Pro Gln Thr Ala Asp
        195                 200                 205

Arg Phe Ser Trp Phe Asp Tyr Arg Ser Lys Gly Phe Asp Asp Asn Arg
    210                 215                 220
```

```
Gly Leu Arg Ile Asp Leu Leu Leu Ala Ser Gln Pro Leu Ala Glu Cys
225                 230                 235                 240

Cys Val Glu Thr Gly Ile Asp Tyr Glu Ile Arg Ser Met Glu Lys Pro
                245                 250                 255

Ser Asp His Ala Pro Val Trp Ala Thr Phe Arg Arg
            260                 265
```

<210> SEQ ID NO 14
<211> LENGTH: 1275
<212> TYPE: DNA
<213> ORGANISM: Thermus thermophilus

<400> SEQUENCE: 14

```
atgtttcgtc gtaaagaaga tctggatccg ccgctggcac tgctgccgct gaaaggcctg      60
cgcgaagccg ccgcactgct ggaagaagcg ctgcgtcaag gtaaacgcat tcgtgttcac     120
ggcgactatg atgcggatgg cctgaccggc accgcgatcc tggttcgtgg tctggccgcc     180
ctgggtgcgg atgttcatcc gtttatcccg caccgcctgg aagaaggcta tggtgtcctg     240
atggaacgcg tcccggaaca tctggaagcc tcggacctgt ttctgaccgt tgactgcggc     300
attaccaacc atgcggaact gcgcgaactg ctggaaaatg gcgtggaagt cattgttacc     360
gatcatcata cgccgggcaa aacgccgccg ccgggtctgg tcgtgcatcc ggcgctgacg     420
ccggatctga agaaaaaacc gaccggcgca ggcgtggcgt ttctgctgct gtgggcactg     480
catgaacgcc tgggcctgcc gccgccgctg aatacgcgg  acctggcagc cgttggcacc     540
attgccgacg ttgccccgct gtggggttgg aatcgtgcac tggtgaaaga aggtctggca     600
cgcatcccgg cttcatcttg ggtgggcctg cgtctgctgg ctgaagccgt gggctatacc     660
ggcaaagcgg tcgaagtcgc tttccgcatc gcgccgcgca tcaatgcggc ttcccgcctg     720
ggcgaagcgg aaaaagccct gcgcctgctg ctgacggatg atgcggcaga agctcaggcg     780
ctggtcggca aactgcaccg tctgaacgcc gtcgtcaga  ccctggaaga agcgatgctg     840
cgcaaactgc tgccgcaggc cgacccggaa gcgaaagcca tcgttctgct ggacccggaa     900
ggccatccgg tgttatggg  tattgtggcc tctcgcatcc tggaagcgac cctgcgcccg     960
gtctttctgg tggcccaggg caaaggcacc gtgcgttcgc tggctccgat tccgccgtc    1020
gaagcactgc gcagcgcgga agatctgctg ctgcgttatg tggtcataa  agaagcggcg    1080
ggtttcgcaa tggatgaagc gctgtttccg gcgttcaaag cacgcgttga agcgtatgcc    1140
gcacgtttcc cggatccggt tcgtgaagtg cactgctgg  atctgctgcc ggaaccgggc    1200
ctgctgccgc aggtgttccg tgaactggca ctgctggaac cgtatggtga aggtaacccg    1260
gaaccgctgt tcctg                                                    1275
```

<210> SEQ ID NO 15
<211> LENGTH: 425
<212> TYPE: PRT
<213> ORGANISM: Thermus thermophilus

<400> SEQUENCE: 15

```
Met Phe Arg Arg Lys Glu Asp Leu Asp Pro Pro Leu Ala Leu Leu Pro
1               5                   10                  15

Leu Lys Gly Leu Arg Glu Ala Ala Ala Leu Leu Glu Glu Ala Leu Arg
            20                  25                  30

Gln Gly Lys Arg Ile Arg Val His Gly Asp Tyr Asp Ala Asp Gly Leu
        35                  40                  45
```

Thr Gly Thr Ala Ile Leu Val Arg Gly Leu Ala Ala Leu Gly Ala Asp
    50                  55                  60

Val His Pro Phe Ile Pro His Arg Leu Glu Glu Gly Tyr Gly Val Leu
 65                  70                  75                  80

Met Glu Arg Val Pro Glu His Leu Glu Ala Ser Asp Leu Phe Leu Thr
                 85                  90                  95

Val Asp Cys Gly Ile Thr Asn His Ala Glu Leu Arg Glu Leu Leu Glu
            100                 105                 110

Asn Gly Val Glu Val Ile Val Thr Asp His His Thr Pro Gly Lys Thr
        115                 120                 125

Pro Pro Pro Gly Leu Val Val His Pro Ala Leu Thr Pro Asp Leu Lys
130                 135                 140

Glu Lys Pro Thr Gly Ala Gly Val Ala Phe Leu Leu Leu Trp Ala Leu
145                 150                 155                 160

His Glu Arg Leu Gly Leu Pro Pro Leu Glu Tyr Ala Asp Leu Ala
                165                 170                 175

Ala Val Gly Thr Ile Ala Asp Val Ala Pro Leu Trp Gly Trp Asn Arg
            180                 185                 190

Ala Leu Val Lys Glu Gly Leu Ala Arg Ile Pro Ala Ser Ser Trp Val
        195                 200                 205

Gly Leu Arg Leu Leu Ala Glu Ala Val Gly Tyr Thr Gly Lys Ala Val
    210                 215                 220

Glu Val Ala Phe Arg Ile Ala Pro Arg Ile Asn Ala Ala Ser Arg Leu
225                 230                 235                 240

Gly Glu Ala Glu Lys Ala Leu Arg Leu Leu Thr Asp Asp Ala Ala
                245                 250                 255

Glu Ala Gln Ala Leu Val Gly Glu Leu His Arg Leu Asn Ala Arg Arg
            260                 265                 270

Gln Thr Leu Glu Glu Ala Met Leu Arg Lys Leu Leu Pro Gln Ala Asp
        275                 280                 285

Pro Glu Ala Lys Ala Ile Val Leu Leu Asp Pro Glu Gly His Pro Gly
    290                 295                 300

Val Met Gly Ile Val Ala Ser Arg Ile Leu Glu Ala Thr Leu Arg Pro
305                 310                 315                 320

Val Phe Leu Val Ala Gln Gly Lys Gly Thr Val Arg Ser Leu Ala Pro
                325                 330                 335

Ile Ser Ala Val Glu Ala Leu Arg Ser Ala Glu Asp Leu Leu Leu Arg
            340                 345                 350

Tyr Gly Gly His Lys Glu Ala Ala Gly Phe Ala Met Asp Glu Ala Leu
        355                 360                 365

Phe Pro Ala Phe Lys Ala Arg Val Glu Ala Tyr Ala Ala Arg Phe Pro
370                 375                 380

Asp Pro Val Arg Glu Val Ala Leu Leu Asp Leu Leu Pro Glu Pro Gly
385                 390                 395                 400

Leu Leu Pro Gln Val Phe Arg Glu Leu Ala Leu Leu Glu Pro Tyr Gly
                405                 410                 415

Glu Gly Asn Pro Glu Pro Leu Phe Leu
            420                 425

<210> SEQ ID NO 16
<211> LENGTH: 738
<212> TYPE: DNA
<213> ORGANISM: Bacteriophage lambda

<400> SEQUENCE: 16

```
tccggaagcg gctctggtag tggttctggc atgacaccgg acattatcct gcagcgtacc    60
gggatcgatg tgagagctgt cgaacagggg gatgatgcgt ggcacaaatt acggctcggc   120
gtcatcaccg cttcagaagt tcacaacgtg atagcaaaac cccgctccgg aaagaagtgg   180
cctgacatga aaatgtccta cttccacacc ctgcttgctg aggtttgcac cggtgtggct   240
ccggaagtta acgctaaagc actggcctgg ggaaaacagt acgagaacga cgccagaacc   300
ctgtttgaat tcacttccgg cgtgaatgtt actgaatccc cgatcatcta cgcgacgaa    360
agtatgcgta ccgcctgctc tcccgatggt ttatgcagtg acggcaacgg ccttgaactg   420
aaatgcccgt ttacctcccg ggatttcatg aagttccggc tcggtggttt cgaggccata   480
aagtcagctt acatggccca ggtgcagtac agcatgtggg tgacgcgaaa aaatgcctgg   540
tactttgcca actatgaccc gcgtatgaag cgtgaaggcc tgcattatgt cgtgattgag   600
cgggatgaaa agtacatggc gagttttgac gagatcgtgc cggagttcat cgaaaaaatg   660
gacgaggcac tggctgaaat tggttttgta tttggggagc aatggcgatc tggctctggt   720
tccggcagcg gttccgga                                                 738
```

<210> SEQ ID NO 17
<211> LENGTH: 226
<212> TYPE: PRT
<213> ORGANISM: Bacteriophage lambda

<400> SEQUENCE: 17

```
Met Thr Pro Asp Ile Ile Leu Gln Arg Thr Gly Ile Asp Val Arg Ala
1               5                   10                  15

Val Glu Gln Gly Asp Asp Ala Trp His Lys Leu Arg Leu Gly Val Ile
                20                  25                  30

Thr Ala Ser Glu Val His Asn Val Ile Ala Lys Pro Arg Ser Gly Lys
            35                  40                  45

Lys Trp Pro Asp Met Lys Met Ser Tyr Phe His Thr Leu Leu Ala Glu
        50                  55                  60

Val Cys Thr Gly Val Ala Pro Glu Val Asn Ala Lys Ala Leu Ala Trp
65                  70                  75                  80

Gly Lys Gln Tyr Glu Asn Asp Ala Arg Thr Leu Phe Glu Phe Thr Ser
                85                  90                  95

Gly Val Asn Val Thr Glu Ser Pro Ile Ile Tyr Arg Asp Glu Ser Met
            100                 105                 110

Arg Thr Ala Cys Ser Pro Asp Gly Leu Cys Ser Asp Gly Asn Gly Leu
        115                 120                 125

Glu Leu Lys Cys Pro Phe Thr Ser Arg Asp Phe Met Lys Phe Arg Leu
    130                 135                 140

Gly Gly Phe Glu Ala Ile Lys Ser Ala Tyr Met Ala Gln Val Gln Tyr
145                 150                 155                 160

Ser Met Trp Val Thr Arg Lys Asn Ala Trp Tyr Phe Ala Asn Tyr Asp
                165                 170                 175

Pro Arg Met Lys Arg Glu Gly Leu His Tyr Val Val Ile Glu Arg Asp
            180                 185                 190

Glu Lys Tyr Met Ala Ser Phe Asp Glu Ile Val Pro Glu Phe Ile Glu
        195                 200                 205

Lys Met Asp Glu Ala Leu Ala Glu Ile Gly Phe Val Phe Gly Glu Gln
    210                 215                 220

Trp Arg
225
```

<210> SEQ ID NO 18
<211> LENGTH: 760
<212> TYPE: PRT
<213> ORGANISM: Methanococcoides burtonii

<400> SEQUENCE: 18

```
Met Met Ile Arg Glu Leu Asp Ile Pro Arg Asp Ile Gly Phe Tyr
1               5                   10                  15

Glu Asp Ser Gly Ile Lys Glu Leu Tyr Pro Pro Gln Ala Glu Ala Ile
                20                  25                  30

Glu Met Gly Leu Leu Glu Lys Lys Asn Leu Leu Ala Ala Ile Pro Thr
            35                  40                  45

Ala Ser Gly Lys Thr Leu Leu Ala Glu Leu Ala Met Ile Lys Ala Ile
        50                  55                  60

Arg Glu Gly Gly Lys Ala Leu Tyr Ile Val Pro Leu Arg Ala Leu Ala
65                  70                  75                  80

Ser Glu Lys Phe Glu Arg Phe Lys Glu Leu Ala Pro Phe Gly Ile Lys
                85                  90                  95

Val Gly Ile Ser Thr Gly Asp Leu Asp Ser Arg Ala Asp Trp Leu Gly
                100                 105                 110

Val Asn Asp Ile Ile Val Ala Thr Ser Glu Lys Thr Asp Ser Leu Leu
            115                 120                 125

Arg Asn Gly Thr Ser Trp Met Asp Glu Ile Thr Thr Val Val Val Asp
        130                 135                 140

Glu Ile His Leu Leu Asp Ser Lys Asn Arg Gly Pro Thr Leu Glu Val
145                 150                 155                 160

Thr Ile Thr Lys Leu Met Arg Leu Asn Pro Asp Val Gln Val Val Ala
                165                 170                 175

Leu Ser Ala Thr Val Gly Asn Ala Arg Glu Met Ala Asp Trp Leu Gly
                180                 185                 190

Ala Ala Leu Val Leu Ser Glu Trp Arg Pro Thr Asp Leu His Glu Gly
            195                 200                 205

Val Leu Phe Gly Asp Ala Ile Asn Phe Pro Gly Ser Gln Lys Lys Ile
        210                 215                 220

Asp Arg Leu Glu Lys Asp Asp Ala Val Asn Leu Val Leu Asp Thr Ile
225                 230                 235                 240

Lys Ala Glu Gly Gln Cys Leu Val Phe Glu Ser Ser Arg Arg Asn Cys
                245                 250                 255

Ala Gly Phe Ala Lys Thr Ala Ser Ser Lys Val Ala Lys Ile Leu Asp
            260                 265                 270

Asn Asp Ile Met Ile Lys Leu Ala Gly Ile Ala Glu Glu Val Glu Ser
        275                 280                 285

Thr Gly Glu Thr Asp Thr Ala Ile Val Leu Ala Asn Cys Ile Arg Lys
    290                 295                 300

Gly Val Ala Phe His His Ala Gly Leu Asn Ser Asn His Arg Lys Leu
305                 310                 315                 320

Val Glu Asn Gly Phe Arg Gln Asn Leu Ile Lys Val Ile Ser Ser Thr
                325                 330                 335

Pro Thr Leu Ala Ala Gly Leu Asn Leu Pro Ala Arg Arg Val Ile Ile
            340                 345                 350

Arg Ser Tyr Arg Arg Phe Asp Ser Asn Phe Gly Met Gln Pro Ile Pro
        355                 360                 365

Val Leu Glu Tyr Lys Gln Met Ala Gly Arg Ala Gly Arg Pro His Leu
```

```
                    370                 375                 380
Asp Pro Tyr Gly Glu Ser Val Leu Leu Ala Lys Thr Tyr Asp Glu Phe
385                 390                 395                 400

Ala Gln Leu Met Glu Asn Tyr Val Glu Ala Asp Ala Glu Asp Ile Trp
                405                 410                 415

Ser Lys Leu Gly Thr Glu Asn Ala Leu Arg Thr His Val Leu Ser Thr
            420                 425                 430

Ile Val Asn Gly Phe Ala Ser Thr Arg Gln Glu Leu Phe Asp Phe Phe
        435                 440                 445

Gly Ala Thr Phe Phe Ala Tyr Gln Gln Asp Lys Trp Met Leu Glu Glu
    450                 455                 460

Val Ile Asn Asp Cys Leu Glu Phe Leu Ile Asp Lys Ala Met Val Ser
465                 470                 475                 480

Glu Thr Glu Asp Ile Glu Asp Ala Ser Lys Leu Phe Leu Arg Gly Thr
                485                 490                 495

Arg Leu Gly Ser Leu Val Ser Met Leu Tyr Ile Asp Pro Leu Ser Gly
            500                 505                 510

Ser Lys Ile Val Asp Gly Phe Lys Asp Ile Gly Lys Ser Thr Gly Gly
        515                 520                 525

Asn Met Gly Ser Leu Glu Asp Lys Gly Asp Asp Ile Thr Val Thr
    530                 535                 540

Asp Met Thr Leu Leu His Leu Val Cys Ser Thr Pro Asp Met Arg Gln
545                 550                 555                 560

Leu Tyr Leu Arg Asn Thr Asp Tyr Thr Ile Val Asn Glu Tyr Ile Val
                565                 570                 575

Ala His Ser Asp Glu Phe His Glu Ile Pro Asp Lys Leu Lys Glu Thr
            580                 585                 590

Asp Tyr Glu Trp Phe Met Gly Val Lys Thr Ala Met Leu Leu Glu
        595                 600                 605

Glu Trp Val Thr Glu Val Ser Ala Glu Asp Ile Thr Arg His Phe Asn
    610                 615                 620

Val Gly Glu Gly Asp Ile His Ala Leu Ala Asp Thr Ser Glu Trp Leu
625                 630                 635                 640

Met His Ala Ala Ala Lys Leu Ala Glu Leu Leu Gly Val Glu Tyr Ser
                645                 650                 655

Ser His Ala Tyr Ser Leu Glu Lys Arg Ile Arg Tyr Gly Ser Gly Leu
            660                 665                 670

Asp Leu Met Glu Leu Val Gly Ile Arg Gly Val Gly Arg Val Arg Ala
        675                 680                 685

Arg Lys Leu Tyr Asn Ala Gly Phe Val Ser Val Ala Lys Leu Lys Gly
    690                 695                 700

Ala Asp Ile Ser Val Leu Ser Lys Leu Val Gly Pro Lys Val Ala Tyr
705                 710                 715                 720

Asn Ile Leu Ser Gly Ile Gly Val Arg Val Asn Asp Lys His Phe Asn
                725                 730                 735

Ser Ala Pro Ile Ser Ser Asn Thr Leu Asp Thr Leu Leu Asp Lys Asn
            740                 745                 750

Gln Lys Thr Phe Asn Asp Phe Gln
        755                 760

<210> SEQ ID NO 19
<211> LENGTH: 707
<212> TYPE: PRT
<213> ORGANISM: Cenarchaeum symbiosum
```

<400> SEQUENCE: 19

```
Met Arg Ile Ser Glu Leu Asp Ile Pro Arg Pro Ala Ile Glu Phe Leu
1               5                   10                  15

Glu Gly Glu Gly Tyr Lys Lys Leu Tyr Pro Pro Gln Ala Ala Ala Ala
            20                  25                  30

Lys Ala Gly Leu Thr Asp Gly Lys Ser Val Leu Val Ser Ala Pro Thr
            35                  40                  45

Ala Ser Gly Lys Thr Leu Ile Ala Ala Ile Ala Met Ile Ser His Leu
        50                  55                  60

Ser Arg Asn Arg Gly Lys Ala Val Tyr Leu Ser Pro Leu Arg Ala Leu
65                  70                  75                  80

Ala Ala Glu Lys Phe Ala Glu Phe Gly Lys Ile Gly Gly Ile Pro Leu
                85                  90                  95

Gly Arg Pro Val Arg Val Gly Val Ser Thr Gly Asp Phe Glu Lys Ala
            100                 105                 110

Gly Arg Ser Leu Gly Asn Asn Asp Ile Leu Val Leu Thr Asn Glu Arg
            115                 120                 125

Met Asp Ser Leu Ile Arg Arg Pro Asp Trp Met Asp Glu Val Gly
130                 135                 140

Leu Val Ile Ala Asp Glu Ile His Leu Ile Gly Asp Arg Ser Arg Gly
145                 150                 155                 160

Pro Thr Leu Glu Met Val Leu Thr Lys Leu Arg Gly Leu Arg Ser Ser
                165                 170                 175

Pro Gln Val Val Ala Leu Ser Ala Thr Ile Ser Asn Ala Asp Glu Ile
            180                 185                 190

Ala Gly Trp Leu Asp Cys Thr Leu Val His Ser Thr Trp Arg Pro Val
            195                 200                 205

Pro Leu Ser Glu Gly Val Tyr Gln Asp Gly Glu Val Ala Met Gly Asp
210                 215                 220

Gly Ser Arg His Glu Val Ala Thr Gly Gly Pro Ala Val Asp
225                 230                 235                 240

Leu Ala Ala Glu Ser Val Ala Glu Gly Gly Gln Ser Leu Ile Phe Ala
                245                 250                 255

Asp Thr Arg Ala Arg Ser Ala Ser Leu Ala Ala Lys Ala Ser Ala Val
            260                 265                 270

Ile Pro Glu Ala Lys Gly Ala Asp Ala Ala Lys Leu Ala Ala Ala Ala
            275                 280                 285

Lys Lys Ile Ile Ser Ser Gly Gly Glu Thr Lys Leu Ala Lys Thr Leu
290                 295                 300

Ala Glu Leu Val Glu Lys Gly Ala Ala Phe His His Ala Gly Leu Asn
305                 310                 315                 320

Gln Asp Cys Arg Ser Val Val Glu Glu Glu Phe Arg Ser Gly Arg Ile
            325                 330                 335

Arg Leu Leu Ala Ser Thr Pro Thr Leu Ala Ala Gly Val Asn Leu Pro
            340                 345                 350

Ala Arg Arg Val Val Ile Ser Ser Val Met Arg Tyr Asn Ser Ser Ser
            355                 360                 365

Gly Met Ser Glu Pro Ile Ser Ile Leu Glu Tyr Lys Gln Leu Cys Gly
            370                 375                 380

Arg Ala Gly Arg Pro Gln Tyr Asp Lys Ser Gly Glu Ala Ile Val Val
385                 390                 395                 400

Gly Gly Val Asn Ala Asp Glu Ile Phe Asp Arg Tyr Ile Gly Gly Glu
```

```
            405                 410                 415
Pro Glu Pro Ile Arg Ser Ala Met Val Asp Asp Arg Ala Leu Arg Ile
            420                 425                 430

His Val Leu Ser Leu Val Thr Thr Ser Pro Gly Ile Lys Glu Asp Asp
            435                 440                 445

Val Thr Glu Phe Phe Leu Gly Thr Leu Gly Gly Gln Gln Ser Gly Glu
    450                 455                 460

Ser Thr Val Lys Phe Ser Val Ala Val Ala Leu Arg Phe Leu Gln Glu
465                 470                 475                 480

Glu Gly Met Leu Gly Arg Arg Gly Gly Arg Leu Ala Ala Thr Lys Met
                485                 490                 495

Gly Arg Leu Val Ser Arg Leu Tyr Met Asp Pro Met Thr Ala Val Thr
            500                 505                 510

Leu Arg Asp Ala Val Gly Glu Ala Ser Pro Gly Arg Met His Thr Leu
            515                 520                 525

Gly Phe Leu His Leu Val Ser Glu Cys Ser Glu Phe Met Pro Arg Phe
    530                 535                 540

Ala Leu Arg Gln Lys Asp His Glu Val Ala Glu Met Met Leu Glu Ala
545                 550                 555                 560

Gly Arg Gly Glu Leu Leu Arg Pro Val Tyr Ser Tyr Glu Cys Gly Arg
                565                 570                 575

Gly Leu Leu Ala Leu His Arg Trp Ile Gly Glu Ser Pro Glu Ala Lys
            580                 585                 590

Leu Ala Glu Asp Leu Lys Phe Glu Ser Gly Asp Val His Arg Met Val
    595                 600                 605

Glu Ser Ser Gly Trp Leu Leu Arg Cys Ile Trp Glu Ile Ser Lys His
610                 615                 620

Gln Glu Arg Pro Asp Leu Leu Gly Glu Leu Asp Val Leu Arg Ser Arg
625                 630                 635                 640

Val Ala Tyr Gly Ile Lys Ala Glu Leu Val Pro Leu Val Ser Ile Lys
                645                 650                 655

Gly Ile Gly Arg Val Arg Ser Arg Arg Leu Phe Arg Gly Gly Ile Lys
            660                 665                 670

Gly Pro Gly Asp Leu Ala Ala Val Pro Val Glu Arg Leu Ser Arg Val
    675                 680                 685

Glu Gly Ile Gly Ala Thr Leu Ala Asn Asn Ile Lys Ser Gln Leu Arg
    690                 695                 700

Lys Gly Gly
705

<210> SEQ ID NO 20
<211> LENGTH: 720
<212> TYPE: PRT
<213> ORGANISM: Thermococcus gammatolerans EJ3

<400> SEQUENCE: 20

Met Lys Val Asp Glu Leu Pro Val Asp Glu Arg Leu Lys Ala Val Leu
1               5                   10                  15

Lys Glu Arg Gly Ile Glu Glu Leu Tyr Pro Pro Gln Ala Glu Ala Leu
            20                  25                  30

Lys Ser Gly Ala Leu Glu Gly Arg Asn Leu Val Leu Ala Ile Pro Thr
        35                  40                  45

Ala Ser Gly Lys Thr Leu Val Ser Glu Ile Val Met Val Asn Lys Leu
    50                  55                  60
```

-continued

```
Ile Gln Glu Gly Gly Lys Ala Val Tyr Leu Val Pro Leu Lys Ala Leu
 65                  70                  75                  80

Ala Glu Glu Lys Tyr Arg Glu Phe Lys Glu Trp Glu Lys Leu Gly Leu
                 85                  90                  95

Lys Val Ala Ala Thr Gly Asp Tyr Asp Ser Thr Asp Asp Trp Leu
            100                 105                 110

Gly Arg Tyr Asp Ile Ile Val Ala Thr Ala Glu Lys Phe Asp Ser Leu
            115                 120                 125

Leu Arg His Gly Ala Arg Trp Ile Asn Asp Val Lys Leu Val Val Ala
        130                 135                 140

Asp Glu Val His Leu Ile Gly Ser Tyr Asp Arg Gly Ala Thr Leu Glu
145                 150                 155                 160

Met Ile Leu Thr His Met Leu Gly Arg Ala Gln Ile Leu Ala Leu Ser
                165                 170                 175

Ala Thr Val Gly Asn Ala Glu Glu Leu Ala Glu Trp Leu Asp Ala Ser
            180                 185                 190

Leu Val Val Ser Asp Trp Arg Pro Val Gln Leu Arg Arg Gly Val Phe
        195                 200                 205

His Leu Gly Thr Leu Ile Trp Glu Asp Gly Lys Val Glu Ser Tyr Pro
    210                 215                 220

Glu Asn Trp Tyr Ser Leu Val Val Asp Ala Val Lys Arg Gly Lys Gly
225                 230                 235                 240

Ala Leu Val Phe Val Asn Thr Arg Arg Ser Ala Glu Lys Glu Ala Leu
                245                 250                 255

Ala Leu Ser Lys Leu Val Ser Ser His Leu Thr Lys Pro Glu Lys Arg
            260                 265                 270

Ala Leu Glu Ser Leu Ala Ser Gln Leu Glu Asp Asn Pro Thr Ser Glu
        275                 280                 285

Lys Leu Lys Arg Ala Leu Arg Gly Gly Val Ala Phe His His Ala Gly
    290                 295                 300

Leu Ser Arg Val Glu Arg Thr Leu Ile Glu Asp Ala Phe Arg Glu Gly
305                 310                 315                 320

Leu Ile Lys Val Ile Thr Ala Thr Pro Thr Leu Ser Ala Gly Val Asn
                325                 330                 335

Leu Pro Ser Phe Arg Val Ile Ile Arg Asp Thr Lys Arg Tyr Ala Gly
            340                 345                 350

Phe Gly Trp Thr Asp Ile Pro Val Leu Glu Ile Gln Gln Met Met Gly
        355                 360                 365

Arg Ala Gly Arg Pro Arg Tyr Asp Lys Tyr Gly Glu Ala Ile Ile Val
    370                 375                 380

Ala Arg Thr Asp Glu Pro Gly Lys Leu Met Glu Arg Tyr Ile Arg Gly
385                 390                 395                 400

Lys Pro Glu Lys Leu Phe Ser Met Leu Ala Asn Glu Gln Ala Phe Arg
                405                 410                 415

Ser Gln Val Leu Ala Leu Ile Thr Asn Phe Gly Ile Arg Ser Phe Pro
            420                 425                 430

Glu Leu Val Arg Phe Leu Glu Arg Thr Phe Tyr Ala His Gln Arg Lys
        435                 440                 445

Asp Leu Ser Ser Leu Glu Tyr Lys Ala Lys Glu Val Val Tyr Phe Leu
    450                 455                 460

Ile Glu Asn Glu Phe Ile Asp Leu Asp Leu Glu Asp Arg Phe Ile Pro
465                 470                 475                 480

Leu Pro Phe Gly Lys Arg Thr Ser Gln Leu Tyr Ile Asp Pro Leu Thr
```

```
            485                 490                 495
Ala Lys Lys Phe Lys Asp Ala Phe Pro Ala Ile Glu Arg Asn Pro Asn
            500                 505                 510

Pro Phe Gly Ile Phe Gln Leu Ile Ala Ser Thr Pro Asp Met Ala Thr
            515                 520                 525

Leu Thr Ala Arg Arg Arg Glu Met Glu Asp Tyr Leu Asp Leu Ala Tyr
            530                 535                 540

Glu Leu Glu Asp Lys Leu Tyr Ala Ser Ile Pro Tyr Tyr Glu Asp Ser
545                 550                 555                 560

Arg Phe Gln Gly Phe Leu Gly Gln Val Lys Thr Ala Lys Val Leu Leu
                565                 570                 575

Asp Trp Ile Asn Glu Val Pro Glu Ala Arg Ile Tyr Glu Thr Tyr Ser
                580                 585                 590

Ile Asp Pro Gly Asp Leu Tyr Arg Leu Glu Leu Ala Asp Trp Leu
                595                 600                 605

Met Tyr Ser Leu Ile Glu Leu Tyr Lys Leu Phe Glu Pro Lys Glu Glu
                610                 615                 620

Ile Leu Asn Tyr Leu Arg Asp Leu His Leu Arg Leu Arg His Gly Val
625                 630                 635                 640

Arg Glu Glu Leu Leu Glu Leu Val Arg Leu Pro Asn Ile Gly Arg Lys
                645                 650                 655

Arg Ala Arg Ala Leu Tyr Asn Ala Gly Phe Arg Ser Val Glu Ala Ile
                660                 665                 670

Ala Asn Ala Lys Pro Ala Glu Leu Leu Ala Val Glu Gly Ile Gly Ala
                675                 680                 685

Lys Ile Leu Asp Gly Ile Tyr Arg His Leu Gly Ile Glu Lys Arg Val
                690                 695                 700

Thr Glu Glu Lys Pro Lys Arg Lys Gly Thr Leu Glu Asp Phe Leu Arg
705                 710                 715                 720

<210> SEQ ID NO 21
<211> LENGTH: 799
<212> TYPE: PRT
<213> ORGANISM: Methanospirillum hungatei JF-1

<400> SEQUENCE: 21

Met Glu Ile Ala Ser Leu Pro Leu Pro Asp Ser Phe Ile Arg Ala Cys
1               5                   10                  15

His Ala Lys Gly Ile Arg Ser Leu Tyr Pro Pro Gln Ala Glu Cys Ile
                20                  25                  30

Glu Lys Gly Leu Leu Glu Gly Lys Asn Leu Leu Ile Ser Ile Pro Thr
            35                  40                  45

Ala Ser Gly Lys Thr Leu Leu Ala Glu Met Ala Met Trp Ser Arg Ile
        50                  55                  60

Ala Ala Gly Gly Lys Cys Leu Tyr Ile Val Pro Leu Arg Ala Leu Ala
65                  70                  75                  80

Ser Glu Lys Tyr Asp Glu Phe Ser Lys Lys Gly Val Ile Arg Val Gly
                85                  90                  95

Ile Ala Thr Gly Asp Leu Asp Arg Thr Asp Ala Tyr Leu Gly Glu Asn
            100                 105                 110

Asp Ile Ile Val Ala Thr Ser Glu Lys Thr Asp Ser Leu Leu Arg Asn
        115                 120                 125

Arg Thr Pro Trp Leu Ser Gln Ile Thr Cys Ile Val Leu Asp Glu Val
        130                 135                 140
```

His Leu Ile Gly Ser Glu Asn Arg Gly Ala Thr Leu Glu Met Val Ile
145                 150                 155                 160

Thr Lys Leu Arg Tyr Thr Asn Pro Val Met Gln Ile Ile Gly Leu Ser
            165                 170                 175

Ala Thr Ile Gly Asn Pro Ala Gln Leu Ala Glu Trp Leu Asp Ala Thr
            180                 185                 190

Leu Ile Thr Ser Thr Trp Arg Pro Val Asp Leu Arg Gln Gly Val Tyr
            195                 200                 205

Tyr Asn Gly Lys Ile Arg Phe Ser Asp Ser Glu Arg Pro Ile Gln Gly
210                 215                 220

Lys Thr Lys His Asp Asp Leu Asn Leu Cys Leu Asp Thr Ile Glu Glu
225                 230                 235                 240

Gly Gly Gln Cys Leu Val Phe Val Ser Ser Arg Arg Asn Ala Glu Gly
            245                 250                 255

Phe Ala Lys Lys Ala Ala Gly Ala Leu Lys Ala Gly Ser Pro Asp Ser
            260                 265                 270

Lys Ala Leu Ala Gln Glu Leu Arg Arg Leu Arg Asp Arg Asp Glu Gly
            275                 280                 285

Asn Val Leu Ala Asp Cys Val Glu Arg Gly Ala Ala Phe His His Ala
290                 295                 300

Gly Leu Ile Arg Gln Glu Arg Thr Ile Ile Glu Glu Gly Phe Arg Asn
305                 310                 315                 320

Gly Tyr Ile Glu Val Ile Ala Ala Thr Pro Thr Leu Ala Ala Gly Leu
            325                 330                 335

Asn Leu Pro Ala Arg Arg Val Ile Ile Arg Asp Tyr Asn Arg Phe Ala
            340                 345                 350

Ser Gly Leu Gly Met Val Pro Ile Pro Val Gly Glu Tyr His Gln Met
            355                 360                 365

Ala Gly Arg Ala Gly Arg Pro His Leu Asp Pro Tyr Gly Glu Ala Val
            370                 375                 380

Leu Leu Ala Lys Asp Ala Pro Ser Val Glu Arg Leu Phe Glu Thr Phe
385                 390                 395                 400

Ile Asp Ala Glu Ala Glu Arg Val Asp Ser Gln Cys Val Asp Asp Ala
            405                 410                 415

Ser Leu Cys Ala His Ile Leu Ser Leu Ile Ala Thr Gly Phe Ala His
            420                 425                 430

Asp Gln Glu Ala Leu Ser Ser Phe Met Glu Arg Thr Phe Tyr Phe Phe
            435                 440                 445

Gln His Pro Lys Thr Arg Ser Leu Pro Arg Leu Val Ala Asp Ala Ile
            450                 455                 460

Arg Phe Leu Thr Thr Ala Gly Met Val Glu Glu Arg Glu Asn Thr Leu
465                 470                 475                 480

Ser Ala Thr Arg Leu Gly Ser Leu Val Ser Arg Leu Tyr Leu Asn Pro
            485                 490                 495

Cys Thr Ala Arg Leu Ile Leu Asp Ser Leu Lys Ser Cys Lys Thr Pro
            500                 505                 510

Thr Leu Ile Gly Leu Leu His Val Ile Cys Val Ser Pro Asp Met Gln
            515                 520                 525

Arg Leu Tyr Leu Lys Ala Ala Asp Thr Gln Leu Leu Arg Thr Phe Leu
            530                 535                 540

Phe Lys His Lys Asp Asp Leu Ile Leu Pro Leu Pro Phe Glu Gln Glu
545                 550                 555                 560

Glu Glu Glu Leu Trp Leu Ser Gly Leu Lys Thr Ala Leu Val Leu Thr

```
                    565                 570                 575

Asp Trp Ala Asp Glu Phe Ser Glu Gly Met Ile Glu Arg Tyr Gly
            580                 585                 590

Ile Gly Ala Gly Asp Leu Tyr Asn Ile Val Asp Ser Gly Lys Trp Leu
        595                 600                 605

Leu His Gly Thr Glu Arg Leu Val Ser Val Glu Met Pro Glu Met Ser
    610                 615                 620

Gln Val Val Lys Thr Leu Ser Val Arg Val His His Gly Val Lys Ser
625                 630                 635                 640

Glu Leu Leu Pro Leu Val Ala Leu Arg Asn Ile Gly Arg Val Arg Ala
                645                 650                 655

Arg Thr Leu Tyr Asn Ala Gly Tyr Pro Asp Pro Glu Ala Val Ala Arg
            660                 665                 670

Ala Gly Leu Ser Thr Ile Ala Arg Ile Ile Gly Glu Gly Ile Ala Arg
        675                 680                 685

Gln Val Ile Asp Glu Ile Thr Gly Val Lys Arg Ser Gly Ile His Ser
    690                 695                 700

Ser Asp Asp Asp Tyr Gln Gln Lys Thr Pro Glu Leu Leu Thr Asp Ile
705                 710                 715                 720

Pro Gly Ile Gly Lys Lys Met Ala Glu Lys Leu Gln Asn Ala Gly Ile
                725                 730                 735

Ile Thr Val Ser Asp Leu Leu Thr Ala Asp Glu Val Leu Leu Ser Asp
            740                 745                 750

Val Leu Gly Ala Ala Arg Ala Arg Lys Val Leu Ala Phe Leu Ser Asn
        755                 760                 765

Ser Glu Lys Glu Asn Ser Ser Ser Asp Lys Thr Glu Glu Ile Pro Asp
    770                 775                 780

Thr Gln Lys Ile Arg Gly Gln Ser Ser Trp Glu Asp Phe Gly Cys
785                 790                 795

<210> SEQ ID NO 22
<211> LENGTH: 1756
<212> TYPE: PRT
<213> ORGANISM: Escherichia coli

<400> SEQUENCE: 22

Met Met Ser Ile Ala Gln Val Arg Ser Ala Gly Ser Ala Gly Asn Tyr
1               5                   10                  15

Tyr Thr Asp Lys Asp Asn Tyr Tyr Val Leu Gly Ser Met Gly Glu Arg
            20                  25                  30

Trp Ala Gly Lys Gly Ala Glu Gln Leu Gly Leu Gln Gly Ser Val Asp
        35                  40                  45

Lys Asp Val Phe Thr Arg Leu Leu Glu Gly Arg Leu Pro Asp Gly Ala
    50                  55                  60

Asp Leu Ser Arg Met Gln Asp Gly Ser Asn Lys His Arg Pro Gly Tyr
65                  70                  75                  80

Asp Leu Thr Phe Ser Ala Pro Lys Ser Val Ser Met Met Ala Met Leu
                85                  90                  95

Gly Gly Asp Lys Arg Leu Ile Asp Ala His Asn Gln Ala Val Asp Phe
            100                 105                 110

Ala Val Arg Gln Val Glu Ala Leu Ala Ser Thr Arg Val Met Thr Asp
        115                 120                 125

Gly Gln Ser Glu Thr Val Leu Thr Gly Asn Leu Val Met Ala Leu Phe
    130                 135                 140
```

```
Asn His Asp Thr Ser Arg Asp Gln Glu Pro Gln Leu His Thr His Ala
145                 150                 155                 160

Val Val Ala Asn Val Thr Gln His Asn Gly Glu Trp Lys Thr Leu Ser
            165                 170                 175

Ser Asp Lys Val Gly Lys Thr Gly Phe Ile Glu Asn Val Tyr Ala Asn
            180                 185                 190

Gln Ile Ala Phe Gly Arg Leu Tyr Arg Glu Lys Leu Lys Glu Gln Val
        195                 200                 205

Glu Ala Leu Gly Tyr Glu Thr Glu Val Val Gly Lys His Gly Met Trp
210                 215                 220

Glu Met Pro Gly Val Pro Val Glu Ala Phe Ser Gly Arg Ser Gln Ala
225                 230                 235                 240

Ile Arg Glu Ala Val Gly Glu Asp Ala Ser Leu Lys Ser Arg Asp Val
            245                 250                 255

Ala Ala Leu Asp Thr Arg Lys Ser Lys Gln His Val Asp Pro Glu Ile
            260                 265                 270

Arg Met Ala Glu Trp Met Gln Thr Leu Lys Glu Thr Gly Phe Asp Ile
        275                 280                 285

Arg Ala Tyr Arg Asp Ala Ala Asp Gln Arg Thr Glu Ile Arg Thr Gln
        290                 295                 300

Ala Pro Gly Pro Ala Ser Gln Asp Gly Pro Asp Val Gln Gln Ala Val
305                 310                 315                 320

Thr Gln Ala Ile Ala Gly Leu Ser Glu Arg Lys Val Gln Phe Thr Tyr
                325                 330                 335

Thr Asp Val Leu Ala Arg Thr Val Gly Ile Leu Pro Pro Glu Asn Gly
            340                 345                 350

Val Ile Glu Arg Ala Arg Ala Gly Ile Asp Glu Ala Ile Ser Arg Glu
            355                 360                 365

Gln Leu Ile Pro Leu Asp Arg Glu Lys Gly Leu Phe Thr Ser Gly Ile
        370                 375                 380

His Val Leu Asp Glu Leu Ser Val Arg Ala Leu Ser Arg Asp Ile Met
385                 390                 395                 400

Lys Gln Asn Arg Val Thr Val His Pro Glu Lys Ser Val Pro Arg Thr
                405                 410                 415

Ala Gly Tyr Ser Asp Ala Val Ser Val Leu Ala Gln Asp Arg Pro Ser
            420                 425                 430

Leu Ala Ile Val Ser Gly Gln Gly Ala Ala Gly Gln Arg Glu Arg
        435                 440                 445

Val Ala Glu Leu Val Met Met Ala Arg Glu Gln Gly Arg Glu Val Gln
450                 455                 460

Ile Ile Ala Ala Asp Arg Arg Ser Gln Met Asn Leu Lys Gln Asp Glu
465                 470                 475                 480

Arg Leu Ser Gly Glu Leu Ile Thr Gly Arg Arg Gln Leu Leu Glu Gly
                485                 490                 495

Met Ala Phe Thr Pro Gly Ser Thr Val Ile Val Asp Gln Gly Glu Lys
            500                 505                 510

Leu Ser Leu Lys Glu Thr Leu Thr Leu Leu Asp Gly Ala Ala Arg His
        515                 520                 525

Asn Val Gln Val Leu Ile Thr Asp Ser Gly Gln Arg Thr Gly Thr Gly
        530                 535                 540

Ser Ala Leu Met Ala Met Lys Asp Ala Gly Val Asn Thr Tyr Arg Trp
545                 550                 555                 560

Gln Gly Gly Glu Gln Arg Pro Ala Thr Ile Ile Ser Glu Pro Asp Arg
```

-continued

```
                565                 570                 575
Asn Val Arg Tyr Ala Arg Leu Ala Gly Asp Phe Ala Ala Ser Val Lys
                580                 585                 590
Ala Gly Glu Glu Ser Val Ala Gln Val Ser Gly Val Arg Glu Gln Ala
                595                 600                 605
Ile Leu Thr Gln Ala Ile Arg Ser Glu Leu Lys Thr Gln Gly Val Leu
                610                 615                 620
Gly His Pro Glu Val Thr Met Thr Ala Leu Ser Pro Val Trp Leu Asp
625                 630                 635                 640
Ser Arg Ser Arg Tyr Leu Arg Asp Met Tyr Arg Pro Gly Met Val Met
                645                 650                 655
Glu Gln Trp Asn Pro Glu Thr Arg Ser His Asp Arg Tyr Val Ile Asp
                660                 665                 670
Arg Val Thr Ala Gln Ser His Ser Leu Thr Leu Arg Asp Ala Gln Gly
                675                 680                 685
Glu Thr Gln Val Val Arg Ile Ser Ser Leu Asp Ser Ser Trp Ser Leu
                690                 695                 700
Phe Arg Pro Glu Lys Met Pro Val Ala Asp Gly Glu Arg Leu Arg Val
705                 710                 715                 720
Thr Gly Lys Ile Pro Gly Leu Arg Val Ser Gly Asp Arg Leu Gln
                725                 730                 735
Val Ala Ser Val Ser Glu Asp Ala Met Thr Val Val Pro Gly Arg
                740                 745                 750
Ala Glu Pro Ala Ser Leu Pro Val Ser Asp Ser Pro Phe Thr Ala Leu
                755                 760                 765
Lys Leu Glu Asn Gly Trp Val Glu Thr Pro Gly His Ser Val Ser Asp
770                 775                 780
Ser Ala Thr Val Phe Ala Ser Val Thr Gln Met Ala Met Asp Asn Ala
785                 790                 795                 800
Thr Leu Asn Gly Leu Ala Arg Ser Gly Arg Asp Val Arg Leu Tyr Ser
                805                 810                 815
Ser Leu Asp Glu Thr Arg Thr Ala Glu Lys Leu Ala Arg His Pro Ser
                820                 825                 830
Phe Thr Val Val Ser Glu Gln Ile Lys Ala Arg Ala Gly Glu Thr Leu
                835                 840                 845
Leu Glu Thr Ala Ile Ser Leu Gln Lys Ala Gly Leu His Thr Pro Ala
850                 855                 860
Gln Gln Ala Ile His Leu Ala Leu Pro Val Leu Glu Ser Lys Asn Leu
865                 870                 875                 880
Ala Phe Ser Met Val Asp Leu Leu Thr Glu Ala Lys Ser Phe Ala Ala
                885                 890                 895
Glu Gly Thr Gly Phe Thr Glu Leu Gly Gly Glu Ile Asn Ala Gln Ile
                900                 905                 910
Lys Arg Gly Asp Leu Leu Tyr Val Asp Val Ala Lys Gly Tyr Gly Thr
                915                 920                 925
Gly Leu Leu Val Ser Arg Ala Ser Tyr Glu Ala Glu Lys Ser Ile Leu
                930                 935                 940
Arg His Ile Leu Glu Gly Lys Glu Ala Val Thr Pro Leu Met Glu Arg
945                 950                 955                 960
Val Pro Gly Glu Leu Met Glu Thr Leu Thr Ser Gly Gln Arg Ala Ala
                965                 970                 975
Thr Arg Met Ile Leu Glu Thr Ser Asp Arg Phe Thr Val Val Gln Gly
                980                 985                 990
```

```
Tyr Ala Gly Val Gly Lys Thr Thr Gln Phe Arg Ala Val Met Ser Ala
        995                 1000                1005

Val Asn Met Leu Pro Ala Ser Glu Arg Pro Arg Val Val Gly Leu
    1010                1015                1020

Gly Pro Thr His Arg Ala Val Gly Glu Met Arg Ser Ala Gly Val
    1025                1030                1035

Asp Ala Gln Thr Leu Ala Ser Phe Leu His Asp Thr Gln Leu Gln
    1040                1045                1050

Gln Arg Ser Gly Glu Thr Pro Asp Phe Ser Asn Thr Leu Phe Leu
    1055                1060                1065

Leu Asp Glu Ser Ser Met Val Gly Asn Thr Glu Met Ala Arg Ala
    1070                1075                1080

Tyr Ala Leu Ile Ala Ala Gly Gly Gly Arg Ala Val Ala Ser Gly
    1085                1090                1095

Asp Thr Asp Gln Leu Gln Ala Ile Ala Pro Gly Gln Ser Phe Arg
    1100                1105                1110

Leu Gln Gln Thr Arg Ser Ala Ala Asp Val Val Ile Met Lys Glu
    1115                1120                1125

Ile Val Arg Gln Thr Pro Glu Leu Arg Glu Ala Val Tyr Ser Leu
    1130                1135                1140

Ile Asn Arg Asp Val Glu Arg Ala Leu Ser Gly Leu Glu Ser Val
    1145                1150                1155

Lys Pro Ser Gln Val Pro Arg Leu Glu Gly Ala Trp Ala Pro Glu
    1160                1165                1170

His Ser Val Thr Glu Phe Ser His Ser Gln Glu Ala Lys Leu Ala
    1175                1180                1185

Glu Ala Gln Gln Lys Ala Met Leu Lys Gly Glu Ala Phe Pro Asp
    1190                1195                1200

Ile Pro Met Thr Leu Tyr Glu Ala Ile Val Arg Asp Tyr Thr Gly
    1205                1210                1215

Arg Thr Pro Glu Ala Arg Glu Gln Thr Leu Ile Val Thr His Leu
    1220                1225                1230

Asn Glu Asp Arg Arg Val Leu Asn Ser Met Ile His Asp Ala Arg
    1235                1240                1245

Glu Lys Ala Gly Glu Leu Gly Lys Glu Gln Val Met Val Pro Val
    1250                1255                1260

Leu Asn Thr Ala Asn Ile Arg Asp Gly Glu Leu Arg Arg Leu Ser
    1265                1270                1275

Thr Trp Glu Lys Asn Pro Asp Ala Leu Ala Leu Val Asp Asn Val
    1280                1285                1290

Tyr His Arg Ile Ala Gly Ile Ser Lys Asp Asp Gly Leu Ile Thr
    1295                1300                1305

Leu Gln Asp Ala Glu Gly Asn Thr Arg Leu Ile Ser Pro Arg Glu
    1310                1315                1320

Ala Val Ala Glu Gly Val Thr Leu Tyr Thr Pro Asp Lys Ile Arg
    1325                1330                1335

Val Gly Thr Gly Asp Arg Met Arg Phe Thr Lys Ser Asp Arg Glu
    1340                1345                1350

Arg Gly Tyr Val Ala Asn Ser Val Trp Thr Val Thr Ala Val Ser
    1355                1360                1365

Gly Asp Ser Val Thr Leu Ser Asp Gly Gln Gln Thr Arg Val Ile
    1370                1375                1380
```

Arg Pro Gly Gln Glu Arg Ala Glu Gln His Ile Asp Leu Ala Tyr
1385                1390                1395

Ala Ile Thr Ala His Gly Ala Gln Gly Ala Ser Glu Thr Phe Ala
1400                1405                1410

Ile Ala Leu Glu Gly Thr Glu Gly Asn Arg Lys Leu Met Ala Gly
1415                1420                1425

Phe Glu Ser Ala Tyr Val Ala Leu Ser Arg Met Lys Gln His Val
1430                1435                1440

Gln Val Tyr Thr Asp Asn Arg Gln Gly Trp Thr Asp Ala Ile Asn
1445                1450                1455

Asn Ala Val Gln Lys Gly Thr Ala His Asp Val Leu Glu Pro Lys
1460                1465                1470

Pro Asp Arg Glu Val Met Asn Ala Gln Arg Leu Phe Ser Thr Ala
1475                1480                1485

Arg Glu Leu Arg Asp Val Ala Ala Gly Arg Ala Val Leu Arg Gln
1490                1495                1500

Ala Gly Leu Ala Gly Gly Asp Ser Pro Ala Arg Phe Ile Ala Pro
1505                1510                1515

Gly Arg Lys Tyr Pro Gln Pro Tyr Val Ala Leu Pro Ala Phe Asp
1520                1525                1530

Arg Asn Gly Lys Ser Ala Gly Ile Trp Leu Asn Pro Leu Thr Thr
1535                1540                1545

Asp Asp Gly Asn Gly Leu Arg Gly Phe Ser Gly Glu Gly Arg Val
1550                1555                1560

Lys Gly Ser Gly Asp Ala Gln Phe Val Ala Leu Gln Gly Ser Arg
1565                1570                1575

Asn Gly Glu Ser Leu Leu Ala Asp Asn Met Gln Asp Gly Val Arg
1580                1585                1590

Ile Ala Arg Asp Asn Pro Asp Ser Gly Val Val Arg Ile Ala
1595                1600                1605

Gly Glu Gly Arg Pro Trp Asn Pro Gly Ala Ile Thr Gly Gly Arg
1610                1615                1620

Val Trp Gly Asp Ile Pro Asp Asn Ser Val Gln Pro Gly Ala Gly
1625                1630                1635

Asn Gly Glu Pro Val Thr Ala Glu Val Leu Ala Gln Arg Gln Ala
1640                1645                1650

Glu Glu Ala Ile Arg Arg Glu Thr Glu Arg Arg Ala Asp Glu Ile
1655                1660                1665

Val Arg Lys Met Ala Glu Asn Lys Pro Asp Leu Pro Asp Gly Lys
1670                1675                1680

Thr Glu Leu Ala Val Arg Asp Ile Ala Gly Gln Glu Arg Asp Arg
1685                1690                1695

Ser Ala Ile Ser Glu Arg Glu Thr Ala Leu Pro Glu Ser Val Leu
1700                1705                1710

Arg Glu Ser Gln Arg Glu Arg Glu Ala Val Arg Glu Val Ala Arg
1715                1720                1725

Glu Asn Leu Leu Gln Glu Arg Leu Gln Gln Met Glu Arg Asp Met
1730                1735                1740

Val Arg Asp Leu Gln Lys Glu Lys Thr Leu Gly Gly Asp
1745                1750                1755

<210> SEQ ID NO 23
<211> LENGTH: 726
<212> TYPE: PRT

<213> ORGANISM: Methanococcoides burtonii

<400> SEQUENCE: 23

| | | | | | | | | | | | | | | |
|---|---|---|---|---|---|---|---|---|---|---|---|---|---|---|
| Met | Ser | Asp | Lys | Pro | Ala | Phe | Met | Lys | Tyr | Phe | Thr | Gln | Ser | Ser | Cys |
| 1 | | | | 5 | | | | | 10 | | | | | 15 | |
| Tyr | Pro | Asn | Gln | Gln | Glu | Ala | Met | Asp | Arg | Ile | His | Ser | Ala | Leu | Met |
| | | | 20 | | | | | 25 | | | | | 30 | | |
| Gln | Gln | Gln | Leu | Val | Leu | Phe | Glu | Gly | Ala | Cys | Gly | Thr | Gly | Lys | Thr |
| | | 35 | | | | | 40 | | | | | 45 | | | |
| Leu | Ser | Ala | Leu | Val | Pro | Ala | Leu | His | Val | Gly | Lys | Met | Leu | Gly | Lys |
| | 50 | | | | | 55 | | | | | 60 | | | | |
| Thr | Val | Ile | Ile | Ala | Thr | Asn | Val | His | Gln | Gln | Met | Val | Gln | Phe | Ile |
| 65 | | | | | 70 | | | | | 75 | | | | | 80 |
| Asn | Glu | Ala | Arg | Asp | Ile | Lys | Lys | Val | Gln | Asp | Val | Lys | Val | Ala | Val |
| | | | | 85 | | | | | 90 | | | | | 95 | |
| Ile | Lys | Gly | Lys | Thr | Ala | Met | Cys | Pro | Gln | Glu | Ala | Asp | Tyr | Glu | Glu |
| | | | 100 | | | | | 105 | | | | | 110 | | |
| Cys | Ser | Val | Lys | Arg | Glu | Asn | Thr | Phe | Glu | Leu | Met | Glu | Thr | Glu | Arg |
| | | 115 | | | | | 120 | | | | | 125 | | | |
| Glu | Ile | Tyr | Leu | Lys | Arg | Gln | Glu | Leu | Asn | Ser | Ala | Arg | Asp | Ser | Tyr |
| | 130 | | | | | 135 | | | | | 140 | | | | |
| Lys | Lys | Ser | His | Asp | Pro | Ala | Phe | Val | Thr | Leu | Arg | Asp | Glu | Leu | Ser |
| 145 | | | | | 150 | | | | | 155 | | | | | 160 |
| Lys | Glu | Ile | Asp | Ala | Val | Glu | Lys | Ala | Arg | Gly | Leu | Arg | Asp | Arg |
| | | | | 165 | | | | | 170 | | | | | 175 | |
| Ala | Cys | Asn | Asp | Leu | Tyr | Glu | Val | Leu | Arg | Ser | Asp | Ser | Glu | Lys | Phe |
| | | | 180 | | | | | 185 | | | | | 190 | | |
| Arg | Glu | Trp | Leu | Tyr | Lys | Glu | Val | Arg | Ser | Pro | Glu | Glu | Ile | Asn | Asp |
| | | 195 | | | | | 200 | | | | | 205 | | | |
| His | Ala | Ile | Lys | Asp | Gly | Met | Cys | Gly | Tyr | Glu | Leu | Val | Lys | Arg | Glu |
| | 210 | | | | | 215 | | | | | 220 | | | | |
| Leu | Lys | His | Ala | Asp | Leu | Leu | Ile | Cys | Asn | Tyr | His | His | Val | Leu | Asn |
| 225 | | | | | 230 | | | | | 235 | | | | | 240 |
| Pro | Asp | Ile | Phe | Ser | Thr | Val | Leu | Gly | Trp | Ile | Glu | Lys | Glu | Pro | Gln |
| | | | | 245 | | | | | 250 | | | | | 255 | |
| Glu | Thr | Ile | Val | Ile | Phe | Asp | Glu | Ala | His | Asn | Leu | Glu | Ser | Ala | Ala |
| | | | 260 | | | | | 265 | | | | | 270 | | |
| Arg | Ser | His | Ser | Ser | Leu | Ser | Leu | Thr | Glu | His | Ser | Ile | Glu | Lys | Ala |
| | | 275 | | | | | 280 | | | | | 285 | | | |
| Ile | Thr | Glu | Leu | Glu | Ala | Asn | Leu | Asp | Leu | Leu | Ala | Asp | Asp | Asn | Ile |
| | 290 | | | | | 295 | | | | | 300 | | | | |
| His | Asn | Leu | Phe | Asn | Ile | Phe | Leu | Glu | Val | Ile | Ser | Asp | Thr | Tyr | Asn |
| 305 | | | | | 310 | | | | | 315 | | | | | 320 |
| Ser | Arg | Phe | Lys | Phe | Gly | Glu | Arg | Glu | Arg | Val | Arg | Lys | Asn | Trp | Tyr |
| | | | | 325 | | | | | 330 | | | | | 335 | |
| Asp | Ile | Arg | Ile | Ser | Asp | Pro | Tyr | Glu | Arg | Asn | Asp | Ile | Val | Arg | Gly |
| | | | 340 | | | | | 345 | | | | | 350 | | |
| Lys | Phe | Leu | Arg | Gln | Ala | Lys | Gly | Asp | Phe | Gly | Glu | Lys | Asp | Asp | Ile |
| | | 355 | | | | | 360 | | | | | 365 | | | |
| Gln | Ile | Leu | Leu | Ser | Glu | Ala | Ser | Glu | Leu | Gly | Ala | Lys | Leu | Asp | Glu |
| | 370 | | | | | 375 | | | | | 380 | | | | |
| Thr | Tyr | Arg | Asp | Gln | Tyr | Lys | Lys | Gly | Leu | Ser | Ser | Val | Met | Lys | Arg |
| 385 | | | | | 390 | | | | | 395 | | | | | 400 |

Ser His Ile Arg Tyr Val Ala Asp Phe Met Ser Ala Tyr Ile Glu Leu
            405                 410                 415

Ser His Asn Leu Asn Tyr Tyr Pro Ile Leu Asn Val Arg Arg Asp Met
        420                 425                 430

Asn Asp Glu Ile Tyr Gly Arg Val Glu Leu Phe Thr Cys Ile Pro Lys
            435                 440                 445

Asn Val Thr Glu Pro Leu Phe Asn Ser Leu Phe Ser Val Ile Leu Met
        450                 455                 460

Ser Ala Thr Leu His Pro Phe Glu Met Val Lys Lys Thr Leu Gly Ile
465                 470                 475                 480

Thr Arg Asp Thr Cys Glu Met Ser Tyr Gly Thr Ser Phe Pro Glu Glu
                485                 490                 495

Lys Arg Leu Ser Ile Ala Val Ser Ile Pro Pro Leu Phe Ala Lys Asn
            500                 505                 510

Arg Asp Asp Arg His Val Thr Glu Leu Leu Glu Gln Val Leu Leu Asp
        515                 520                 525

Ser Ile Glu Asn Ser Lys Gly Asn Val Ile Leu Phe Phe Gln Ser Ala
    530                 535                 540

Phe Glu Ala Lys Arg Tyr Tyr Ser Lys Ile Glu Pro Leu Val Asn Val
545                 550                 555                 560

Pro Val Phe Leu Asp Glu Val Gly Ile Ser Ser Gln Asp Val Arg Glu
                565                 570                 575

Glu Phe Phe Ser Ile Gly Glu Glu Asn Gly Lys Ala Val Leu Leu Ser
            580                 585                 590

Tyr Leu Trp Gly Thr Leu Ser Glu Gly Ile Asp Tyr Arg Asp Gly Arg
        595                 600                 605

Gly Arg Thr Val Ile Ile Ile Gly Val Gly Tyr Pro Ala Leu Asn Asp
    610                 615                 620

Arg Met Asn Ala Val Glu Ser Ala Tyr Asp His Val Phe Gly Tyr Gly
625                 630                 635                 640

Ala Gly Trp Glu Phe Ala Ile Gln Val Pro Thr Ile Arg Lys Ile Arg
                645                 650                 655

Gln Ala Met Gly Arg Val Val Arg Ser Pro Thr Asp Tyr Gly Ala Arg
            660                 665                 670

Ile Leu Leu Asp Gly Arg Phe Leu Thr Asp Ser Lys Lys Arg Phe Gly
        675                 680                 685

Lys Phe Ser Val Phe Glu Val Phe Pro Pro Ala Glu Arg Ser Glu Phe
    690                 695                 700

Val Asp Val Asp Pro Glu Lys Val Lys Tyr Ser Leu Met Asn Phe Phe
705                 710                 715                 720

Met Asp Asn Asp Glu Gln
                725

<210> SEQ ID NO 24
<211> LENGTH: 555
<212> TYPE: DNA
<213> ORGANISM: Artificial sequence
<220> FEATURE:
<223> OTHER INFORMATION: MspA-(B2C)

<400> SEQUENCE: 24
atgggtctgg ataatgaact gagcctggtg acgggtcaag atcgtaccct gacggtgcaa      60
caatgggata cctttctgaa tggcgttttt ccgctggatc gtaatcgcct gacccgtgaa     120
tggtttcatt ccggtcgcgc aaaatatatc gtcgcaggcc cgggtgctga cgaattcgaa     180

```
ggcacgctgg aactgggtta tcagattggc tttccgtggt cactgagcgt tagtatcaac    240
ttctcgtaca ccacgccgaa tattaacatc aacaatggta acattaccgc accgccgttt    300
ggcctgaaca gcgtgattac gccgaacctg tttccgggtg ttagcatctc tgcccgtctg    360
ggcaatggtc cgggcattcg cgaagtggca acctttagtg tgcgcgtttc cggcgctaaa    420
ggcggtgtcg cggtgtctaa cgcccacggt accgttacgg gcgcggccgg cggtgtcctg    480
ctgcgtccgt tcgcgcgcct gattgcctct accggcgaca gcgttacgac ctatggcgaa    540
ccgtggaata tgaac                                                    555

<210> SEQ ID NO 25
<211> LENGTH: 185
<212> TYPE: PRT
<213> ORGANISM: Artificial sequence
<220> FEATURE:
<223> OTHER INFORMATION: MspA-(BSC)

<400> SEQUENCE: 25
```

Met Gly Leu Asp Asn Glu Leu Ser Leu Val Asp Gly Gln Asp Arg Thr
1               5                   10                  15

Leu Thr Val Gln Gln Trp Asp Thr Phe Leu Asn Gly Val Phe Pro Leu
            20                  25                  30

Asp Arg Asn Arg Leu Thr Arg Glu Trp Phe His Ser Gly Arg Ala Lys
        35                  40                  45

Tyr Ile Val Ala Gly Pro Gly Ala Asp Glu Phe Glu Gly Thr Leu Glu
    50                  55                  60

Leu Gly Tyr Gln Ile Gly Phe Pro Trp Ser Leu Ser Val Ser Ile Asn
65                  70                  75                  80

Phe Ser Tyr Thr Thr Pro Asn Ile Asn Ile Asn Asn Gly Asn Ile Thr
                85                  90                  95

Ala Pro Pro Phe Gly Leu Asn Ser Val Ile Thr Pro Asn Leu Phe Pro
            100                 105                 110

Gly Val Ser Ile Ser Ala Arg Leu Gly Asn Gly Pro Gly Ile Arg Glu
        115                 120                 125

Val Ala Thr Phe Ser Val Arg Val Ser Gly Ala Lys Gly Gly Val Ala
    130                 135                 140

Val Ser Asn Ala His Gly Thr Val Thr Gly Ala Ala Gly Gly Val Leu
145                 150                 155                 160

Leu Arg Pro Phe Ala Arg Leu Ile Ala Ser Thr Gly Asp Ser Val Thr
                165                 170                 175

Thr Tyr Gly Glu Pro Trp Asn Met Asn
            180                 185